(12) United States Patent
Tomasulo

(10) Patent No.: US 8,518,305 B2
(45) Date of Patent: Aug. 27, 2013

(54) PHOTOCHROMIC MATERIALS

(75) Inventor: Massimiliano Tomasulo, Monroeville, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 185 days.

(21) Appl. No.: 12/912,133

(22) Filed: Oct. 26, 2010

(65) Prior Publication Data
US 2011/0108781 A1    May 12, 2011

Related U.S. Application Data

(60) Provisional application No. 61/255,604, filed on Oct. 28, 2009.

(51) Int. Cl.
| | | |
|---|---|---|
| *G02B 5/23* | (2006.01) | |
| *C07F 7/08* | (2006.01) | |
| *C07F 7/02* | (2006.01) | |
| *C07D 311/00* | (2006.01) | |
| *C07D 493/00* | (2006.01) | |

(52) U.S. Cl.
USPC ............ 252/586; 544/69; 544/79; 546/14; 549/214; 549/382

(58) Field of Classification Search
USPC ............ 252/586; 544/69, 89, 79; 546/14; 548/509; 549/214, 382
See application file for complete search history.

(56) References Cited

U.S. PATENT DOCUMENTS

| | | |
|---|---|---|
| 4,685,783 A | 8/1987 | Heller et al. |
| 5,458,814 A | 10/1995 | Kumar et al. |
| 5,645,767 A | 7/1997 | Van Gemert |
| 5,651,923 A | 7/1997 | Kumar et al. |
| 5,658,501 A | 8/1997 | Kumar et al. |
| 5,698,141 A | 12/1997 | Kumar |
| 5,723,072 A | 3/1998 | Kumar |
| 6,018,059 A | 1/2000 | Chan |
| 6,022,497 A | 2/2000 | Kumar |
| 6,025,026 A | 2/2000 | Smith et al. |

(Continued)

FOREIGN PATENT DOCUMENTS

| | | | |
|---|---|---|---|
| JP | 03093891 A | | 4/1991 |
| JP | 2000-226571 | * | 8/2000 |

(Continued)

OTHER PUBLICATIONS

Techniques in Chemistry, vol. III, "Photochromism", Chapter 3, Glenn H. Brown, Editor, John Wiley and Sons, Inc., New York, 1971.

*Primary Examiner* — Bijan Ahvazi
(74) *Attorney, Agent, or Firm* — Deborah M. Altman

(57) ABSTRACT

The present invention relates to photochromic materials that include a photochromic compound that includes a photochromic substituent (e.g., an indeno-fused naphthopyran) and at least one pendent silane group, which is bonded to the photochromic substituent. The pendent silane groups are selected from certain pendent siloxy-silane groups and/or pendent alkoxy-silane groups represented by general formulas (I) and/or (II) as described in further detail herein. The present invention also relates to photochromic articles, such as photochromic optical elements (e.g., photochromic lenses), and photochromic coating compositions (e.g., curable photochromic coating compositions), that include the photochromic materials of the present invention. The photochromic materials of the present invention have improved compatibility with compositions into which they may be incorporated, for example, coating compositions, such as urethane coating compositions.

10 Claims, 12 Drawing Sheets

(56) References Cited

U.S. PATENT DOCUMENTS

| | | |
|---|---|---|
| 6,068,797 A | 5/2000 | Hunt |
| 6,113,814 A | 9/2000 | Gemert et al. |
| 6,150,430 A | 11/2000 | Walters et al. |
| 6,153,126 A | 11/2000 | Kumar |
| 6,392,043 B1 | 5/2002 | Bourchteine et al. |
| 6,555,028 B2 | 4/2003 | Walters et al. |
| 7,452,611 B2 | 11/2008 | Blackburn et al. |
| 7,465,415 B2 | 12/2008 | Wang et al. |
| 7,527,754 B2 | 5/2009 | Chopra |
| 7,557,208 B2 | 7/2009 | Walters et al. |
| 2006/0228557 A1 | 10/2006 | Kim et al. |
| 2007/0278460 A1 | 12/2007 | Xiao |
| 2007/0278461 A1 | 12/2007 | Petrovskaia et al. |
| 2008/0006798 A1* | 1/2008 | Evans et al. .................. 252/586 |
| 2008/0103301 A1 | 5/2008 | Chopra et al. |

FOREIGN PATENT DOCUMENTS

| | | |
|---|---|---|
| JP | 2000 226571 A | 8/2000 |
| JP | 2004 210657 A | 7/2004 |
| WO | WO 2007 140058 A1 | 12/2007 |
| WO | WO 2007 140071 A1 | 12/2007 |

* cited by examiner

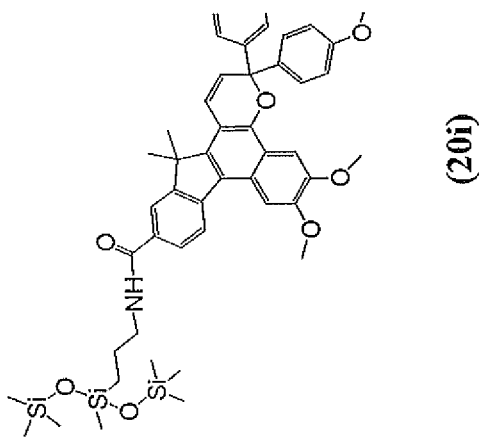
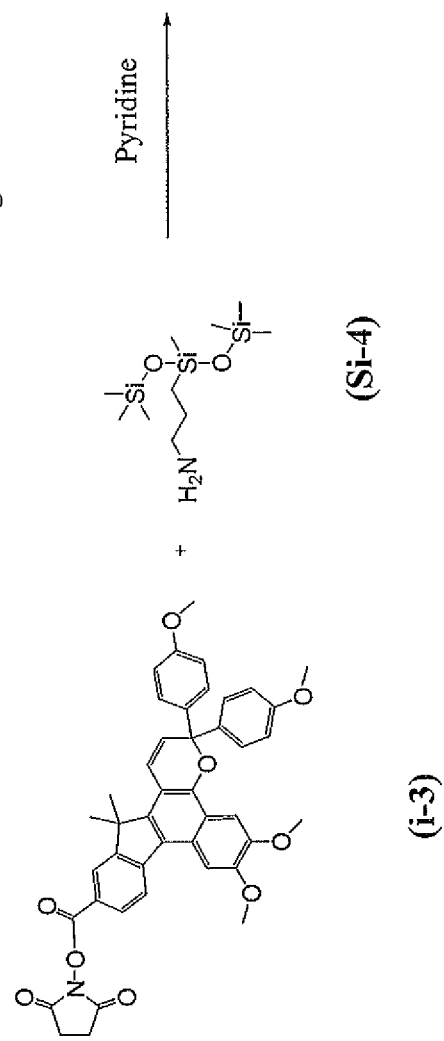
Fig. 10

PHOTOCHROMIC MATERIALS

This application claims priority from Provisional Patent Application 61/255,604 filed Oct. 28, 2009, which is incorporated herein by reference.

FIELD OF THE INVENTION

The present invention relates to photochromic materials that include a photochromic compound that includes a photochromic substituent (e.g., an indeno-fused naphthopyran) and at least one pendent silane group bonded to the photochromic substituent. The pendent silane groups are selected from certain pendent siloxy-silane groups and/or pendent alkoxy-silane groups. The photochromic materials of the present invention provide a desirable combination of molar absorption coefficients, activation times, fade times and linear fade relative to comparable photochromic materials (e.g., the photochromic substituents thereof alone). The photochromic materials of the present invention have improved compatibility with compositions into which they may be incorporated, for example, coating compositions, such as urethane coating compositions.

BACKGROUND OF THE INVENTION

In response to certain wavelengths of electromagnetic radiation (or "actinic radiation"), photochromic materials, such as indeno-fused naphthopyrans, typically undergo a transformation from one form or state to another form, with each form having a characteristic or distinguishable absorption spectrum associated therewith. Typically, upon exposure to actinic radiation, many photochromic materials are transformed from a closed-form, which corresponds to an unactivated (or bleached, e.g., substantially colorless) state of the photochromic material, to an open-form, which corresponds to an activated (or colored) state of the photochromic material. In the absence of exposure to actinic radiation, such photochromic materials are reversibly transformed from the activated (or colored) state, back to the unactivated (or bleached) state. Compositions and articles, such as eyewear lenses, that contain photochromic materials or have photochromic materials applied thereto (e.g., in form of a photochromic coating composition) typically display colorless (e.g., clear) and colored states that correspond to the colorless and colored states of the photochromic materials contained therein or applied thereto.

Upon exposure to actinic radiation (e.g., sunlight), the photochromic material typically is transformed from the unactivated (or bleached) state to the activated (or colored) state over a period of time that is referred to as an activation time. Correspondingly, when exposure to actinic radiation is halted (e.g., due to shielding of sunlight), the photochromic material typically is transformed from the activated (or colored) state to the unactivated (or bleached) state over a period of time that is referred to as a fade time. It is generally desirable that the activation time and the fade time associated with a photochromic material in each case be minimized. In addition, it is desirable that the fade rate associated with a photochromic material be substantially linear. With photochromic eyewear, such as photochromic lenses, a linear fade rate allows the wearer's eyes to adjust more smoothly and less noticeably to the wearer as the lenses transform from a colored to a bleached state.

The amount of a photochromic material required to achieve a desired optical effect when incorporated into a composition or article typically depends, at least in part, on the amount of actinic radiation that the photochromic material is capable of absorbing on a per molecule basis. The amount of actinic radiation that a particular photochromic material absorbs on a per molecule basis is quantitatively referred with regard to the molar absorption coefficient (or "extinction coefficient") of the photochromic material. Photochromic materials having a relatively high molar absorption coefficient are more likely to transform from a closed-form to an open-form upon exposure to actinic radiation, than photochromic materials having a relatively lower molar absorption coefficient. Correspondingly, photochromic materials having a higher molar absorption coefficient may be used in lower concentrations in photochromic compositions and articles, than photochromic materials having a lower molar absorption coefficient, without compromising the desired optical effect.

In some applications, a photochromic material having a relatively high and desirable molar absorption coefficient may have limited solubility in the composition or material into which it is to be incorporated (e.g., a coating composition). As such, compositions or materials in which the photochromic material has low solubility, may be capable of having incorporated therein only a limited and relatively low amount of photochromic material. With a limited and relatively low amount of photochromic material incorporated therein, the resulting photochromic composition would have reduced photochromic properties (e.g., having reduced absorbance when fully activated), than if more photochromic material were capable of being incorporated therein. Accordingly, increasing the solubility of a photochromic material in a particular composition, such as a coating composition, may be desirable in some applications.

It would be desirable to develop new photochromic materials that provide a desirable combination of molar absorption coefficients, activation times, fade times and linear fade relative to comparable photochromic materials. In addition, it would also be desirable that such newly developed photochromic materials have improved solubility in certain compositions, for example coating compositions.

SUMMARY OF THE INVENTION

In accordance with the present invention, there is provided a photochromic material comprising, a photochromic compound comprising a photochromic substituent and at least one pendent silane group bonded to said photochromic substituent, each pendent silane group being selected independently from the group consisting of, (i) pendent silane groups represented by the following general formula I,

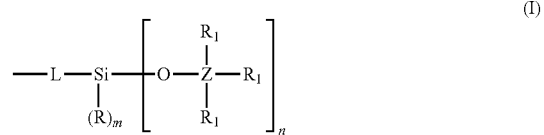

wherein Z for each n is independently Si or C, R is selected from hydrogen or $C_1$-$C_{10}$ hydrocarbyl, each $R_1$ is independently selected from $C_1$-$C_{10}$ hydrocarbyl and halo substituted $C_1$-$C_{10}$ hydrocarbyl, m is 0 or 1, n is 2 or 3, provided that the sum of m and n is 3, and L is a bond or a divalent linking group comprising at least one divalent moiety selected from the group consisting of divalent organic moieties, divalent inorganic moieties and combinations thereof, (ii) pendent silane groups represented by the following general formula II,

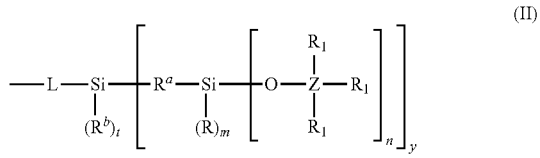

and combinations thereof,
wherein Z, R, $R_1$, m, n and L are each independently as described with regard to general formula (I), $R^a$ is a divalent linking group selected from divalent organic moieties, $R^b$ is selected from hydrogen or $C_1$-$C_{10}$ hydrocarbyl, t is 0, 1 or 2, and y is 1, 2 or 3, provided that the sum of t and y is 3.

As used herein and in the claims, the term "actinic radiation" means electromagnetic radiation that is capable of transforming a photochromic material from one form or state to another.

As used herein, the term "photochromic" means capable of exhibiting a light-induced reversible change of color, for example, exhibiting a reversible change of color in response to at least actinic radiation. Further, as used herein the term "photochromic material" means any substance that is adapted to display photochromic properties, i.e. adapted to change color in response to light, for example, actinic radiation, and which includes at least one photochromic compound.

As used herein and in the claims, the term "photochromic substituent" and similar terms, such as "photochromic moiety" and "photochromic substrate," means a photochromic group that by itself has photochromic properties in the absence of one or more pendent silane groups bonded thereto. The photochromic compounds of the present invention have enhanced properties (e.g., improved matrix solubility and/or improved optical density and/or improved fade rates) relative to the photochromic substituents thereof alone. It should be understood that the at least one pendent silane group bonded to the photochromic substituent of the photochromic compound can be bonded directly to the "core" photochromic moiety (for example, at one of the numbered positions of the photochromic compound represented by general formula (III) hereinbelow), or, where applicable, bonded to a substituent which is bonded directly to the core photochromic moiety (e.g. substituent $R^5$, $R^6$, $R^7$, $R^8$, $R^9$, $R^{10}$, $R^{11}$, and/or $R^{12}$ described with respect to the photochromic compound represented by general formula (III) hereinbelow).

The term "closed-form absorption spectrum," as used herein and in the claims, means the absorption spectrum of a photochromic material in the closed-form or unactivated state of the photochromic material, and more particularly, the wavelength(s) of electromagnetic radiation that cause a photochromic material to undergo the desired closed-form to open-form transformation.

Other than in the operating examples, or where otherwise indicated, all numbers expressing quantities of ingredients, reaction conditions, and so forth used in the specification and claims are to be understood as modified in all instances by the term "about."

BRIEF DESCRIPTION OF THE DRAWINGS

FIG. 10 is a representative schematic diagram of a synthetic reaction scheme depicting the preparation of a photochromic compound according to the present invention in which a pendent silane group represented by general formula (I) is bonded to Position-11 of an indeno-fused naphthopyran prepared in accordance with the synthetic reaction scheme of FIG. 2;

DETAILED DESCRIPTION OF THE INVENTION

Figure 1:
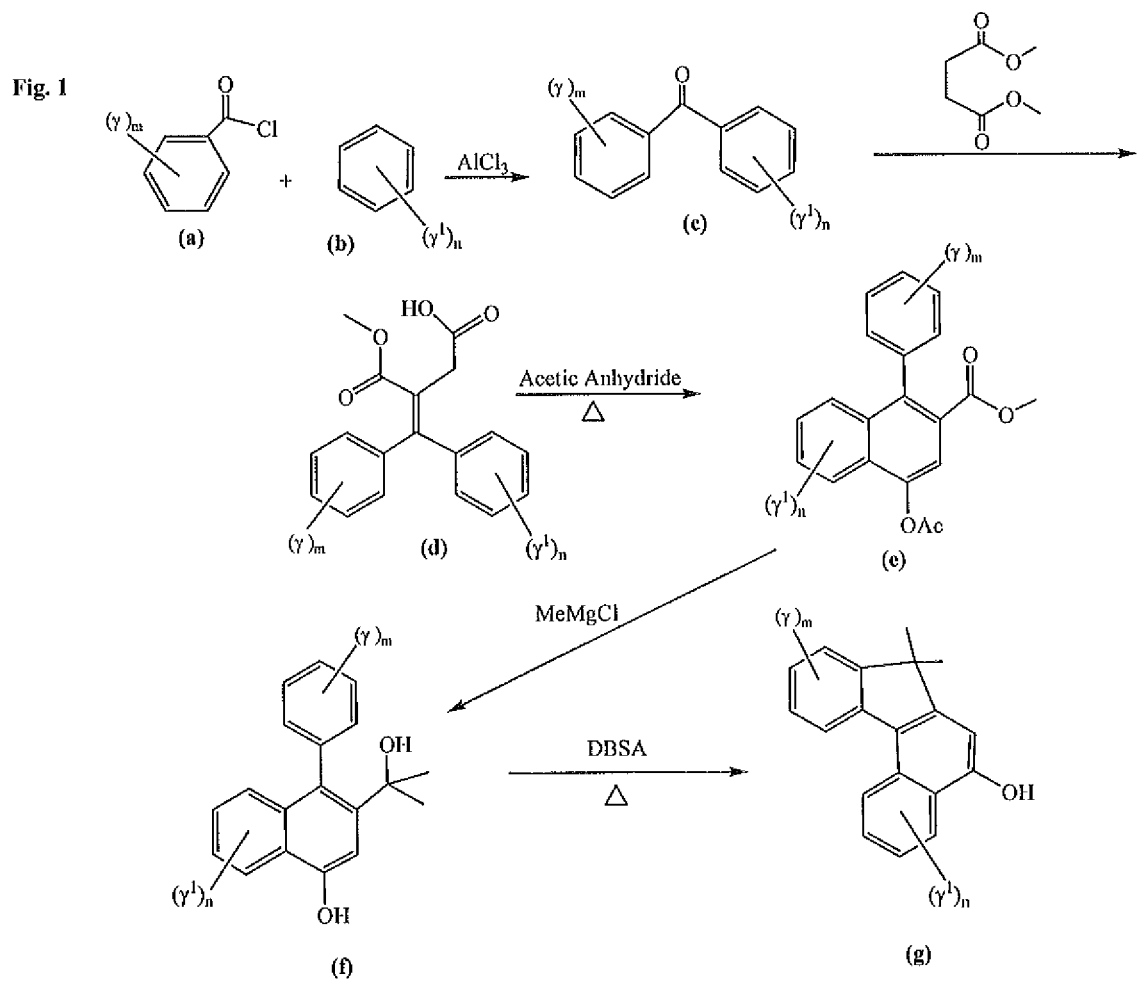
FIG. 1 is a representative schematic diagram of a synthetic reaction scheme for making an intermediate material that may be used in forming photochromic materials according to the present invention.

The photochromic material of the present invention includes a photochromic compound that includes a photochromic substituent having bonded thereto at least one pendent silane selected from one or more of the pendent silanes represented by general formulas (I) and/or (II). The R group of formulas (I) and/or (II) may in each case and for each m be independently selected from hydrogen, $C_1$-$C_{10}$ hydrocarbyl.

As used herein and in the claims the term "hydrocarbyl" and similar terms, such as "hydrocarbyl substituent," means: linear or branched $C_1$-$C_{20}$ alkyl (e.g., linear or branched $C_1$-$C_{10}$ alkyl); linear or branched $C_2$-$C_{20}$ alkenyl (e.g., linear or branched $C_2$-$C_{10}$ alkenyl); linear or branched $C_2$-$C_{20}$ alkynyl (e.g., linear or branched $C_2$-$C_{10}$ alkynyl); $C_3$-$C_{12}$ cycloalkyl (e.g., $C_3$-$C_{10}$ cycloalkyl); $C_3$-$C_{12}$ heterocycloalkyl (having at least one hetero atom in the cyclic ring); $C_5$-$C_{18}$ aryl (including polycyclic aryl groups) (e.g., $C_5$-$C_{10}$ aryl); $C_5$-$C_{18}$ heteroaryl (having at least one hetero atom in the aromatic ring); and $C_6$-$C_{24}$ aralkyl (e.g., $C_6$-$C_{10}$ aralkyl).

Representative alkyl groups include but are not limited to methyl, ethyl, propyl, isopropyl, butyl, isobutyl, sec-butyl, tert-butyl, pentyl, neopentyl, hexyl, heptyl, octyl, nonyl and decyl. Representative alkenyl groups include but are not limited to vinyl, allyl and propenyl. Representative alkynyl groups include but are not limited to ethynyl, 1-propynyl, 2-propynyl, 1-butynyl, and 2-butynyl. Representative cycloalkyl groups include but are not limited to cyclopropyl, cyclobutyl, cyclopentyl, cyclohexyl, and cyclooctyl substituents. Representative heterocycloalkyl groups include but are not limited to tetrahydrofuranyl, tetrahydropyranyl and piperidinyl. Representative aryl groups include but are not limited to phenyl and naphthyl. Representative heteroaryl groups include but are not limited to furanyl, pyranyl and pyridinyl. Representative aralkyl groups include but are not limited to benzyl, and phenethyl.

The term hydrocarbyl as used herein and in the claims is inclusive of halohydrocarbyl (or halo substituted hydrocarbyl) substituents. By halohydrocarbyl (or halo substituted hydrocarbyl) is meant that at least one hydrogen atom of the hydrocarbyl (e.g., of the alkyl, alkenyl, alkynyl, cycloalkyl, aryl and aralkyl groups) is replaced with a halogen atom selected from chlorine, bromine, fluorine and iodine. The degree of halogenation can range from at least one hydrogen atom being replaced by a halogen atom (e.g., a fluoromethyl group) to full halogenation (perhalogenation) wherein all replaceable hydrogen atoms on the hydrocarbyl group have been replaced by a halogen atom (e.g., trifluoromethyl or perfluoromethyl). Perhalohydrocarbyl groups as used herein and in the claims include perhalogenated phenyl and alkyl groups.

The $R_1$ groups of the pendent silane groups represented by formulas (I) and/or (II) may in each case and for each n be independently selected from $C_1$-$C_{10}$ hydrocarbyl and halo substituted $C_1$-$C_{10}$ hydrocarbyl. The terms hydrocarbyl and halo substituted hydrocarbyl relative to $R_1$ are as described previously herein with regard to R. Typically, each R of formulas (I) and (II) is independently selected from hydrogen or linear or branched $C_1$-$C_{10}$ alkyl (e.g., methyl and ethyl), and more typically from hydrogen or methyl. Typically, each $R_1$ of formulas (I) and (II) is selected independently from linear or branched $C_1$-$C_{10}$ alkyl (e.g., methyl or ethyl), and more typically is methyl. In an embodiment of the present invention for the pendent silane groups represented by formulas (I) and (II), m is 0, n is 3 and each $R_1$ is independently methyl or ethyl.

The $R^b$ group of the pendent silane group represented by formula (II) may be selected from hydrogen or $C_1$-$C_{10}$ hydrocarbyl. The term hydrocarbyl relative to $R^b$ is as described previously herein with regard to R. Typically, each $R^b$ of formula (II) is selected from hydrogen or linear or branched $C_1$-$C_{10}$ alkyl (e.g., methyl or ethyl), and more typically hydrogen or methyl. In an embodiment of the present invention, for the pendent silane group represented by formula (II): t is 0 and y is 3; m is 0 and n is 3; and each $R_1$ is independently methyl or ethyl.

The divalent linking group L of the pendent silane groups represented by formulas (I) and (II) may in each case independently be a bond or a divalent linking group comprising at least one divalent moiety selected from one or more divalent organic moieties and/or one or more divalent inorganic moieties. The divalent linking group L may comprise a plurality of divalent organic moieties and a plurality of divalent inorganic moieties. As used herein and in the claims, the term "divalent organic moieties/moiety" and similar terms, such as "divalent organic group(s)" may also be described as "divalent hydrocarbylene moieties." More particularly, as used herein and in the claims, the term "divalent organic moieties/moiety" and similar terms, such as "divalent organic group(s)" means substituted or unsubstituted linear or branched $C_1$-$C_{20}$ alkylene, substituted or unsubstituted linear or branched $C_2$-$C_{20}$ alkenylene, substituted or unsubstituted, linear or branched $C_2$-$C_{10}$ alkynyl, substituted or unsubstituted C unsubstituted $C_3$-$C_{10}$ cycloalkylene, substituted or unsubstituted $C_3$-$C_{10}$ heterocycloalkylene (having at least one hetero atom in the cyclic ring), substituted or unsubstituted arylene (e.g., $C_6$-$C_{18}$ aryl, including polycyclic arylene groups), substituted or unsubstituted heteroarylene (having at least one hetero atom in the cyclic arylene ring or rings).

With regard to the divalent organic moieties from which the divalent linking group L may be selected, representative divalent alkylene groups include but are not limited to methylene (—$CH_2$—), ethylene (—$CH_2CH_2$—), propylene (—$CH_2CH_2CH_2$—), isopropylene (e.g., —$CH_2CH$($CH_3$)—), butylene (—$CH_2CH_2CH_2CH_2$—), isobutylene, sec-butylene, tert-butylene, pentylene, neopentylene, hexylene, heptylene, octylene, nonylene and decylene. Representative divalent alkenylene groups include but are not limited to vinylene (—CH=CH—), and propenylene (e.g., —C($CH_3$)=CH—). Representative divalent alkynylene groups include but are not limited to ethynylene (—CC—), propynylene (—CC—$CH_2$—), and butynylene (e.g., —CC—CH($CH_2$)—). Representative divalent cycloalkylene groups include but are not limited to cyclopropylene, cyclobutylene, cyclopentylene, cyclohexylene, and cyclooctylene. Representative divalent heterocycloalkylene groups include but are not limited to tetrahydrofuranylene, tetrahydropyranylene and piperidinylene. Representative divalent arylene groups include but are not limited to phenylene, naphthylene and anthracenylene. Representative divalent heteroarylene groups include but are not limited to furanylene, pyranylene and pyridinylene. Representative divalent aralkylene groups include but are not limited to benzylene, and phenethylene.

The term "substituted" with regard to the various divalent moieties from which the divalent organic moiety may be selected means that at least one of the substitutable hydrogens of the divalent organic moiety is substituted with another group. For example, a substituted $C_1$-$C_{20}$ alkylene group may be substituted with at least one substituent selected from alkenyl groups, alkynyl groups, cycloalkyl groups, heterocycloalkyl groups, aryl groups and heteroaryl groups. Examples of substituents of the substituted divalent organic moieties include, but are not limited to: alkyl groups (e.g., methyl, ethyl, propyl, isopropyl, butyl, isobutyl, sec-butyl, tert-butyl, pentyl, neopentyl, hexyl, heptyl, octyl, nonyl and decyl); alkenyl groups (e.g., vinyl, allyl and propenyl); alkynyl groups (e.g., ethynyl, 1-propynyl, 2-propynyl, 1-butynyl, and 2-butynyl); cycloalkyl groups (e.g., cyclopropyl, cyclobutyl, cyclopentyl, cyclohexyl, and cyclooctyl); heterocycloalkyl groups (e.g., tetrahydrofuranyl, tetrahydropyranyl and piperidinyl); aryl groups (e.g., phenyl, biphenyl, naphthyl and anthracenyl); arakyl groups (e.g., benzyl and phenethyl) and heteroaryl groups (e.g., furanyl, pyranyl and pyridinyl); halo or halogen groups (e.g., chloro, bromo, fluoro and iodo); ketones (e.g., hydrocarbyl ketones); carboxylic acid esters (e.g., hydrocarbyl carboxylates); hydroxyl; thiol; amino groups (e.g., —$NH_2$); ethers (e.g., hydrocarbyl ethers); thio ethers (e.g., hydrocarbyl thio ethers); and combinations thereof.

The term "unsubstituted" with regard to the various divalent moieties from which the divalent organic moiety may be selected means that none of the substitutable hydrogens of the divalent organic moiety are substituted with another group (e.g., a halogen).

Additional divalent groups from which the divalent organic moieties, of the divalent linking group L of the pendent silane groups represented by formulas (I) and (II), may be selected include, but are not limited to: —N($R_2$)—; —C($R_3$)($R_4$)—C(O)—O—; —C($R_5$)($R_6$)—C(O)—N($R_7$)—; —C(O)—N($R_7$)—;

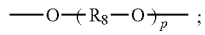

and —$R_9$—O—. With these additional divalent organic moieties, $R_2$, $R_3$, $R_1$, $R_5$, $R_6$ and $R_7$ may each independently be selected from substituted or unsubstituted, linear or branched $C_1$-$C_{20}$ alkyl, substituted or unsubstituted $C_3$-$C_{10}$ cycloalkyl, substituted or unsubstituted $C_3$-$C_{10}$ heterocycloalkyl, substituted or unsubstituted aryl, and substituted or unsubstituted heteroaryl. The $R_3$, $R_4$, $R_5$ and $R_6$ groups may each independently also be hydrogen. When $R_2$ and $R_7$ are each hydrogen, the related divalent linking groups, —N($R_2$)— and —C(O)—N($R_7$)—, are characterized herein more so as divalent inorganic linking groups, as further recited and categorized below.

With regard to the divalent organic moiety represented by the following general formula,

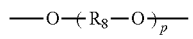

the $R_8$ group, for each p, may independently be selected from substituted or unsubstituted, linear or branched $C_1$-$C_{20}$ alkylene, substituted or unsubstituted, linear or branched $C_2$-$C_{20}$ alkenylene, substituted or unsubstituted, linear or branched $C_2$-$C_{20}$ alkynylene, and substituted or unsubstituted $C_3$-$C_{10}$ cycloalkylene (in which the terms substituted, unsubstituted, alkylene, alkenylene, alkynylene and cycloalkylene are as described previously herein). The subscript "p" may be an integer of at least 1, for example from 1 to 100, or 1 to 50, or 1 to 25 or 1 to 10, inclusive of the recited numbers.

With regard to the divalent organic moiety —$R_9$—O—, $R_9$ may be selected from, for example, substituted or unsubstituted, linear or branched $C_1$-$C_{20}$ alkylene, substituted or unsubstituted, linear or branched $C_2$-$C_{20}$ alkenylene, substituted or unsubstituted, linear or branched $C_2$-$C_{20}$ alkynylene, substituted or unsubstituted $C_3$-$C_{10}$ cycloalkylene, and substituted or unsubstituted arylene (in which the terms substituted, unsubstituted, alkylene, alkenylene, alkynylene and cycloalkylene are as described previously herein).

The divalent inorganic linking group, of the divalent linking group L of the pendent silane groups represented by formulas (I) and (II), may be selected from, for example, at least one of: —O—; —S—; Si($R_1$)$_2$— in which each $R_1$ is independently as described with regard to formulas (I) and (II); —NH—; —C(O)—; —C(O)—O—; —O—C(O)—O—; —C(O)—NH—; —NH—C(O)—O—; —NH—C(O)—S—; —NH—C(S)—O—; and —NH—C(S)—S—.

The divalent linking group $R^a$ of the pendent silane group represented by general formula (II) is selected from divalent organic moieties. The divalent organic moieties from which divalent linking group $R^a$ may be selected include one or more of those classes and examples of divalent organic moieties as recited previously herein with regard to the divalent linking group L. For example, the divalent linking group $R^a$ may be selected from linear or branched $C_1$-$C_{10}$ alkylene, eg., methylene (—$CH_2$—), ethylene (—$CH_2CH_2$—), propylene (—$CH_2CH_2CH_2$—), isopropylene (e.g., —$CH_2CH$($CH_3$)—), butylene (—$CH_2CH_2CH_2CH_2$—), isobutylene, sec-butylene, tert-butylene, pentylene, neopentylene, hexylene, heptylene, octylene, nonylene and decylene.

In an embodiment of the present invention, the divalent linking group L of the pendent silane groups represented by general formulas (I) and (II) in each case independently comprises at least one divalent moiety selected from —O—, —S—, —N($R_2$)—, —C(O)—, —C(O)—O—, —O—C(O)—O—, —C($R_3$)($R_4$)—C(O)—O—, —C($R_5$)($R_6$)—C(O)—N($R_7$)—, —C(O)—N($R_7$)—, —NH—C(O)—O—, —NH—C(O)—S—, —NH—C(S)—O—, —NH—C(S)—S—,

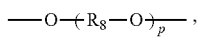

—$R_9$—O—, substituted or unsubstituted, linear or branched $C_1$-$C_{20}$ alkylene, substituted or unsubstituted, linear or branched $C_2$-$C_{20}$ alkynylene, substituted or unsubstituted, linear or branched $C_2$-$C_{20}$ alkynylene, substituted or unsubstituted $C_3$-$C_{10}$ cycloalkylene, substituted or unsubstituted $C_3$-$C_{10}$ heterocycloalkylene, substituted or unsubstituted arylene, substituted or unsubstituted heteroarylene, and combinations of two or more thereof. The $R_1$, $R_2$, $R_3$, $R_4$, $R_5$, $R_6$, $R_7$, $R_8$ and $R_9$ groups are each as described previously herein. The subscript p is as described previously herein (e.g., from 1 to 100). In this particular embodiment, the divalent linking group $R^a$ of formula (II) is selected from linear or branched $C_1$-$C_{10}$ alkylene.

Each divalent linking group L may be formed from, or composed of, a single divalent organic moiety, a single divalent inorganic moiety, combinations of two or more divalent organic moieties, combinations of two or more divalent inorganic moieties, or combinations of one or more divalent organic moieties and one or more divalent inorganic moieties (in each case selected from, for example, those classes and examples of divalent linking groups as recited previously herein). For example, a divalent linking group represented by the following general formula,

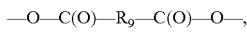
—O—C(O)—R$_9$—C(O)—O—, may be described as being composed of: a divalent organic moiety —O—C(O)—; for example, a divalent substituted or unsubstituted, linear or branched C$_1$-C$_{20}$ or C$_1$-C$_{10}$ alkylene group for —R$_9$—; and another divalent organic moiety —O—C(O)—. For purposes of further illustration, a divalent linking group represented by the following general formula,

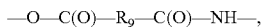
—O—C(O)—R$_9$—C(O)—NH—, may be described as being composed of: a divalent organic moiety —O—C(O)—; for example, a divalent substituted or unsubstituted, linear or branched C$_1$-C$_{20}$ or C$_1$-C$_{10}$ alkylene group for —R$_9$—; and a further divalent organic moiety —C(O)—N(R$_7$)—, where R$_7$ is hydrogen. An example of a combination of a divalent arylene moiety (e.g., phenylene) and a divalent heterocycloalkyl moiety (e.g., N-piperidinylene), is represented by the following general formula,

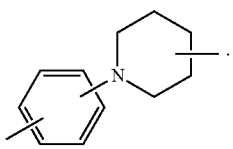

In a further embodiment, the divalent linking group L, of the pendent silane groups represented by general formulas (I) and (II), in each case independently comprises at least one divalent moiety selected from —O—, —Si(R$_1$)$_2$—, —C(O)—O—,

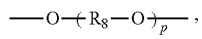

—R$_9$—O—, substituted or unsubstituted, linear or branched C$_1$-C$_{10}$ alkylene, substituted or unsubstituted, linear or branched C$_2$-C$_{10}$ alkenylene, substituted or unsubstituted, linear or branched C$_2$-C$_{10}$ alkynylene, —O—C(O)—R$_9$—C(O)—O—, —O—C(O)—R$_9$—C(O)—NH—,

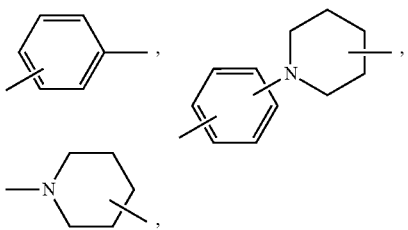

and combinations of two or more thereof. With this particular embodiment, R$_8$ for each p is independently selected from substituted or unsubstituted, linear or branched C$_1$-C$_{10}$ alkylene, substituted or unsubstituted, linear or branched C$_2$-C$_{10}$ alkenylene, substituted or unsubstituted, and linear or branched C$_2$-C$_{10}$ alkynylene, and p is from 1 to 10. Each divalent R$_9$ group, in this particular embodiment, is selected independently from substituted or unsubstituted, linear or branched C$_1$-C$_{10}$ alkylene, substituted or unsubstituted, linear or branched C$_2$-C$_{10}$ alkenylene, substituted or unsubstituted, linear or branched C$_2$-C$_{10}$ alkynylene, substituted or unsubstituted C$_3$-C$_{10}$ cycloalkylene, and substituted or unsubstituted arylene.

Each divalent linking group L, of the pendent silane groups represented by general formulas (I) and (II), may further be independently selected from,

—C(O)—NH—R$_{10}$—,

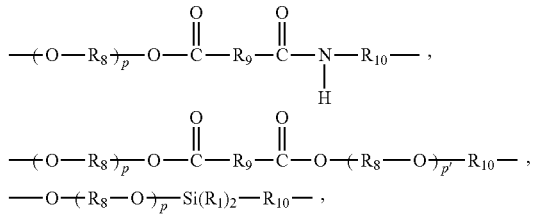

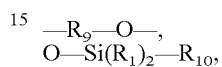
—R$_9$—O—,
O—Si(R$_1$)$_2$—R$_{10}$,

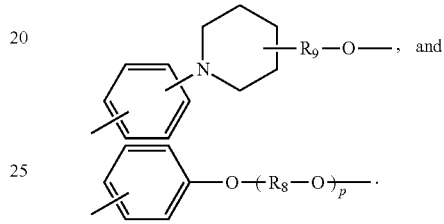

In this particular embodiment, R$_8$ for each p is independently selected from substituted or unsubstituted, linear or branched C$_1$-C$_{10}$ alkylene, substituted or unsubstituted, linear or branched C$_2$-C$_{10}$ alkenylene, substituted or unsubstituted, and linear or branched C$_2$-C$_{10}$ alkynylene. Each divalent R$_9$ group, in this particular embodiment, is selected independently from substituted or unsubstituted, linear or branched C$_1$-C$_{10}$ alkylene, substituted or unsubstituted, linear or branched C$_2$-C$_{10}$ alkenylene, substituted or unsubstituted, linear or branched C$_2$-C$_{10}$ alkynylene, substituted or unsubstituted C$_3$-C$_{10}$ cycloalkylene, and substituted or unsubstituted arylene. Each divalent R$_{10}$ group is independently selected from substituted or unsubstituted, linear or branched C$_1$-C$_{10}$ alkylene, substituted or unsubstituted, linear or branched C$_2$-C$_{10}$ alkenylene, substituted or unsubstituted, linear or branched C$_2$-C$_{10}$ alkynylene, substituted or unsubstituted C$_3$-C$_{10}$ cycloalkylene, and substituted or unsubstituted arylene. Regarding the subscripts: p is from 1 to 10; p' is from 1 to 10 (e.g., from 2 to 10), and q is from 1 to 10.

For purposes of further illustrating that each divalent linking group L may be formed from, or composed of, combinations of those classes and examples of divalent linking groups as recited previously herein, the following divalent linking group,

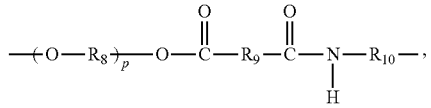

may be described as being composed of the following divalent moieties:

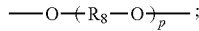

—O—C(O)—R$_9$—C(O)—NH—; and, for example, a substituted or unsubstituted, linear or branched C$_1$-C$_{20}$ or C$_1$-C$_{10}$ alkylene group for —R$_{10}$—.

Similarly, the following divalent linking group,

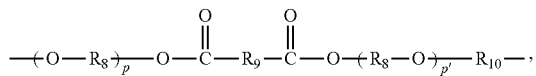

may be described as being composed of the following divalent moieties:

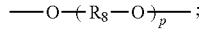

—O—C(O)—R$_9$—C(O)—O—;

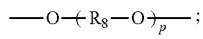

and for example, a substituted or unsubstituted, linear or branched C$_1$-C$_{20}$ or C$_1$-C$_{10}$ alkylene group for —R$_{10}$—.

In a particular embodiment of the present invention, for the pendent silane groups represented by formulas (I) and (II): each R$_1$ is independently linear or branched C$_1$-C$_{10}$ alkyl (e.g., methyl or ethyl); each R is independently hydrogen or linear or branched C$_1$-C$_{10}$ alkyl (e.g., methyl or ethyl); and R$^b$, of formula (II) is hydrogen or linear or branched C$_1$-C$_{10}$ alkyl (e.g., hydrogen, methyl or ethyl).

Non-limiting examples of pendent silane groups, of the photochromic materials of the present invention, are described in further detail herein with reference to the following general formulas, in which the symbol PC represents a photochromic substituent to which the various pendent silane groups are bonded. In the following general formulas, while a single pendent silane group is depicted as being bonded to the photochromic substituent, a plurality of (e.g., 2 or more) pendent silane groups, which may be the same or different, may be bonded to the photochromic substituent.

A photochromic compound according to the present invention, in which the pendent silane group is represented by general formula (I), is represented by the following general formula (I),

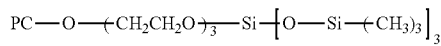

in which m is 0, n is 3, Z is Si, each R$_1$ is methyl, and L is a divalent linking group represented by the following general formula (1a),

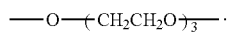

Another photochromic compound according to the present invention, in which the pendent silane group is represented by general formula (I), is represented by the following general formula (2),

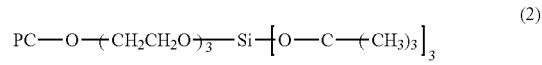

in which m is 0, n is 3, Z is C, each R$_1$ is methyl, and L is a divalent linking group represented by the following general formula (1a),

A further photochromic compound according to the present invention, in which the pendent silane group is represented by general formula (I), is represented by the following general formula (3),

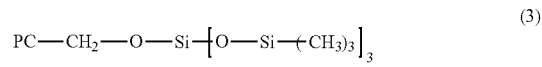

in which m is 0, n is 3, Z is Si, each R$_1$ is methyl, and L is a divalent linking group represented by the following general formula (3a), —CH$_2$—O—. (3a)

In an embodiment, a photochromic compound according to the present invention having a pendent silane group represented by general formula (I), is represented by the following general formula (4),

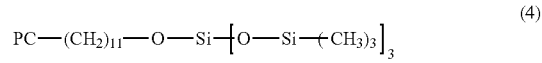

in which m is 0, n is 3, Z is Si, each R$_1$ is methyl, and L is a divalent linking group represented by the following general formula (4a), —(CH$_2$)$_{11}$—O—. (4a)

In another embodiment, a photochromic compound according to the present invention having a pendent silane group represented by general formula (I), is represented by the following general formula (5),

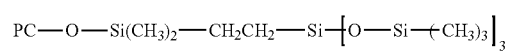

in which m is 0, n is 3, Z is Si, each R$_1$ is methyl, and L is a divalent linking group represented by the following general formula (5a), —O—Si(CH$_3$)$_2$—CH$_2$CH$_2$—. (5a)

In a further embodiment, a photochromic compound according to the present invention having a pendent silane group represented by general formula (I), is represented by the following general formula (6),

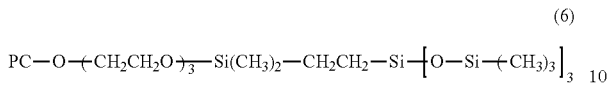
(6)

in which m is 0, n is 3, Z is Si, each $R_1$ is methyl, and L is a divalent linking group represented by the following general formula (6a),

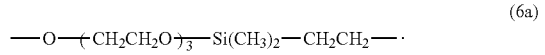
(6a)

A photochromic compound according to the present invention, in which the pendent silane group is represented by general formula (I), is represented by the following general formula (7),

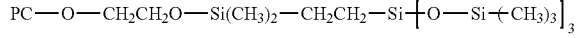
(7)

in which m is 0, n is 3, Z is Si, each $R_1$ is methyl, and L is a divalent linking group represented by the following general formula (7a),

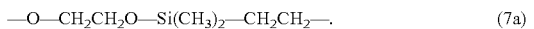
(7a)

Another photochromic compound according to the present invention, in which the pendent silane group is represented by general formula (I), is represented by the following general formula (8),

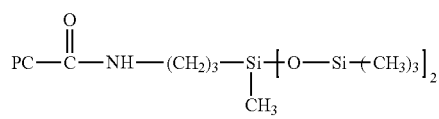
(8)

in which m is 1, R is methyl, n is 2, Z is Si, each $R_1$ is methyl, and L is a divalent linking group represented by the following general formula (8a),

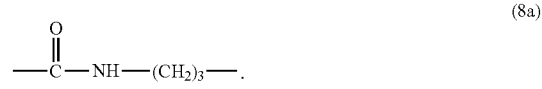
(8a)

A further photochromic compound according to the present invention, in which the pendent silane group is represented by general formula (I), is represented by the following general formula (9),

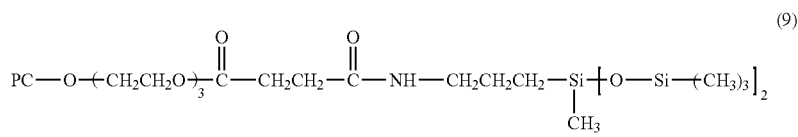
(9)

in which m is 1, R is methyl, n is 2, Z is Si, each $R_1$ is methyl, and L is a divalent linking group represented by the following general formula (9a),

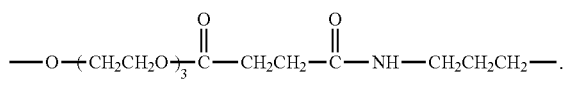
(9a)

In an embodiment, a photochromic compound according to the present invention having a pendent silane group represented by general formula (I), is represented by the following general formula (10),

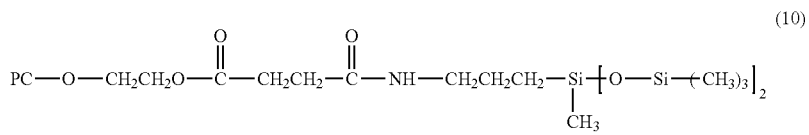
(10)

in which m is 1, R is methyl, n is 2, Z is Si, each $R_1$ is methyl, and L is a divalent linking group represented by the following general formula (10a),

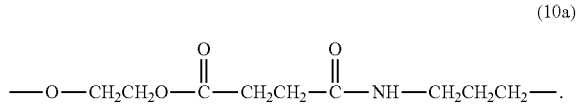
(10a)

A photochromic compound according to the present invention, in which the pendent silane group is represented by general formula (I), is represented by the following general formula (11),

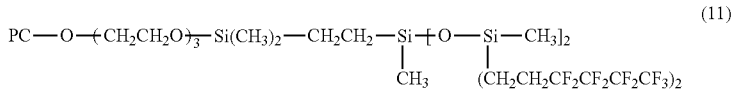
(11)

in which m is 1, R is methyl, n is 2, Z is Si, one $R_1$ is methyl, the remaining $R_1$ groups are each —$CH_2CH_2CF_2CF_2CF_2CF_3$, and L is a divalent linking group represented by the following general formula (11a),

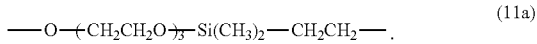
(11a)

In another embodiment, a photochromic compound according to the present invention having a pendent silane group represented by general formula (I), is represented by the following general formula (13),

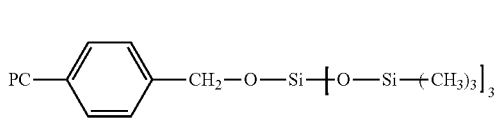
(13)

in which m is 0, n is 3, Z is Si, each $R_1$ is methyl, and L is a divalent linking group represented by the following general formula (13a),

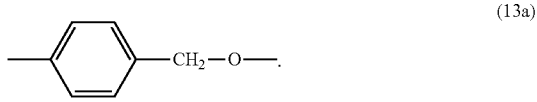
(13a)

A further photochromic compound according to the present invention, in which the pendent silane group is represented by general formula (I), is represented by the following general formula (14),

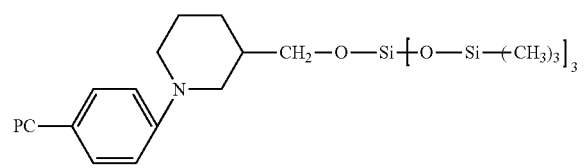
(14)

in which m is 0, n is 3, Z is Si, each $R_1$ is methyl, and L is a divalent linking group represented by the following general formula (14a),

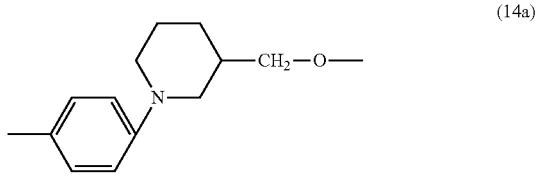
(14a)

A photochromic compound according to the present invention, in which the pendent silane group is represented by general formula (I), is represented by the following general formula (15),

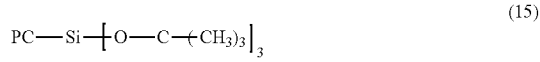
(15)

in which m is 0, n is 3, Z is Si, each $R_1$ is methyl, and L is a bond.

A photochromic compound according to the present invention, in which the pendent silane group is represented by general formula (II), is represented by the following general formula (16),

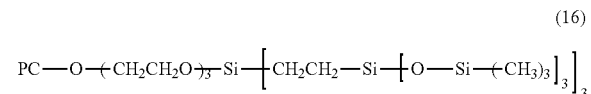
(16)

in which t is 0, y is 3, m is 0, n is 3, Z is Si, each $R_1$ is methyl, $R^a$ is —$CH_2CH_2$—, and L is a divalent linking group represented by the following general formula (1a),

(1a)

A further photochromic compound according to the present invention, in which the pendent silane group is represented by general formula (II), is represented by the following general formula (17),

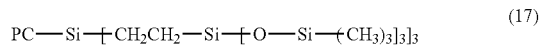
(17)

in which t is 0, y is 3, m is 0, n is 3, Z is Si, each $R_1$ is methyl, $R^a$ is —$CH_2CH_2$—, and L is a bond.

The photochromic substituent or moiety of the photochromic compounds and compounds according to the present invention may be selected from known photochromic substituents. While the photochromic substituent may be selected from inorganic photochromic substituents and organic photochromic substituents, it is typically selected from organic photochromic substituents.

The photochromic substituent of the photochromic compound of the present invention may be selected, for example from, photochromic pyrans (including photochromic spiropyrans), photochromic oxazines (including spiro-oxazines), photochromic fulgides, photochromic fulgimides, photochromic perimidinespirocyclohexadienones, photochromic stilbenes, photochromic thioindigoids, photochromic azo dyes, photochromic diarylethenes, and combinations (e.g., mixtures) of two or more thereof.

Examples of photochromic pyrans, include but are not limited to: benzopyrans; naphthopyrans, e.g., naphtho[1,2-b] pyrans, naphtho[2,1-b]pyrans; indenonaphthopyrans, such as those disclosed in U.S. Pat. No. 5,645,767 at col. 2, line 16 to col. 12, line 57; heterocyclic-fused naphthopyrans, such as those disclosed in U.S. Pat. No. 5,723,072 at col. 2, line 27 to col. 15, line 55; U.S. Pat. No. 5,698,141 at col. 2, line 11 to col. 19, line 45, U.S. Pat. No. 6,153,126 at col. 2, line 26 to col. 8, line 60, and U.S. Pat. No. 6,022,497 at col. 2, line 21 to col. 11, line 46, which disclosures are hereby specifically incorporated by reference herein; spiro-9-fluoreno[1,2-b] pyrans; phenanthropyrans; quinolinopyrans; fluoroanthenopyrans; and spiropyrans, e.g., spiro(benzindoline)naphthopyrans, spiro(indoline)benzopyrans, spiro(indoline)naphthopyrans, and spiro(indoline)pyrans. Further examples of naphthopyrans, include but are not limited to those described in U.S. Pat. No. 5,658,501 at col. 1, line 64 to col. 13, line 17, which disclosure is hereby specifically incorporated by reference herein. Spiro(indoline)pyrans are also described in the text, Techniques in Chemistry, Volume III, "Photochromism", Chapter 3, Glenn H. Brown, Editor, John Wiley and Sons, Inc., New York, 1971.

Examples of photochromic oxazines include, but are not limited to, benzoxazines; naphthoxazines; and spiro-oxazines, e.g., spiro(indoline)naphthoxazines, spiro(indoline)pyridobenzoxazines, spiro(benzindoline)pyridobenzoxazines, spiro(benzindoline)naphthoxazines, spiro(indoline)benzoxazines, spiro(indoline)fluoranthenoxazines, and spiro(indoline)quinoxazines.

Examples of thermally reversible photochromic fulgides and fulgimides include, but are not limited to, those fulgides and fulgimides that are disclosed in U.S. Pat. No. 4,685,783 at col. 1, line 57 to col. 5, line 27, the disclosure of which is hereby specifically incorporated by reference herein.

The photochromic substituent of the photochromic materials and compounds according to the present invention, may include combinations (e.g., mixtures) of two or more of any of the classes and examples of photochromic substituents/moieties described herein-above.

In a particular embodiment of the present invention, the photochromic substituent of the photochromic compound is selected from one or more indeno-fused naphthopyrans. At least one position of the indeno-fused naphthopyran has a pendent silane group represented by formulas (I) and/or (II) bonded thereto. (It should be understood that for purposes of the present invention, the at least one pendent silane group can be bonded directly to the "core" photochromic substituent or bonded to a substituent which is bonded directly to the core photochromic substituent as described in more detail below.) As will be discussed in further detail herein, an indeno-fused naphthopyran typically has 10 to 12 available positions to which a pendent silane group may be bonded. Two of the 10 to 12 available positions of an indeno-fused naphthopyran may have two pendent silane groups bonded thereto. While all available positions of the indeno-fused naphthopyran may have a pendent silane group represented by formulas (I) and/or (II) bonded thereto, typically at least one and less than all available positions of the indeno-fused naphthopyran have a pendent silane group bonded thereto. In an embodiment, the indeno-fused naphthopyran has 1 or 2 pendent silane groups represented by formulas (I) and/or (II) bonded thereto.

In an embodiment, the photochromic material includes, as the photochromic substituent of the photochromic compound, an indeno-fused naphthopyran, for example as represented by the following general formula (III), in which the ring atoms are numbered as shown,

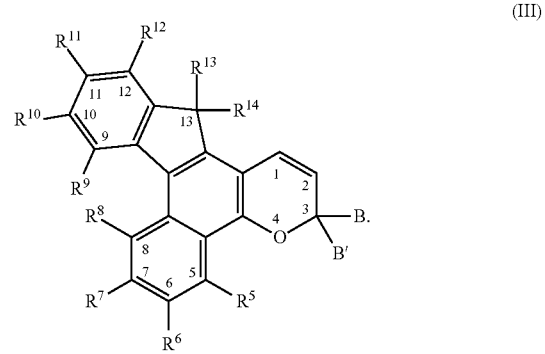

(III)

The B and B' groups of the indeno-fused naphthopyran represented by general formula (III) are each independently selected from substituted and unsubstituted aromatic groups, and substituted and unsubstituted heteroaromatic groups, or B and B' taken together form an unsubstituted or substituted fluoren-9-ylidene.

The indeno-fused naphthopyran represented by general formula (III) has at least one pendent silane group represented by formula (I) and/or formula (II) bonded thereto. As discussed previously herein, the B and B' groups of the indeno-fused naphthopyran are each independently selected from aromatic groups, heteroaromatic groups, or together form a fluoren-9-ylidene group. As such, the pendent silane group(s) may be described as: (i) being bonded to a B group and/or a B' group; or (ii) the divalent linking group L of the pendent silane group includes a divalent aromatic, or heteroaromatic or fluoren-9-ylidene moiety that is bonded directly to the 3 position of the indeno-fused naphthopyran represented by general formula (III).

As was mentioned previously, the at least one pendent silane group can be bonded directly to the indeno-fused naphthopyran at the positions numerically designated in general formula (III), and/or the at least one pendent silane group can be bonded, where applicable, to one of the substitutents (e.g. $R^5$, $R^6$, $R^7$, $R^8$, $R^9$, $R^{16}$, $R^{11}$, or $R^{12}$) which is bonded directly to the indeno-fused naphthopyran.

While indeno-fused naphthopyrans according to the present invention have bonded thereto at least one pendent silane group (e.g., 1 or 2 pendent silane group) represented by general formulas (I) and/or (II), the 1 and 2 positions of the indeno-naphthopyran, e.g., represented by general formula (III), are each typically free of a pendent silane group bonded thereto. With the indeno-fused naphthopyrans according to the present invention, for example as represented by general formula (III): (a) at least one of $R^5$, $R^6$, $R^7$, $R^8$, $R^9$, $R^{10}$, $R^{11}$, $R^{12}$, $R^{13}$ and $R^{14}$ is a pendent silane group represented by formula (I) and/or formula (II), as described previously herein; and/or (b) at least one of B and B' has bonded thereto at least one pendent silane group represented by general formula (I) and/or general formula (II).

The indeno-fused naphthopyran represented by general formula (III) may be referred to as an indeno[2',3':3,4]naphtho[1,2-b]pyran. The indeno-naphthopyran may be selected from one or more indeno[2',2':3,4]naphtho[1,2-b]pyrans represented by general formula (III), and/or one or more indeno[1',2':4,3]naphtho[2,1-b]pyrans represented by the following general Formula-(IV), in which the ring atoms are numbered as shown,

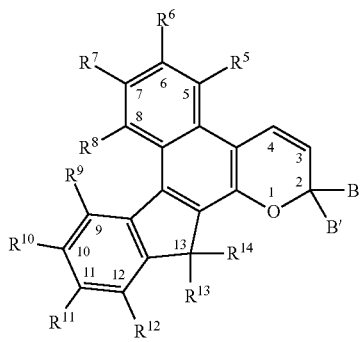

(IV)

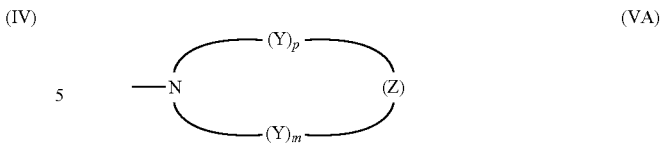

(VA)

The $R^5$ through $R^{14}$, B and B' groups of the indeno[1',2':4,3]naphtho[2,1-b]pyran represented by the following general Formula-(IV) are each as described herein with regard to the indeno[2',3':3,4]naphtho[1,2-b]pyran represented by general formula (III). While indeno-fused naphthopyrans according to the present invention have bonded thereto at least one pendent silane group (e.g., 1 or 2 pendent silane group) represented by general formulas (I) and/or (II), the 3 and 4 positions of the indeno[1',2':4,3]naphtho[2,1-b]pyran represented by general formula (IV) are each typically free of a pendent silane group bonded thereto.

While the indeno-naphthopyran may be selected from one or more indeno[2',2':3,4]naphtho[1,2-b]pyrans represented by general formula (III), and/or one or more indeno[1',2':4,3]naphtho[2,1-b]pyrans represented by general Formula-(IV), it is typically selected from indeno[2',3':3,4]naphtho[1,2-b]pyrans represented by general formula (III).

With the indeno-fused naphthopyrans according to the present invention, for example as represented by general formulas (III) and/or (IV), $R^5$, $R^6$, $R^7$, $R^8$, $R^9$, $R^{10}$, $R^{11}$ and $R^{12}$ may each independently be selected in each case from: a reactive substituent; a compatibilizing substituent; hydrogen; fluoro; chloro; $C_1$-$C_6$ alkyl; $C_3$-$C_7$ cycloalkyl; substituted or unsubstituted phenyl; —$OR_{10}'$ or —$OC(=O)R_{10}'$, wherein $R_{10}'$ is hydrogen, $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$) alkoxy substituted phenyl($C_1$-$C_3$)alkyl, ($C_1$-$C_6$)alkoxy($C_2$-$C_4$)alkyl, $C_3$-$C_7$ cycloalkyl, or mono($C_1$-$C_4$)alkyl substituted $C_3$-$C_7$ cycloalkyl. The phenyl substituents (i.e., the substituents of the substituted phenyl) may be selected from hydroxyl, halogen, carbonyl, $C_1$-$C_6$ alkoxycarbonyl, cyano, halo($C_1$-$C_6$)alkyl, $C_1$-$C_6$ alkyl or $C_1$-$C_6$ alkoxy.

Alternatively or in addition to the previously recited classes and examples, $R^5$, $R^6$, $R^7$, $R^8$, $R^9$, $R^{10}$, $R^{11}$ and $R^{12}$ may each independently be selected in each case from: —$N(R_{11}')R_{12}'$, wherein $R_{11}'$ and $R_{12}'$ are each independently hydrogen, $C_1$-$C_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_8$ alkylaryl, $C_3$-$C_{20}$ cycloalkyl, $C_4$-$C_{20}$ bicycloalkyl, $C_5$-$C_{20}$ tricycloalkyl or $C_1$-$C_{20}$ alkoxyalkyl, wherein said aryl group is phenyl or naphthyl, or $R_{11}'$ and $R_{12}'$ come together with the nitrogen atom to form a $C_3$-$C_{20}$ heterobicycloalkyl ring or a $C_4$-$C_{20}$ hetero-tricycloalkyl ring.

Each $R^5$, $R^6$, $R^7$, $R^8$, $R^9$, $R^{10}$, $R^{11}$ and $R^{12}$ group may independently be selected in each case from, a nitrogen containing ring substituent represented by the following general (or graphic) formula VA:

With the nitrogen ring substituent represented by general formula VA, each —Y— is independently chosen for each occurrence from —$CH_2$—, —$CH(R_{13}')$—, —$C(R_{13}')_2$—, —CH(aryl)-, —$C(aryl)_2$-, and —$C(R_{13}')(aryl)$-, and Z is —Y—, —O—, —S—, —S(O)—, —$SO_2$—, —NH—, —$N(R_{13}')$—, or —N(aryl)-, wherein each $R_{13}'$ is independently $C_1$-$C_6$ alkyl, each aryl is independently phenyl or naphthyl, m is an integer 1, 2 or 3, and p is an integer 0, 1, 2, or 3 and provided that when p is 0, Z is —Y—.

Additionally, each $R^5$, $R^6$, $R^7$, $R^8$, $R^9$, $R^{10}$, $R^{11}$ and $R^{12}$ group may independently be selected in each case from a nitrogen containing ring substituent represented by general formula (VB) and/or general formula (VC):

(VB)

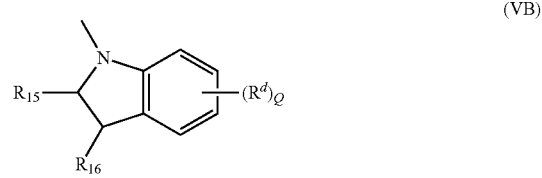

(VC)

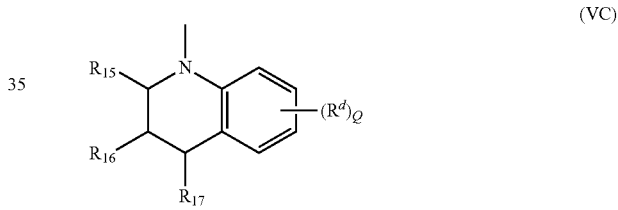

For the nitrogen containing ring substituents represented by general formulas (VB) and (VC), $R_{15}$, $R_{16}$, and $R_{17}$ are each independently selected from hydrogen, $C_1$-$C_6$ alkyl, phenyl, or naphthyl, or the groups $R_{15}$ and $R_{16}$ together form a ring of 5 to 8 carbon atoms and each $R^d$ is independently for each occurrence selected from $C_1$-$C_6$ alkyl, $C_1$-$C_6$ alkoxy, fluoro or chloro, and Q is an integer 0, 1, 2, or 3.

Each $R^5$, $R^6$, $R^7$, $R^8$, $R^9$, $R^{10}$, $R^{11}$ and $R^{12}$ group may also independently be selected in each case from unsubstituted, mono-, or di-substituted $C_4$-$C_{18}$ spirobicyclic amine, or unsubstituted, mono-, and di-substituted $C_4$-$C_{18}$ spirotricyclic amine. The substituents of the spirobicyclic amines and the spirotricyclic amines may in each case be independently selected from aryl, $C_1$-$C_6$ alkyl, $C_1$-$C_6$ alkoxy, or phenyl($C_1$-$C_6$)alkyl.

In an embodiment of the present invention, $R^6$ and $R^7$, of the indeno-fused naphthopyran, may together form a group represented by the following general formula (VD) or general formula (VP), (VD)

-continued

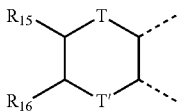
(VE)

With the groups represented by general formulas (VD) and (VE), T and T' are each independently oxygen or the group —NR$_{11}$—, where R$_{11}$, R$_{15}$, and R$_{16}$ are each as set forth and described previously herein.

The R$^{13}$ and R$^{14}$ groups of the indeno-fused naphthopyran according to the present invention, e.g., the indeno[2',3':3,4]naphtho[1,2-b]pyran represented by general formula (III), and/or the indeno[1',2':4,3]naphtho[2,1-b]pyran represented by general formula-(IV), may each be independently selected from: a reactive substituent; a compatibilizing substituent; hydrogen; hydroxy; C$_1$-C$_6$ alkyl; hydroxy(C$_1$-C$_6$)alkyl; C$_3$-C$_7$ cycloalkyl; allyl; substituted or unsubstituted phenyl; substituted or unsubstituted benzyl; chloro; fluoro; the group —C(=O)W', wherein W' is hydrogen, hydroxy, C$_1$-C$_6$ alkyl, C$_1$-C$_6$ alkoxy, the unsubstituted, mono- or di-substituted aryl groups phenyl or naphthyl, phenoxy, mono- or di-(C$_1$-C$_6$) alkoxy substituted phenoxy, mono- or di-(C$_1$-C$_6$)alkoxy substituted phenoxy, amino, mono(C$_1$-C$_6$)alkylamino, di(C$_1$-C$_6$) alkylamino, phenylamino, mono- or di-(C$_1$-C$_6$)alkyl substituted phenylamino, or mono- or di-(C$_1$-C$_6$)alkoxy substituted phenylamino. The phenyl, benzyl, or aryl group substituents (e.g., the substituents of the substituted phenyl, substituted benzyl and substituted aryl groups) are each independently selected from C$_1$-C$_6$ alkyl or C$_1$-C$_6$ alkoxy.

The R$^{13}$ and R$^{14}$ groups of the indeno-fused naphthopyran according to the present invention may each independently also be an —OR$_{18}$ group, in which R$_{18}$ is selected from C$_1$-C$_6$ alkyl, phenyl(C$_1$-C$_3$)alkyl, mono(C$_1$-C$_6$)alkyl substituted phenyl(C$_1$-C$_3$)alkyl, mono(C$_1$-C$_6$)alkoxy substituted phenyl (C$_1$-C$_3$)alkyl, C$_1$-C$_6$ alkoxy(C$_2$-C$_4$)alkyl, C$_3$-C$_7$ cycloalkyl, mono(C$_1$-C$_4$)alkyl substituted C$_3$-C$_7$ cycloalkyl, C$_1$-C$_6$ chloroalkyl, C$_1$-C$_6$ fluoroalkyl, allyl, or the group —CH(R$_{19}$)Y', wherein R$_{19}$ is hydrogen or C$_1$-C$_3$ alkyl and Y' is CN, CF$_3$, or COOR$_{20}$, wherein R$_{20}$ is hydrogen or C$_1$-C$_3$ alkyl, or R$_{18}$ is the group, —C(=O)W'', wherein W'' is hydrogen, C$_1$-C$_6$ alkyl, C$_1$-C$_6$ alkoxy, the unsubstituted, mono- or di-substituted aryl groups phenyl or naphthyl, phenoxy, mono-, or di-(C$_1$-C$_6$)alkyl substituted phenoxy, mono- or di-(C$_1$-C$_6$) alkoxy substituted phenoxy, amino, mono(C$_1$-C$_6$)alkylamino, di(C$_1$-C$_6$)alkylamino, phenylamino, mono- or di-(C$_1$-C$_6$)alkyl substituted phenylamino, or mono- or di-(C$_1$-C$_6$)alkoxy substituted phenylamino. The phenyl, benzyl, or aryl group substituents (e.g., the substituents of the substituted phenyl, substituted benzyl and substituted aryl groups) are each independently selected from C$_1$-C$_6$ alkyl or C$_1$-C$_6$ alkoxy.

The R$^{13}$ and R$^{14}$ groups of the indeno-fused naphthopyran of the present invention may each independently also be a mono-substituted phenyl, in which the phenyl has a substituent located at the para position thereof. The substituent of the mono-substituted phenyl may be: a dicarboxylic acid residue or derivative thereof, a diamine residue or derivative thereof, an amino alcohol residue or derivative thereof, a polyol residue or derivative thereof, —CH$_2$—, —(CH$_2$)$_t$—, or —[O—(CH$_2$)$_t$]$_k$—, in which (t) is selected from an integer of 2, 3, 4, 5 or 6, and k is an integer selected from 1 to 50. The substituent of the mono-substituted phenyl is connected to an aryl group on another photochromic material.

Alternatively, R$^{13}$ and R$^{14}$ may together form an oxo group, a spiro-carbocyclic group containing 3 to 6 carbon atoms, or a spiro-heterocyclic group containing 1 to 2 oxygen atoms and 3 to 6 carbon atoms including the spirocarbon atom. The spiro-carbocyclic and spiro-heterocyclic groups are annellated with 0, 1 or 2 benzene rings.

The B and B' groups of the indeno-fused naphthopyran of the present invention may each be independently selected from: a substituted phenyl; a substituted aryl; a substituted 9-julolidinyl; a substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein the phenyl, aryl, 9-julolidinyl, or heteroaromatic substituent is the reactive substituent R; an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl.

The phenyl, aryl and heteroaromatic substituents (i.e., the substituents of the substituted phenyl, aryl and heteroaromatic groups) of the B and B' groups may each be independently selected from: hydroxyl, a group —C(=O)R$_{21}$, wherein R$_{21}$ is —OR$_{22}$, —N(R$_{23}$)R$_{24}$, piperidino, or morpholino, wherein R$_{22}$ is allyl, C$_1$-C$_6$ alkyl, phenyl, mono(C$_1$-C$_6$)alkyl substituted phenyl, mono(C$_1$-C$_6$)alkoxy substituted phenyl, phenyl(C$_1$-C$_3$)alkyl, mono(C$_1$-C$_6$)alkyl substituted phenyl(C$_1$-C$_3$)alkyl mono(C$_1$-C$_6$)alkoxy substituted phenyl (C$_1$-C$_3$)alkyl, C$_1$-C$_6$ alkoxy(C$_2$-C$_4$)alkyl or C$_1$-C$_6$ haloalkyl, R$_{23}$ and R$_{24}$ are each independently C$_1$-C$_6$ alkyl, C$_5$-C$_7$ cycloalkyl, phenyl or substituted phenyl, the phenyl substituents being C$_1$-C$_6$ alkyl or C$_1$-C$_6$ alkoxy, and said halo substituent is chloro or fluoro, aryl, mono(C$_1$-C$_{12}$)alkoxyaryl, di(C$_1$-C$_{12}$)alkoxyaryl, mono(C$_1$-C$_{12}$)alkylaryl, di(C$_1$-C$_{12}$) alkylaryl, haloaryl, C$_3$-C$_7$ cycloalkylaryl, C$_3$-C$_7$ cycloalkyl, C$_3$-C$_7$ cycloalkyloxy, C$_3$-C$_7$ cycloalkyloxy(C$_1$-C$_{12}$)alkyl, C$_3$-C$_7$ cycloalkyloxy(C$_1$-C$_{12}$)alkoxy, aryl(C$_1$-C$_{12}$)alkyl, aryl (C$_1$-C$_{12}$)alkoxy, aryloxy, aryloxy(C$_1$-C$_{12}$)alkyl, aryloxy(C$_1$-C$_{12}$)alkoxy, mono- or di(C$_1$-C$_{12}$)alkylaryl(C$_1$-C$_{12}$)alkyl, mono- or di-(C$_1$-C$_{12}$)alkoxyaryl(C$_1$-C$_{12}$)alkyl, mono- or di-(C$_1$-C$_{12}$)alkylaryl(C$_1$-C$_{12}$)alkoxy, mono- or di-(C$_1$-C$_{12}$) alkoxyaryl(C$_1$-C$_{12}$)alkoxy, amino, mono- or di-(C$_1$-C$_{12}$) alkylamino, diarylamino, piperazino, N—(C$_1$-C$_{12}$) alkylpiperazino, N-arylpiperazino, aziridino, indolino, piperidino, morpholino, thiomorpholino, tetrahydroquinolino, tetrahydroisoquinolino, pyrrolidyl, C$_1$-C$_{12}$ alkyl, C$_1$-C$_{12}$ haloalkyl, C$_1$-C$_{12}$ alkoxy, mono(C$_1$-C$_{12}$)alkoxy(C$_1$-C$_{12}$)alkyl, acryloxy, methacryloxy, or halogen.

The B and B' groups may also each independently be an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl. The substituents of these mono-substituted groups are each independently selected from C$_1$-C$_{12}$ alkyl, C$_1$-C$_{12}$ alkoxy, phenyl, or halogen.

In addition, the B and B' groups may each be independently selected from a group represented by the following general formulas (VIA) or (VIB),

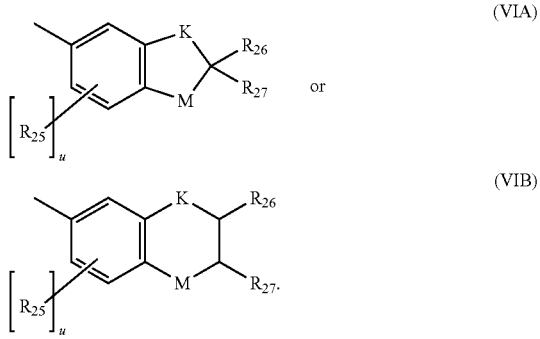

Independently with each of general formulas (VIA) and (VIB), K is —CH$_2$— or —O—, and M is —O— or substituted nitrogen, provided that when M is substituted nitrogen, K is —CH$_2$—. The substituted nitrogen substituents are hydrogen, C$_1$-C$_{12}$ alkyl, or C$_1$-C$_{12}$ acyl. Each R$_{25}$ is independently selected for each occurrence from C$_1$-C$_{12}$ alkyl, C$_1$-C$_{12}$ alkoxy, hydroxy, and halogen, and each u is independently an integer ranging from 0 to 2. The R$_{26}$ and R$_{27}$ groups are each independently hydrogen or C$_1$-C$_{12}$ alkyl.

Each B and B' group may independently be a group represented by the following general formula (VII),

With the group represented by general formula (VII), R$_{28}$ is hydrogen or C$_1$-C$_{12}$ alkyl, and R$_{29}$ is an unsubstituted, mono- or di-substituted group chosen from naphthyl, phenyl, furanyl, and thienyl. The substitutents of the mono- or di-substituted naphthyls, phenyls, furanyls, and thienyls, are in each case independently selected from C$_1$-C$_{12}$ alkyl, C$_1$-C$_{12}$ alkoxy, or halogen.

The B and B' groups may together form a member selected from, a fluoren-9-ylidene, a mono-substituted fluoren-9-ylidene, or a di-substituted fluoren-9-ylidene. The substituents of the mono-substituted fluoren-9-ylidene, and the di-substituted fluoren-9-ylidene may in each case be independently selected from C$_1$-C$_{12}$ alkyl, C$_1$-C$_{12}$ alkoxy, or halogen.

As discussed previously herein, the indeno-fused naphthopyrans of the photochromic material according to the present invention, for example as represented by general formulas (III) and/or (IV): (a) at least one of R$^5$, R$^6$, R$^7$, R$^8$, R$^9$, R$^{10}$, R$^{11}$, R$^{12}$, R$^{13}$ and R$^{14}$ is a pendent silane group represented by formula (I) and/or formula (II), as described previously herein; and/or (b) at least one of B and B' has bonded thereto at least one pendent silane group represented by formula (I) and/or formula (II). Typically, at least one and, at the same time, less than all available positions of the indeno-fused naphthopyran have a pendent silane group bonded thereto. In an embodiment, for example, the indeno-fused naphthopyran of the photochromic material according to the present invention has bonded thereto 1 or 2 pendent silane groups represented by formula (I) and/or formula (II).

In an embodiment, with the indeno-fused naphthopyran of the photochromic material of the present invention: (i) at least one of R$^{11}$, R$^{13}$ and R$^{14}$ is a pendent silane group represented by formulas (I) and/or (II); and/or (ii) at least one of B and B' has bonded thereto at least one pendent silane group, represented by formulas (I) and/or (II). The indeno-fused naphthopyran typically has bonded thereto 1 or 2 of such pendent silane groups.

In a particular embodiment the indeno-fused naphthopyran has bonded thereto one (i.e., a single) pendent silane group represented by general formula (I) or (II). More particularly, with the indeno-fused naphthopyran of this embodiment: the R$^{11}$ group is the pendent silane group; R$^5$, R$^8$, R$^9$, R$^{10}$ and R$^{12}$ are each hydrogen; R$^6$ and R$^7$ are each independently selected from hydrogen, linear or branched C$_1$-C$_6$ alkyl, and —OR$_{10'}$ where R$_{10'}$ is C$_{1-6}$ alkyl; R$^{13}$ and R$^{14}$ are each independently selected from linear or branched C$_1$-C$_6$ alkyl, and C$_3$-C$_7$ cycloalkyl; and B and B' are each independently selected from aryl substituted with C$_1$-C$_6$ alkoxy, and aryl substituted with morpholino.

In a further embodiment, the indeno-fused naphthopyran has bonded thereto one (i.e., a single) pendent silane group represented by general formula (I) or (II), and, in particular, the R$^{13}$ group thereof is the pendent silane group. The remaining groups of the indeno-fused naphthopyran, in which R$^{13}$ is a pendent silane group are described as follows: R$^5$, R$^8$, R$^9$, R$^{10}$ and R$^{12}$ are each hydrogen; R$^6$ and R$^7$ are each independently selected from hydrogen, C$_1$-C$_6$ alkyl, and —OR$_{10'}$ where R$_{10'}$ is C$_{1-6}$ alkyl, R$^{11}$ is selected from hydrogen, halogen (e.g., fluoro, chloro, bromo or iodo), and C$_1$-C$_6$ alkyl; R$^{14}$ is selected from C$_1$-C$_6$ alkyl, and C$_3$-C$_7$ cycloalkyl; and B and B' are each independently selected from aryl substituted with C$_1$-C$_6$ alkoxy, and aryl substituted with morpholino.

A non-limiting example of an indeno-fused naphthopyran according to the present invention in which the R$^{13}$ group is the pendent silane group, as described above, is represented by the following general formula 20b.

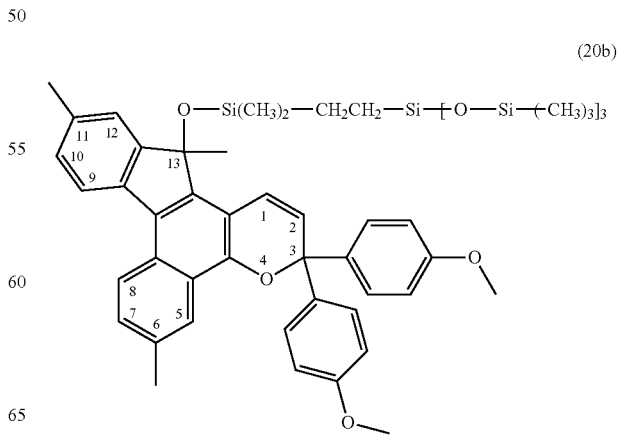

In general formula (20b), the $R^{13}$ group is a pendent silane group represented by general formula (I) in which, m is 0, n is 3, Z is Si, each $R_1$ is methyl, and L is a divalent linking group represented by general formula (5a), —O—Si(CH$_3$)$_2$—CH$_2$CH$_2$—. (5a)

With further reference to general formula (20b), $R^5$, $R^7$, $R^8$, $R^9$, $R^{10}$ and $R^{12}$ are each hydrogen; $R^6$, $R^{11}$ and $R^{14}$ are each methyl; and B and B' are each a phenyl group substituted with a methoxy group.

A further example of an indeno-fused naphthopyran according to the present invention in which the $R^{13}$ group is the pendent silane group, as described above, is represented by the following general formula 20c.

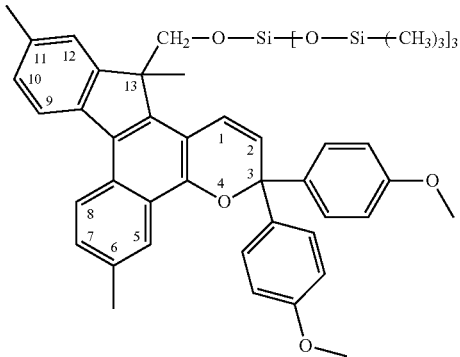

(20c)

In general formula (20c), the $R^{13}$ group is a pendent silane group represented by general formula (I) in which, m is 0, n is 3, Z is Si, each $R_1$ is methyl, and L is a divalent linking group represented by general formula (3a), —CH$_2$—O—. (3a)

With further reference to general formula (20c), $R^5$, $R^7$, $R^8$, $R^9$, $R^{10}$ and $R^{12}$ are each hydrogen; $R^6$, $R^{11}$ and $R^{14}$ are each methyl; and B and B' are each a phenyl group substituted with a methoxy group.

Another non-limiting example of an indeno-fused naphthopyran according to the present invention in which the $R^{13}$ group is the pendent silane group, as described above, is represented by the following general formula 20d.

In general formula (20d), the $R^{13}$ group is a pendent silane group represented by general formula (II) in which, t is 0, y is 3, m is 1, n is 2, Z is Si, R is methyl, each $R_1$ is methyl, $R^a$ is —CH$_2$CH$_2$—, and L is a divalent linking group represented by general formula (1a), —O—(CH$_2$CH$_2$O)$_3$—. (1a)

With further reference to general formula (20d), $R^5$, $R^7$, $R^8$, $R^9$, $R^{10}$ and $R^{12}$ are each hydrogen; $R^6$, $R^{11}$ and $R^{14}$ are each methyl; and B and B' are each a phenyl group substituted with a methoxy group.

In an embodiment of the present invention, the indeno-fused naphthopyran has bonded thereto one (i.e., a single) pendent silane group represented by general formula (I) or (II), and in particular, B or B' has the pendent silane group bonded thereto.

With regard to this particular embodiment, the various groups of the indeno-fused naphthopyran, in which B or B' has a pendent silane group bonded thereto are described as follows: $R^5$, $R^8$, $R^9$, $R^{10}$ and $R^{12}$ are each hydrogen; $R^6$ and $R^7$ are each independently selected from hydrogen, halogen, $C_1$-$C_6$ alkyl, and —OR$_{10'}$ where $R_{10'}$ is $C_1$-$C_6$ alkyl, $R^{11}$ is selected from hydrogen, halogen, and $C_1$-$C_6$ alkyl; $R^{13}$ and $R^{14}$ are each independently selected from $C_1$-$C_6$ alkyl, and $C_3$-$C_7$ cycloalkyl; and B and B' are each independently selected from aryl, aryl substituted with $C_1$-$C_6$ alkoxy, aryl substituted with morpholino and aryl substituted with piperidinyl.

A non-limiting example of an indeno-fused naphthopyran according to the present invention in which B or B' has a pendent silane group bonded thereto, as described above, is represented by the following general formula 20e.

(20e)

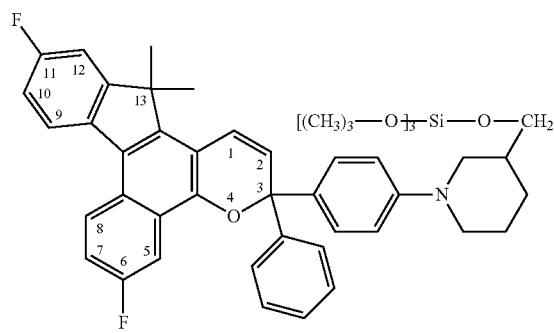

(20d)

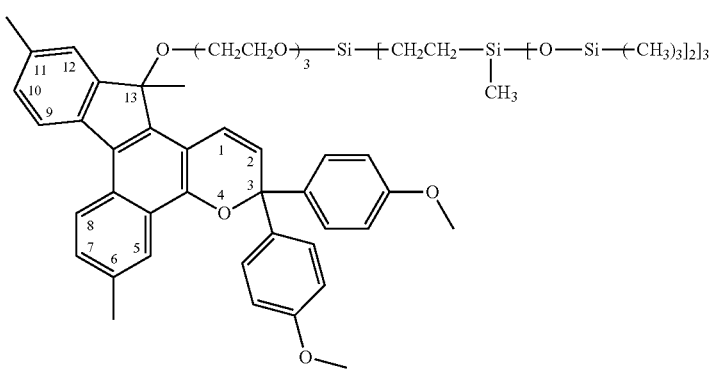

In general formula (20e), the B group (or substituent) has bonded thereto a pendent silane group represented by general formula (I) in which, m is 0, n is 3, Z is Si, each $R_1$ is methyl, and L is a divalent linking group represented by general formula (3a),

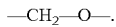  (3a)

With further reference to general formula (20e), $R^5$, $R^7$, $R^8$, $R^9$, $R^{10}$ and $R^{12}$ are each hydrogen; $R^6$ and $R^{11}$ are each fluoro; $R^{13}$ and $R^{14}$ are each methyl; B is a phenyl group substituted with a piperidinyl group; and B' is a phenyl group. The pendent silane group represented by general formula (I) is bonded to the piperidinyl group of the piperidinyl substituted phenyl that is the B group in this particular embodiment.

A further non-limiting example of an indeno-fused naphthopyran according to the present invention in which B or B' has a pendent silane group bonded thereto, as described above, is represented by the following general formula 20f.

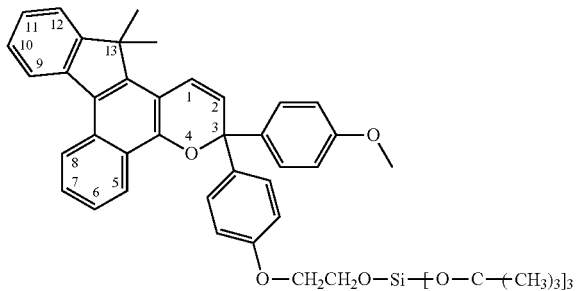  (20f)

In general formula (20f), the B group (or substituent) has bonded thereto a pendent silane group represented by general formula (I) in which, m is 0, n is 3, Z is Si, each $R_1$ is methyl, and L is a divalent linking group represented by the following general formula,

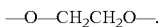

With further reference to general formula (20f), $R^5$, $R^6$, $R^7$, $R^8$, $R^9$, $R^{10}$, $R^{11}$ and $R^{12}$ are each hydrogen; $R^{13}$ and $R^{14}$ are each methyl; B' is a phenyl group substituted with a methoxy group; and B is a phenyl group. The pendent silane group represented by general formula (I) is bonded to the piperidinyl group of the piperidinyl substituted phenyl that is the B group in this particular embodiment.

In an embodiment of the present invention, the indeno-fused naphthopyran has bonded thereto two pendent silane groups represented by general formula (I) or (II), and in particular, B and B' each have a pendent silane group bonded thereto. With regard to this particular embodiment, the various groups of the indeno-fused naphthopyran, in which B and B' each have a pendent silane group bonded thereto are described as follows: $R^5$, $R^8$, $R^9$, $R^{10}$ and $R^{12}$ are each hydrogen;

$R^6$ and $R^7$ are each independently selected from hydrogen, halogen, $C_1$-$C_6$ alkyl, and —$OR_{10'}$ where $R_{10'}$ is $C_1$-$C_6$ alkyl; $R^{11}$ is selected from hydrogen, halogen (e.g., fluoro, chloro, bromo or iodo), and $C_1$-$C_6$ alkyl; $R^{13}$ and $R^{14}$ are each independently selected from $C_1$-$C_6$ alkyl, and $C_3$-$C_7$ cycloalkyl; and B and B' are each independently selected from aryl, aryl substituted with $C_1$-$C_6$ alkoxy, aryl substituted with morpholino and aryl substituted with piperidinyl.

A non-limiting example of an indeno-fused naphthopyran according to the present invention in which B and B' each have a pendent silane group bonded thereto, as described above, is represented by the following general formula 20g.

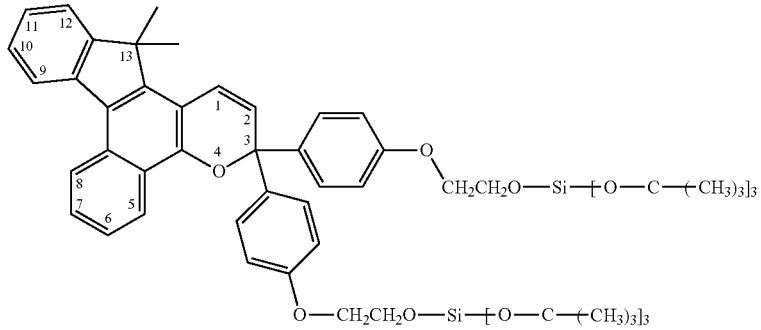  (20g)

In general formula (20g), B and B' each have bonded thereto a pendent silane group represented by general formula (I) in which and in each case, m is 0, n is 3, Z is Si, each $R_1$ is methyl, and L is a divalent linking group represented by the following general formula,

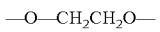

With further reference to general formula (20g), $R^5$, $R^6$, $R^7$, $R^8$, $R^9$, $R^{10}$, $R^{11}$ and $R^{12}$ are each hydrogen; $R^{13}$ and $R^{14}$ are each methyl; B and B' are each a phenyl group. Each pendent silane group represented by general formula (I) is bonded to the phenyl group of each B and B'.

As previously discussed, the indeno-fused naphthopyrans according to present invention may include at least one of a reactive substituent and/or a compatibilizing substituent. Any one or more of the groups $R^5$ through $R^{14}$, B and B' of the indeno-fused naphthopyran (e.g., represented by general formulas-III and/or -IV) may include at least one of a reactive substituent and/or a compatibilizing substituent. If the photochromic compound includes multiple reactive substituents and/or multiple compatibilizing substituents, each reactive substituent and each compatibilizing substituent may be independently chosen.

The reactive substituent and the compatibilizing substituent may each independently be represented in each case by one of:
-A'-D-E-G-J (XIII); -G-E-G-J (XVI); -D-E-G-J (XIX);
-A'-D-J (XIV); -D-G-J (XVII); -D-J (XX);
-A'-G-J (XV); -G-J (XVIII); and -A'-J (XXI).

With formulas (XIII) through (XXI), non-limiting examples of groups that -A'- may represent according to various non-limiting embodiments disclosed herein include —O—, —C(=O)—, —CH₂—, —OC(=O)— and —NHC(=O)—, provided that if -A' represents —O—, -A'- forms at least one bond with -J.

Non-limiting examples of groups that -D- may represent according to various non-limiting embodiments include a diamine residue or a derivative thereof, wherein a first amino nitrogen of said diamine residue may form a bond with -A'-, the group that extends the pi-conjugated system of the indeno-fused naphthopyran bonded at the 11-position thereof, or a substituent or an available position on the indeno-fused naphthopyran, and a second amino nitrogen of said diamine residue may form a bond with -E-, -G- or -J; and an amino alcohol residue or a derivative thereof, wherein an amino nitrogen of said amino alcohol residue may form a bond with -A'-, the group that extends the pi-conjugated system of the indeno-fused naphthopyran bonded at the 11-position thereof, or a substituent or an available position on the indeno-fused naphthopyran, and an alcohol oxygen of said amino alcohol residue may form a bond with -E-, -G- or -J. Alternatively, according to various non-limiting embodiments disclosed herein the amino nitrogen of said amino alcohol residue may form a bond with -E-, -G- or -J, and said alcohol oxygen of said amino alcohol residue may form a bond with -A'-, the group that extends the pi-conjugated system of the indeno-fused naphthopyran bonded at the 11-position thereof, or a substituent or an available position on the indeno-fused naphthopyran.

Non-limiting examples of suitable diamine residues that -D- may represent include an aliphatic diamine residue, a cyclo aliphatic diamine residue, a diazacycloalkane residue, an azacyclo aliphatic amine residue, a diazacrown ether residue, and an aromatic diamine residue. More particular, illustrative and non-limiting examples of diamine residues that may be used in conjunction with various non-limiting embodiments disclosed herein include the following:

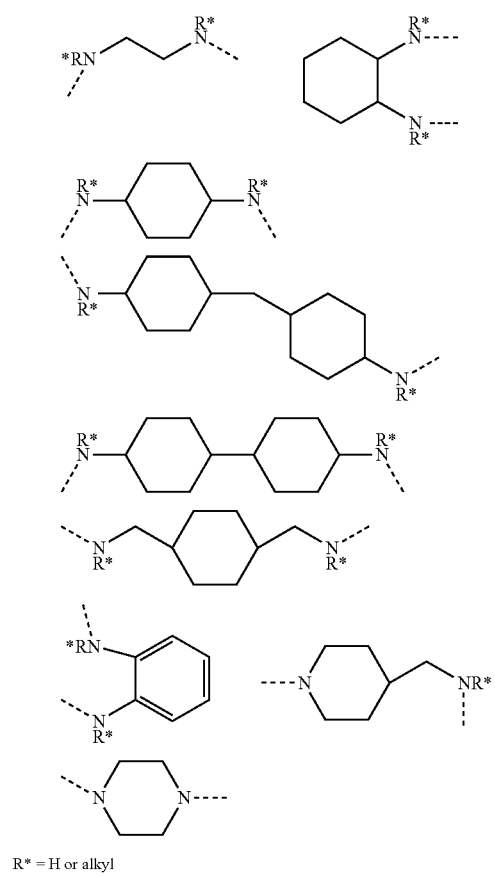

R* = H or alkyl

Non-limiting examples of suitable amino alcohol residues that -D- may represent include an aliphatic amino alcohol residue, a cyclo aliphatic amino alcohol residue, an azacyclo aliphatic alcohol residue, a diazacyclo aliphatic alcohol residue and an aromatic amino alcohol residue. More particular, illustrative and non-limiting examples of amino alcohol residues that may be used in conjunction with various non-limiting embodiments disclosed herein include the following:

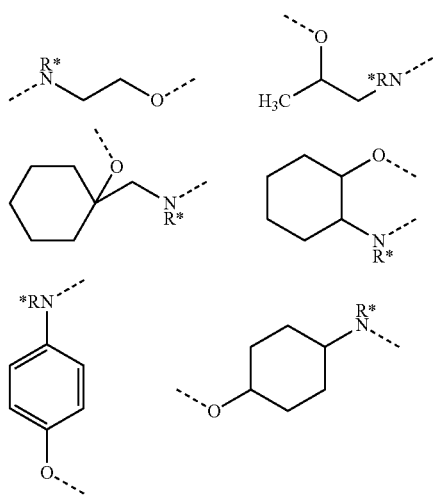

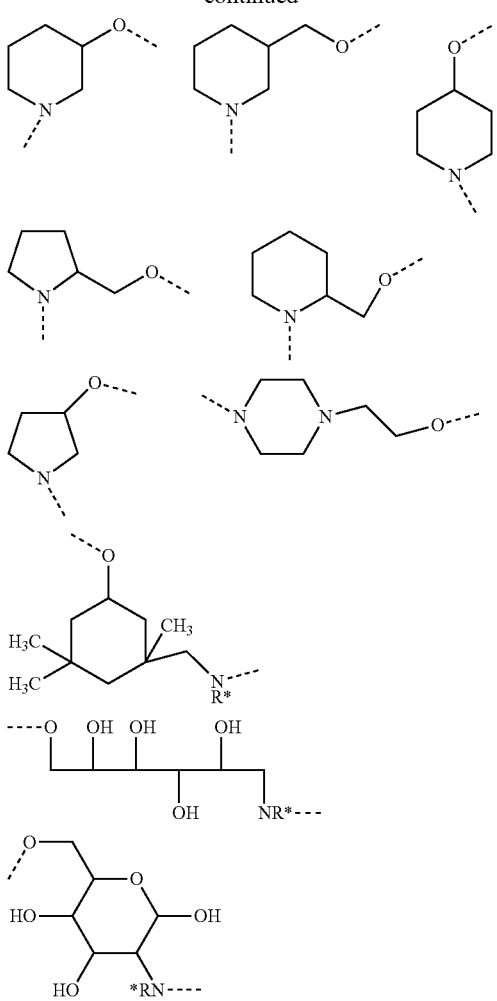

R* = H, alkyl

With continued reference to formulas (XIII) through (XXI) above, according to various non-limiting embodiments disclosed herein, -E- may represent a dicarboxylic acid residue or a derivative thereof, wherein a first carbonyl group of said dicarboxylic acid residue may form a bond with -G- or -D-, and a second carbonyl group of said dicarboxylic acid residue may form a bond with -G-. Non-limiting examples of suitable dicarboxylic acid residues that -E- may represent include an aliphatic dicarboxylic acid residue, a cycloaliphatic dicarboxylic acid residue and an aromatic dicarboxylic acid residue. More particular, illustrative and non-limiting examples of dicarboxylic acid residues that may be used in conjunction with various non-limiting embodiments disclosed herein include the following:

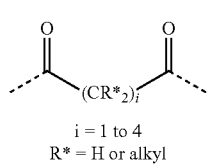

i = 1 to 4
R* = H or alkyl

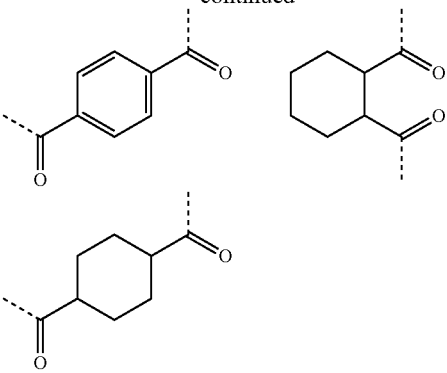

According to various non-limiting embodiments disclosed herein, -G- may represent a group represented by the following general formula, $$-[(OC_2H_4)_x(OC_3H_6)_y(OC_4H_8)_z]-O-$$

in which x, y and z are each independently chosen and range from 0 to 50, and a sum of x, y, and z ranges from 1 to 50; a polyol residue or a derivative thereof, wherein a first polyol oxygen of said polyol residue may form a bond with -A'-, -D-, -E-, or a substituent or an available position on the indeno-fused naphthopyran, and a second polyol oxygen of said polyol may form a bond with -E- or -J; or a combination thereof, wherein the first polyol oxygen of the polyol residue forms a bond with a group $[(OC_2H_4)_x(OC_3H_6)_y(OC_4H_8)_z]-$ (i.e., to form the group $[(OC_2H_4)_x(OC_3H_6)_y(OC_4H_8)_z]-O-$), and the second polyol oxygen forms a bond with -E- or -J. Non-limiting examples of suitable polyol residues that -G- may represent include an aliphatic polyol residue, a cyclo aliphatic polyol residue and an aromatic polyol residue.

More particular, illustrative and non-limiting examples of polyols from which the polyol residues that -G- may represent may be formed according to various non-limiting embodiments disclosed herein include (a) low molecular weight polyols having an average molecular weight less than 500, such as, but not limited to, those set forth in U.S. Pat. No. 6,555,028 at col. 4, lines 48-50, and col. 4, line 55 to col. 6, line 5, which disclosure is hereby specifically incorporated by reference herein; (b) polyester polyols, such as, but not limited to, those set forth in U.S. Pat. No. 6,555,028 at col. 5, lines 7-33, which disclosure is hereby specifically incorporated by reference herein; (c) polyether polyols, such as but not limited to those set forth in U.S. Pat. No. 6,555,028 at col. 5, lines 34-50, which disclosure is hereby specifically incorporated by reference herein; (d) amide-containing polyols, such as, but not limited to, those set forth in U.S. Pat. No. 6,555,028 at col. 5, lines 51-62, which disclosure is hereby specifically incorporated by reference; (e) epoxy polyols, such as, but not limited to, those set forth in U.S. Pat. No. 6,555,028 at col. 5 line 63 to col. 6, line 3, which disclosure is hereby specifically incorporated by reference herein; (f) polyhydric polyvinyl alcohols, such as, but not limited to, those set forth in U.S. Pat. No. 6,555,028 at col. 6, lines 4-12, which disclosure is hereby specifically incorporated by reference herein; (g) urethane polyols, such as, but not limited to those set forth in U.S. Pat. No. 6,555,028 at col. 6, lines 13-43, which disclosure is hereby specifically incorporated by reference herein; (h) polyacrylic polyols, such as, but not limited to those set forth in U.S. Pat. No. 6,555,028 at col, 6, lines 43 to col. 7, line 40, which disclosure is hereby specifically incorporated by reference herein; (i) polycarbonate polyols, such as, but not limited to, those set forth in U.S. Pat. No.

6,555,028 at col. 7, lines 41-55, which disclosure is hereby specifically incorporated by reference herein; and (j) mixtures of such polyols.

With further reference to formulas (XIII) through (XXI), according to various non-limiting embodiments disclosed herein, -J may represent a group -K, wherein -K represents a group such as, but not limited to, —CH$_2$COOH, —CH(CH$_3$)COOH, —C(O)(CH$_2$)$_w$COOH, —C$_6$H$_4$SO$_3$H, —C$_5$H$_{10}$SO$_3$H, —C$_4$H$_8$SO$_3$H, —C$_3$H$_6$SO$_3$H, —C$_2$H$_4$SO$_3$H and —SO$_3$H, wherein "w" ranges from 1 to 18. According to other non-limiting embodiments -J may represent hydrogen that forms a bond with an oxygen or a nitrogen of linking group to form a reactive moiety such as —OH or —NH, For example, according to various non-limiting embodiments disclosed herein, -J may represent hydrogen, provided that if -J represents hydrogen, -J is bonded to an oxygen of -D- or -G-, or a nitrogen of -D-.

According to still further non-limiting embodiments, -J may represent a group -L or residue thereof, wherein -L may represent a reactive moiety. For example, according to various non-limiting embodiments disclosed herein -L may represent a group such as, but not limited to, acryl, methacryl, crotyl, 2-(methacryloxy)ethylcarbamyl, 2-(methacryloxy)ethoxycarbonyl, 4-vinylphenyl, vinyl, 1-chlorovinyl or epoxy. As used herein, the terms acryl, methacryl, crotyl, 2-(methacryloxy)ethylcarbamyl, 2-(methacryloxy)ethoxycarbonyl, 4-vinylphenyl, vinyl, 1-chlorovinyl, and epoxy refer to the following structures:

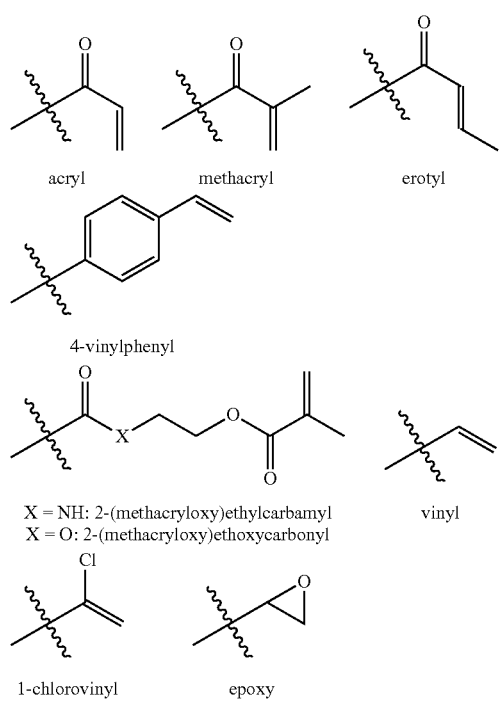

As previously discussed, -G- may represent a residue of a polyol, which is defined herein to include hydroxy-containing carbohydrates, such as those set forth in U.S. Pat. No. 6,555,028 at col. 7, line 56 to col. 8, line 17, which disclosure is hereby specifically incorporated by reference herein. The polyol residue may be formed, for example and without limitation herein, by the reaction of one or more of the polyol hydroxyl groups with a precursor of -A'-, such as a carboxylic acid or a methylene halide, a precursor of polyalkoxylated group, such as polyalkylene glycol, or a hydroxyl substituent of the indeno-fused naphthopyran. The polyol may be represented by q-(OH)$_a$ and the residue of the polyol may be represented by the formula —O-q-(OH)$_{n-1}$, wherein q is the backbone or main chain of the polyhydroxy compound and "a" is at least 2.

Further, as discussed above, one or more of the polyol oxygens of -G- may form a bond with -J (i.e., forming the group -G-J). For example, although not limiting herein, wherein the reactive and/or compatibilizing substituent comprises the group -G-J, if -G- represents a polyol residue and -J represents a group -K that contains a carboxyl terminating group, -G-J may be produced by reacting one or more polyol hydroxyl groups to form the group -K (for example as discussed with respect to Reactions B and C at col. 13, line 22 to col. 16, line 15 of U.S. Pat. No. 6,555,028, which disclosure is hereby specifically incorporated by reference herein) to produce a carboxylated polyol residue. Alternatively, if -J represents a group -K that contains a sulfo or sulfono terminating group, although not limiting herein, -G-J may be produced by acidic condensation of one or more of the polyol hydroxyl groups with HOC$_6$H$_4$SO$_3$H; HOC$_5$H$_{10}$SO$_3$H; HOC$_4$H$_8$SO$_3$H; HOC$_3$H$_6$SO$_3$H; HOC$_2$H$_4$SO$_3$H; or H$_2$SO$_4$, respectively. Further, although not limiting herein, if -G- represents a polyol residue and -J represents a group -L chosen from acryl, methacryl, 2-(methacryloxy)ethylcarbamyl and epoxy, -L may be added by condensation of the polyol residue with acryloyl chloride, methacryloyl chloride, 2-isocyanatoethyl methacrylate or epichlorohydrin, respectively.

Figure 2:
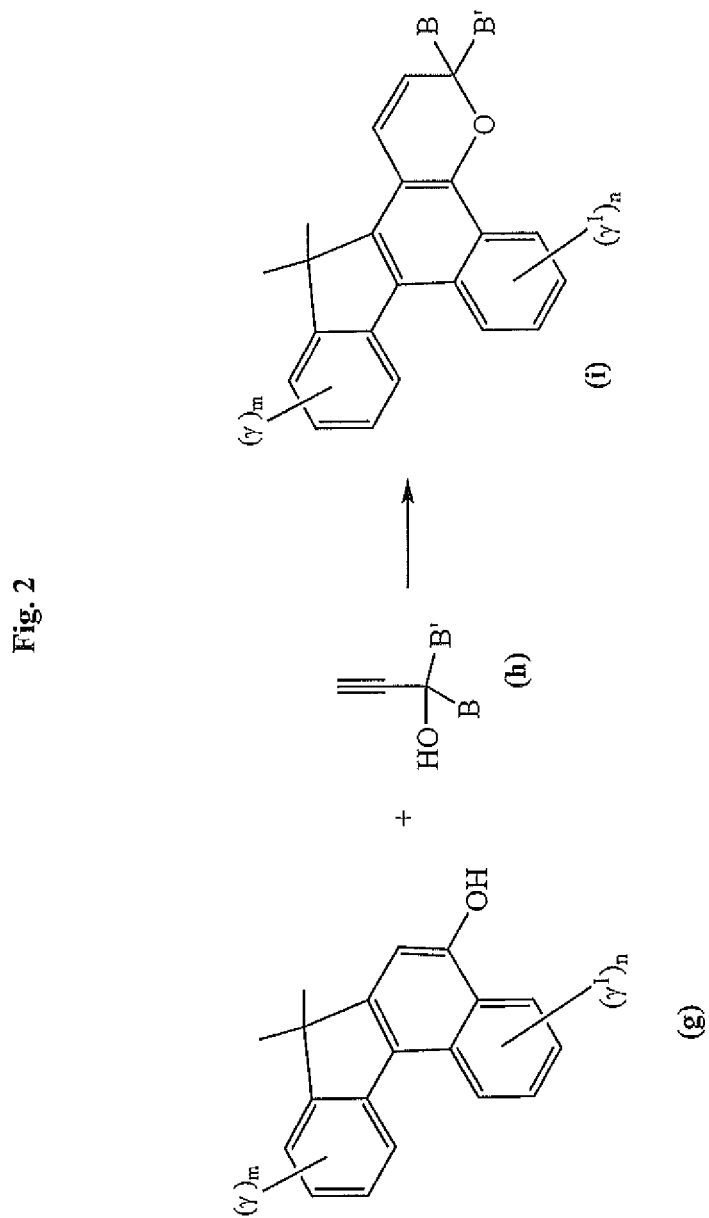
FIG. 2 is a representative schematic diagram of a synthetic reaction scheme depicting the preparation of an indeno-fused naphthopyran to which a pendent silane group may be bonded to form a photochromic compound according to the present invention.

Methods of synthesizing the photochromic compounds according to the present invention that include indeno-fused naphthopyrans are described here with reference to the general reaction schemes summarized and depicted in FIGS. 1 through 12 of the drawings. With reference to FIG. 1, there is depicted a reaction scheme for making substituted 7H-benzo[C]fluoren-5-ol compounds, that may be further reacted as shown in FIG. 2 to form indeno-fused naphthopyrans to which may be bonded pendent silane groups represented by formulas (I) and/or (II) so as to form the photochromic compounds of the photochromic materials according to the present invention.

The synthetic reaction schemes depicted in FIGS. 1-12 are presented for purposes of illustration, and as such are not intended to be limiting with regard to the scope of the present invention.

With reference to FIG. 1, a solution of benzoyl chloride that may have one or more γ-substituents, represented by structure (a) in FIG. 1, and benzene, represented by structure (b) in FIG. 1, which may have one or more γ$^1$-substituents, in methylene chloride are added to a reaction flask. Suitable γ-substituents include, for example those groups as described previously herein with regard to R$^9$, R$^{10}$, R$^{11}$ and R$^{12}$, depending on what position a particular γ-substituent is bonded to, or a precursor thereof (e.g., a halogen group that may be later substituted with a group that may optionally be further modified). Suitable γ$^1$-substituents include, for example and without limitation, those groups as described previously herein with regard to R$^5$, R$^6$, R$^7$ and R$^8$, depending on what position a particular γ$^1$-substituent is bonded to, or a precursor thereof (e.g., a halogen group that may be later substituted with a group that may optionally be further modified). The subscripts n and m may each be independently selected from 0 to 4. Anhydrous aluminum chloride catalyzes the Friedel-Crafts acylation to give an optionally substituted benzophenone represented by structure (c) in FIG. 1. This material is then reacted via a Stobbe reaction with dimethyl succinate to produce a mixture of half-esters, one of which is represented by structure (d) in FIG. 1. Thereafter the half-esters are reacted in acetic anhydride and toluene at an elevated temperature to produce, after recrystallization, a mixture of optionally substituted naphthalene compounds, one of which is represented by structure (e) in FIG. 1. The mixture of optionally substituted naphthalene compounds is then reacted with methyl magnesium chloride to produce a mixture of optionally substituted naphthalene compounds, one of which is represented by structure (f) in FIG. 1. The mixture of optionally substituted naphthalene compounds is then cyclized with dodecylbenzene sulfonic acid to provide a mixture of 7H-benzo[C]fluoren-5-ol compounds, one of which is represented by structure (g) in FIG. 1.

As depicted in FIG. 2, the 7H-benzo[C]fluoren-5-ol compound represented by structure (g) may be reacted with a propargyl alcohol represented by structure (h) to produce the indeno-fused naphthopyran represented by structure (i) in FIG. 2.

Further, non-limiting examples of methods of forming benzofurano-fused naphthopyrans, indolo-fused naphthopyrans, and/or benzothieno-fused naphthopyrans that may be useful (with appropriate modifications that will be recognized by skilled artisans) in forming the benzofurano-fused naphthopyrans, indolo-fused naphthopyrans and/or benzothieno-fused naphthopyrans according to various non-limiting embodiments disclosed herein are set forth in U.S. Pat. No. 5,651,923 at col. 6, line 43 to col. 13, line 48, which disclosure is hereby specifically incorporated by reference herein; U.S. Pat. No. 6,018,059 at column 6, line 1, to column 7, line 64, which disclosure is hereby specifically incorporated by reference herein; and U.S. Pat. No. 6,392,043 at column 6, line 5, to column 10, line 10, which disclosure is hereby specifically incorporated by reference herein.

Figure 3:
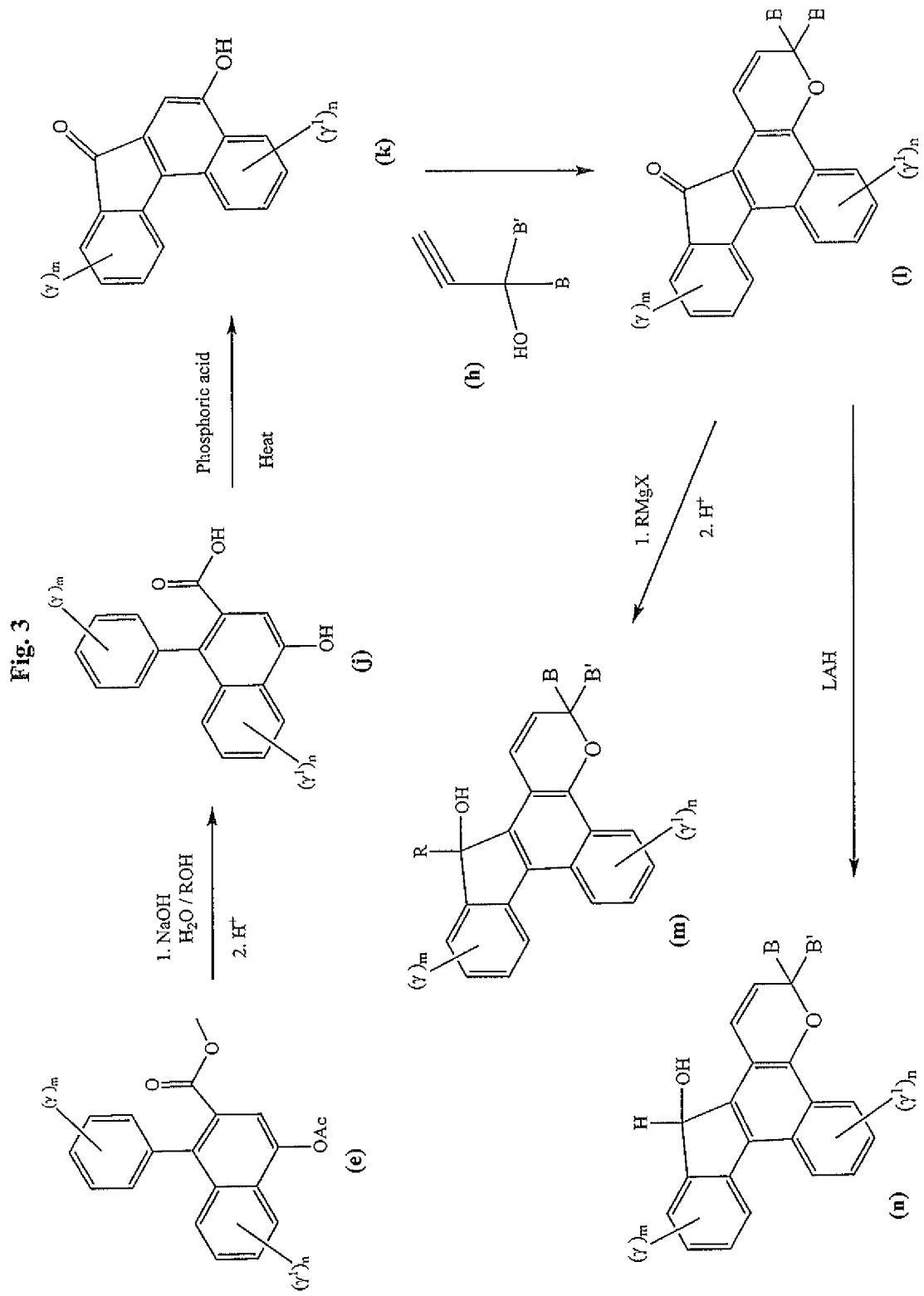
FIG. 3 is a representative schematic diagram of a synthetic reaction scheme depicting the preparation of indeno-fused naphthopyrans having a hydroxyl group at Position-13 thereof, to which a pendent silane group may be bonded to from a photochromic compound according to the present invention.

The preparation of an indeno-fused naphthopyran having a hydroxyl group at Position-13 is described with reference to FIG. 3. The optionally substituted naphthalene compound represented by structure (e) of FIG. 1 is reacted with sodium hydroxide in the presence of water and alcohol, and then acid to form the hydroxyl and carboxylic acid functional compound represented by structure (j), which is then reacted with phosphoric acid under conditions of elevated temperature to form the cyclic fused ring ketone represented by structure (k). The cyclic fused ring ketone represented by structure (k) is then reacted with a propargyl alcohol represented by structure (h) to produce the ketone intermediate represented by structure (l), which may be reacted with Grignard reagent to produce the indeno-fused naphthopyran represented by structure (m), which has at Position-13: a hydroxyl group; and an R-group, which is a residue of the Grignard reagent. Alternatively, the ketone intermediate represented by structure (l), may be reacted with lithium aluminum hydride (LAH) to form the indeno-fused naphthopyran represented by structure (n), which has at Position-13: a hydroxyl group; and a hydrogen.

Figure 4:
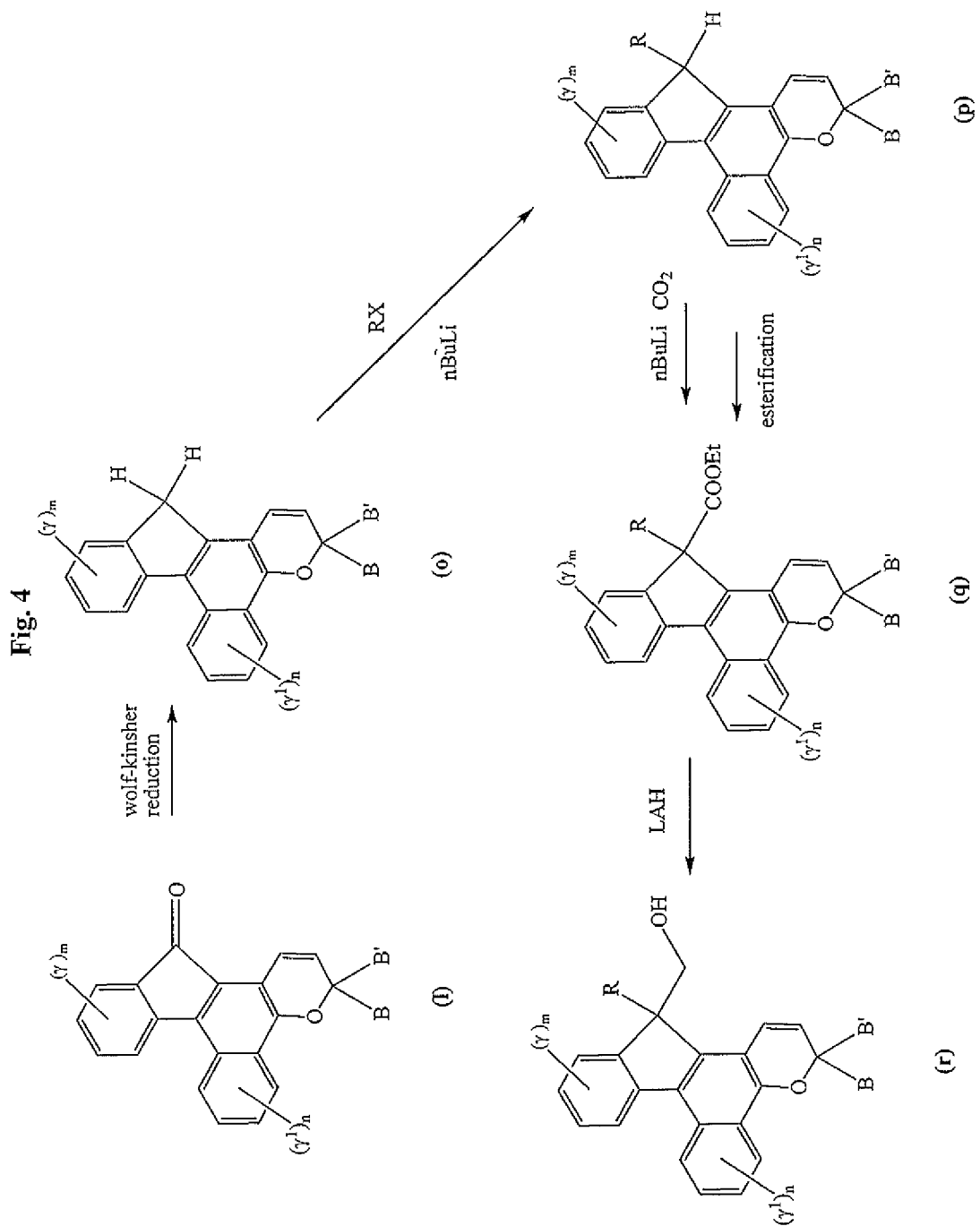
FIG. 4 is a representative schematic diagram of a synthetic reaction scheme depicting the preparation of an indeno-fused naphthopyran having a methylenol group at Position-13 thereof, to which a pendent silane group may be bonded to from a photochromic compound according to the present invention.

The preparation of an indeno-fused naphthopyran having a methylol group ($-CH_2-OH$) at Position-13 is described with reference to FIG. 4. The ketone intermediate represented by structure (I) of FIG. 3 is converted by means of Wolf-Kinsher reduction to the indeno-fused naphthopyran represented by structure (O), which has two hydrogens at Position-13 thereof. The indeno-fused naphthopyran represented by structure (O) is reacted with a halohydrocarbyl represented by RX, which is typically an alkylhalo, in the presences of n-butyl lithium to form the indeno-fused naphthopyran represented by structure (p), in which one of the Position-13 hydrogens has been substituted with the R-group of the RX reactant. The remaining Position-13 hydrogen of the indeno-fused naphthopyran represented by structure (p) is then converted to a carboxylic acid group by exposure to n-butyl lithium in the present of $CO_2$, followed by an esterification reaction to form the indeno-fused naphthopyran represented by structure (q) having a carboxylic acid ester group at Position-13. The Position-13 carboxylic acid ester of the indeno-fused naphthopyran represented by structure (q) is reduced in the presence of lithium aluminum hydride (LAH) to form the indeno-fused naphthopyran represented by structure (r), which has a methylol group ($-CH_2-OH$) at Position-13 thereof.

Figure 5:
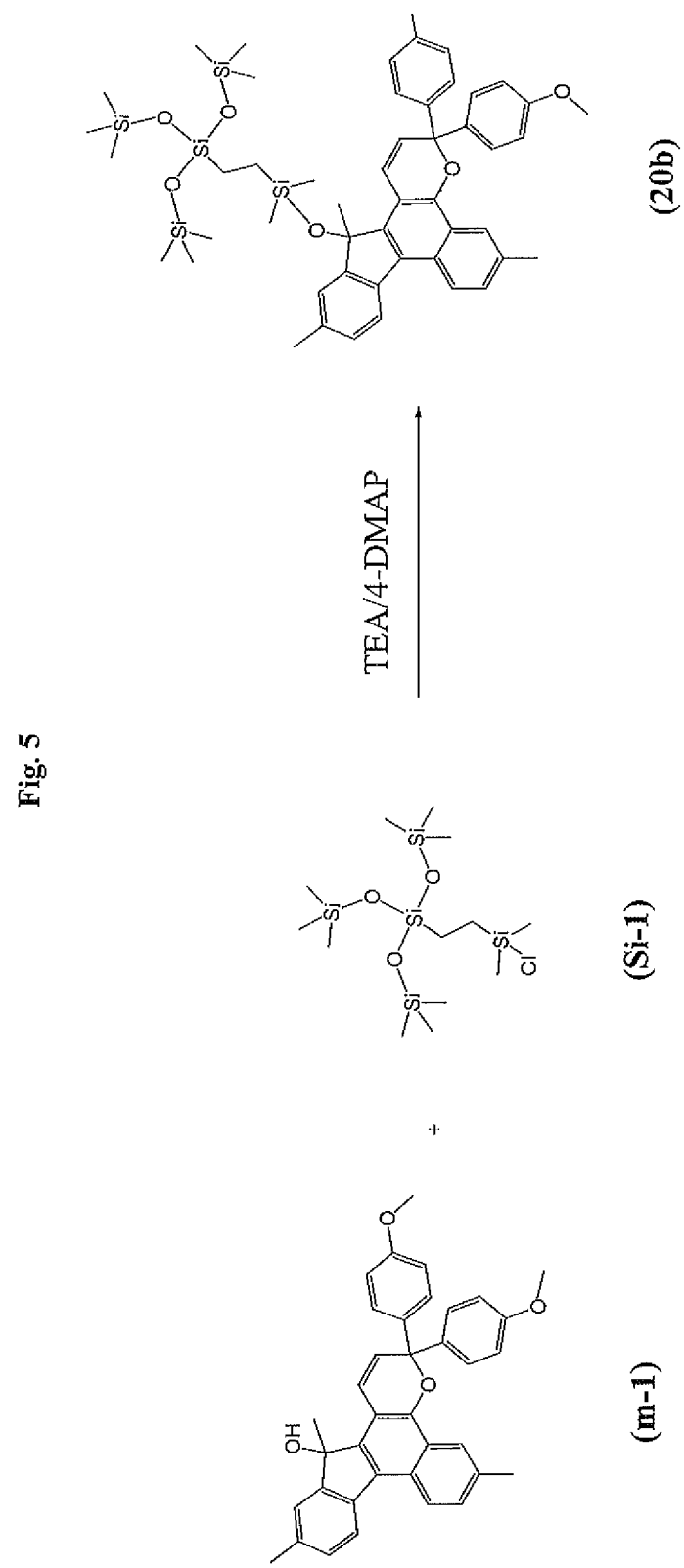
FIG. 5 is a representative schematic diagram of a synthetic reaction scheme depicting the preparation of a photochromic compound according to the present invention in which a pendent silane group represented by general formula (I) is bonded to a Position-13 hydroxyl of an indeno-fused naphthopyran prepared in accordance with the synthetic reaction scheme of FIG. 3.

Preparation of the photochromic compound according to the present invention, represented by general formula (20b) is generally described as follows with reference to FIG. 5. An indeno-fused naphthopyran (m-1) prepared in accordance with the reaction scheme depicted in and described with reference to FIG. 3, having a Position-13 hydroxyl group, is reacted with a chlorosilane represented by general formula (Si-1) in the presence of triethyl amine (TEA) and 4-(dimethylamino)-pyridine (4-DMAP) to form a photochromic compound according to the present invention represented by general formula (20b). The photochromic compound represented by general formula (20b) is as described previously herein.

Figure 6:
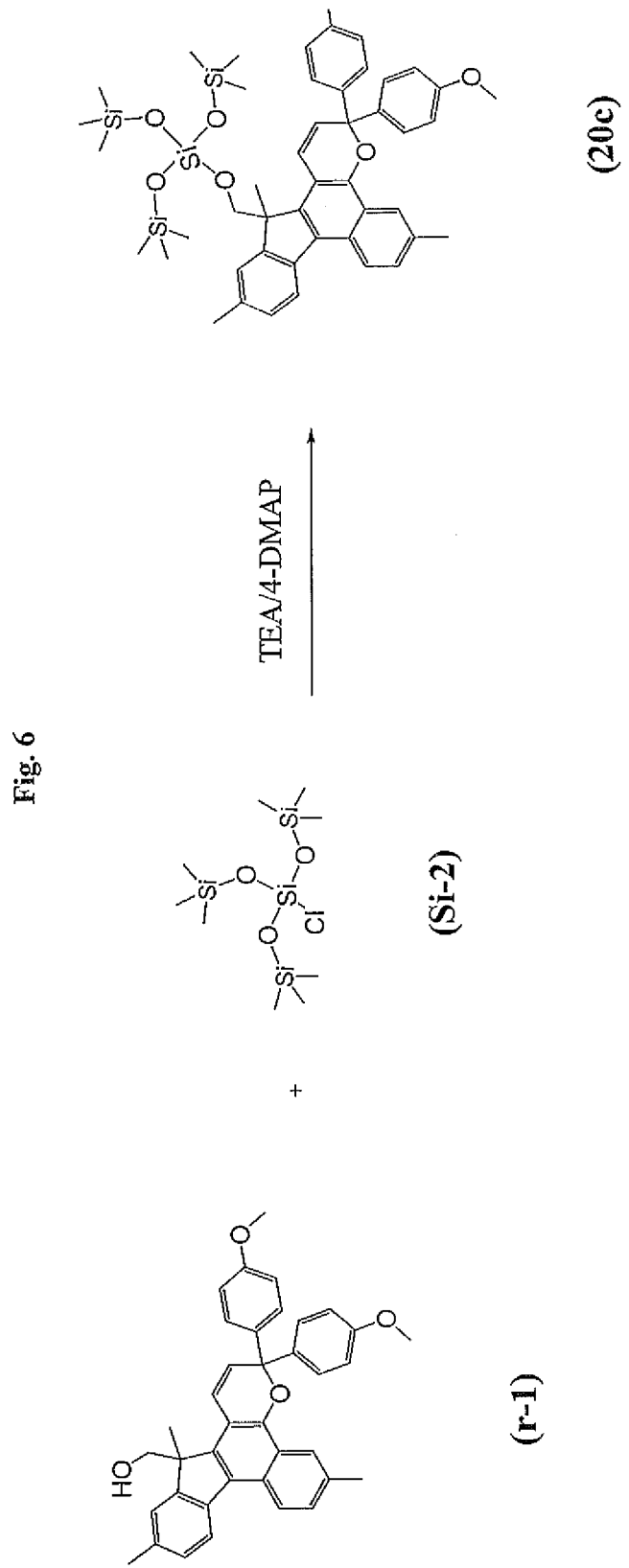
FIG. 6 is a representative schematic diagram of a synthetic reaction scheme depicting the preparation of a photochromic compound according to the present invention in which a pendent silane group represented by general formula (I) is bonded to a Position-13 methylenol group of an indeno-fused naphthopyran prepared in accordance with the synthetic reaction scheme of FIG. 4.

Preparation of the photochromic compound according to the present invention, represented by general formula (20c) is generally described as follows with reference to FIG. 6. An indeno-fused naphthopyran (r-1) prepared in accordance with the reaction scheme depicted in and described with reference to FIG. 4, having a Position-13 methylol group ($-CH_2-OH$), is reacted with a chlorosilane represented by general formula (Si-2) in the presence of triethyl amine (TEA) and 4-(dimethylamino)-pyridine (4-DMAP) to form a photochromic compound according to the present invention represented by general formula (20c). The photochromic compound represented by general formula (20c) is as described previously herein.

Figure 7:
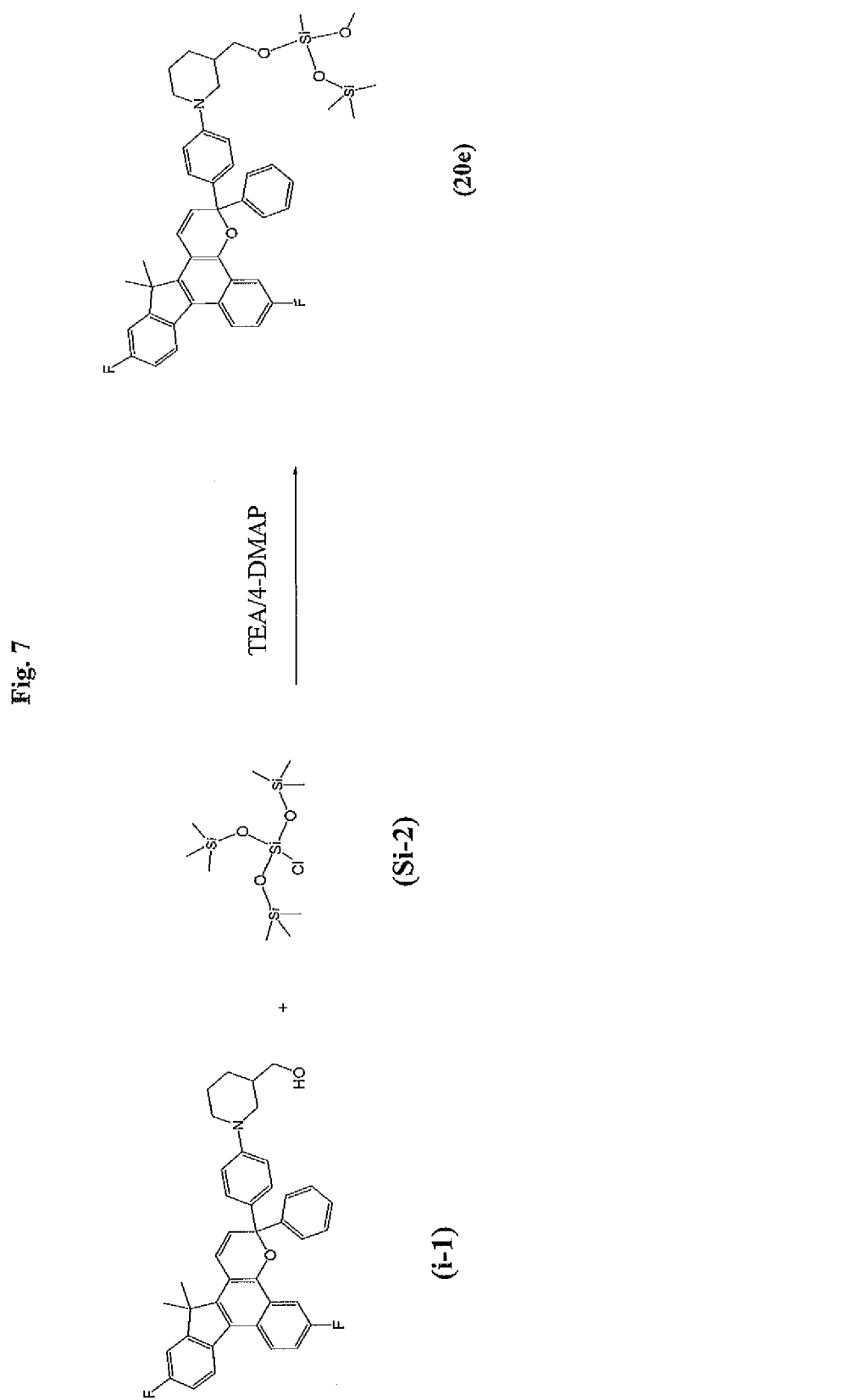
FIG. 7 is a representative schematic diagram of a synthetic reaction scheme depicting the preparation of a photochromic compound according to the present invention in which a pendent silane group represented by general formula (I) is bonded to a B group of an indeno-fused naphthopyran prepared in accordance with the synthetic reaction scheme of FIG. 2.

Preparation of the photochromic compound according to the present invention, represented by general formula (20e) is generally described as follows with reference to FIG. 7. An indeno-fused naphthopyran (i-1) prepared in accordance with the reaction scheme depicted in and described with reference to FIG. 2, in which B is a phenyl group substituted with a 3-methylol-piperidinyl group, is reacted with a chlorosilane represented by general formula (Si-2) in the presence of triethyl amine (TEA) and 4-(dimethylamino)-pyridine (4-DMAP) to form a photochromic compound according to the present invention represented by general formula (20e). The photochromic compound represented by general formula (20e) is as described previously herein.

Figure 8:
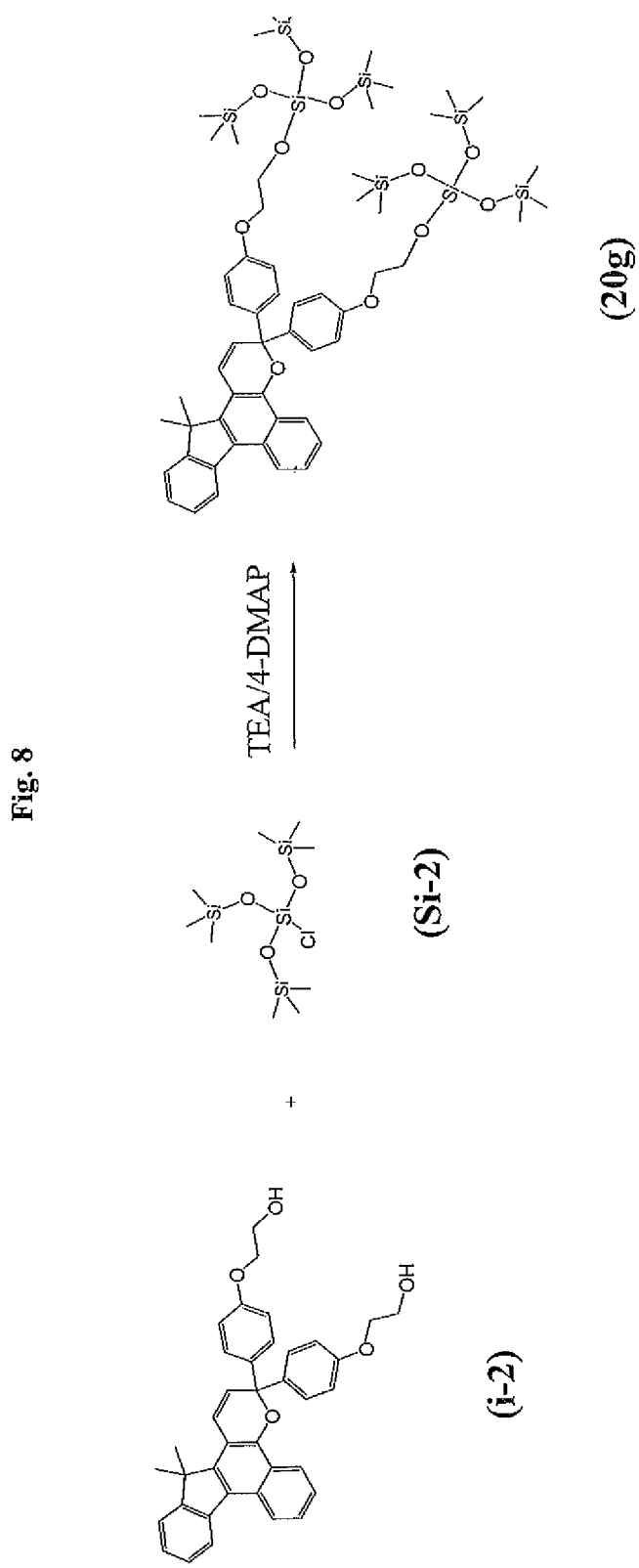
FIG. 8 is a representative schematic diagram of a synthetic reaction scheme depicting the preparation of a photochromic compound according to the present invention in which a pendent silane group represented by general formula (I) is bonded to each of the B and B' groups of an indeno-fused naphthopyran prepared in accordance with the synthetic reaction scheme of FIG. 2.

Preparation of the photochromic compound according to the present invention, represented by general formula (20g) is generally described as follows with reference to FIG. 8. An indeno-fused naphthopyran (i-2) prepared in accordance with the reaction scheme depicted in and described with reference to FIG. 2, in which B and B' are each 4-(2-hydroxy-ethoxy)-phenyl, is reacted with a chlorosilane represented by general formula (Si-2) in the presence of triethyl amine (TEA) and 4-(dimethylamino)-pyridine (4-DMAP) to form a photochromic compound according to the present invention represented by general formula (20g). The photochromic compound represented by general formula (20g) is as described previously herein.

Preparation of a photochromic compound according to the present invention, represented by general formula (20h) is generally described as follows with reference to FIG. 9. An indeno-fused naphthopyran (m-1) prepared in accordance with the reaction scheme depicted in and described with reference to FIG. 3, having a Position-13 hydroxyl group, is reacted with triethylene glycol in the presence of para-toluenesulfonic acid (PTSA) to form an intermediate indeno-fused naphthopyran represented by structure (m-1a) having a hydroxyl functional triethyleneglycol ether bonded to Position-13 thereof, which is then reacted with succinic anhydride, under art-recognized conditions, to form the carboxylic acid functional indeno-fused naphthopyran intermediate represented by structure (m-1b). The carboxylic acid functional indeno-fused naphthopyran intermediate represented by structure (m-1b) is then reacted with the hydroxyl functional silane represented by structure (Si-3), in the presence of dicyclohexyl carbodiimide (DCC) and 4-(dimethylamino)-pyiridine (4-DMAP), to from a photochromic compound according to the present invention represented by general formula (20h).

Figure 9:
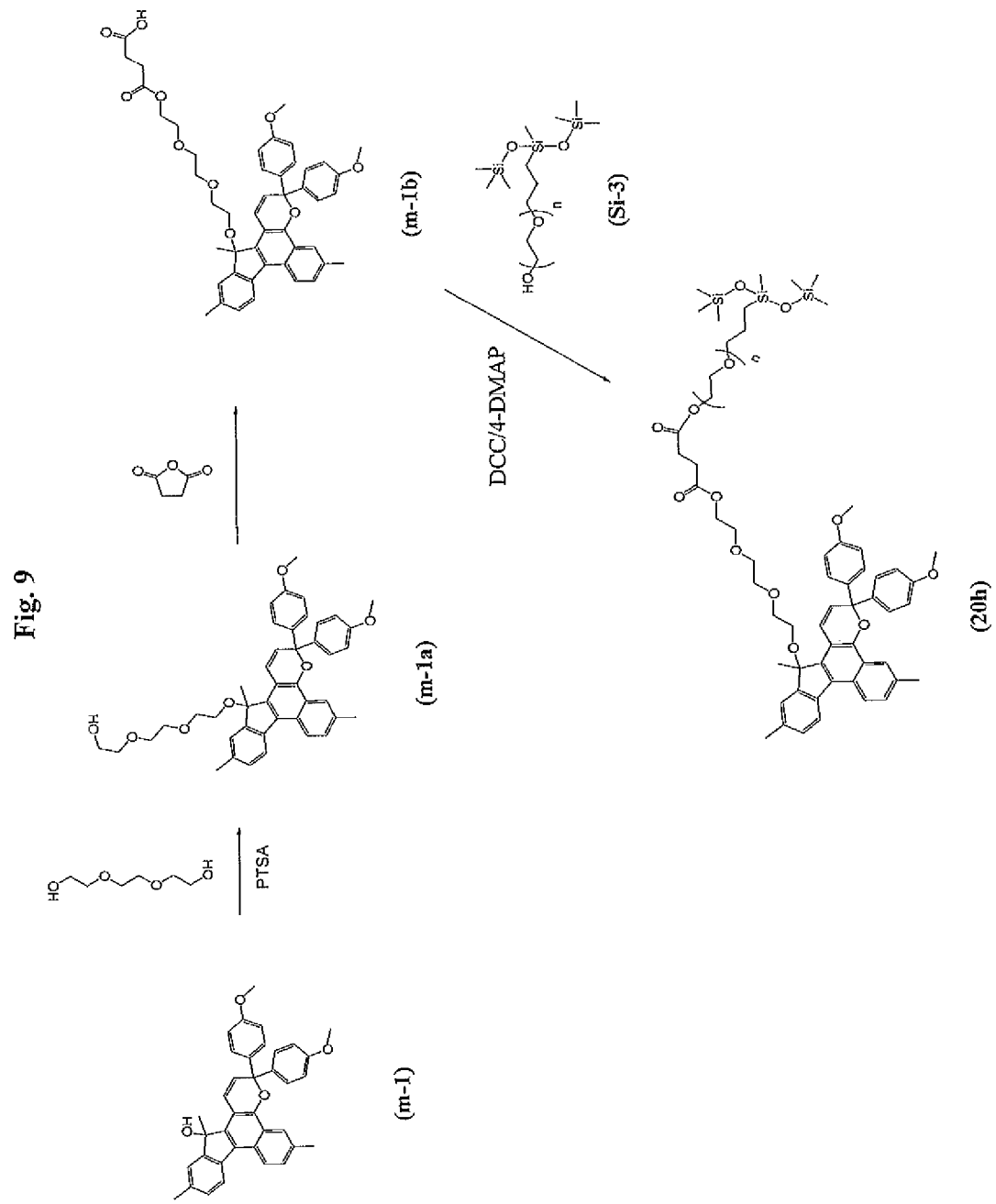
FIG. 9 is a representative schematic diagram of a synthetic reaction scheme depicting the preparation of a photochromic compound according to the present invention in which a pendent silane group represented by general formula (I) is bonded to a Position-13 hydroxyl of an indeno-fused naphthopyran prepared in accordance with the synthetic reaction scheme of FIG. 3.

In FIG. 9, the photochromic compound represented by general formula (20h) includes a pendent silane group represented by general formula (I), in which, m is 1, n is 2, R is methyl, Z is Si, each $R_1$ is methyl, and L is a divalent linking group represented by the following general formula (20h-L), in which n is from 1 to 4,

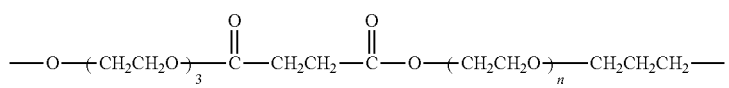

(20h-L)

With further reference to formula (20h), $R^5$, $R^7$ $R^8$, $R^9$, $R^{10}$ and $R^{12}$ are each hydrogen; $R^6$, $R^{11}$ and $R^{14}$ are each methyl; and B and B' are each a phenyl group substituted with a methoxy group.

Preparation of a photochromic compound according to the present invention, represented by general formula (20i) is generally described as follows with reference to FIG. 10. An indeno-fused naphthopyran represented by structure (i-3) prepared in accordance with the reaction scheme depicted in and described with reference to FIG. 2, having a 2,5-dioxypyrrolidin-1-yl-carboxylate group at Position-11 thereof, is reacted with an amine functional silane represented by general formula (Si-4) in the presence of pyridine to form a photochromic compound according to the present invention represented by general formula (20i).

In FIG. 10, the photochromic compound represented by general formula (20i) includes a pendent silane group represented by general formula (I), in which, m is 1, n is 2, R is methyl, Z is Si, each $R_1$ is methyl, and L is a divalent linking group represented by the following general formula (20i-L), —C(O)—NH—(CH$_2$)$_3$—                                    (20i-L)

With further reference to formula (20i), $R^5$, $R^8$, $R^9$, $R^{10}$ and $R^{12}$ are each hydrogen; $R^6$ and $R^7$ are each methoxy; $R^{13}$ and $R^{14}$ are each methyl; and B and B' are each a phenyl group substituted with a methoxy group.

Preparation of a photochromic compound according to the present invention, represented by general formula (20j) is generally described as follows with reference to FIG. 11. An indeno-fused naphthopyran represented by structure (m-1) prepared in accordance with the reaction scheme depicted in and described with reference to FIG. 3, having a hydroxy group at Position-13 thereof, is reacted with 3-hydroxy-1-propene, in the presence of paratoluenesulfonic acid (PTSA) and methyl cyanide (MeCN) to form a indeno-fused naphthopyran intermediate represented by structure (m-1c) having a 1-propenoxy group at Position-13 thereof. The indeno-fused naphthopyran intermediate represented by structure (m-1c) is then reacted with the silane represented by general formula (Si-5), in the presence of platinum catalyst (Pt) and toluene, to form the photochromic compound according to the present invention represented by general formula (20j).

Figure 11:
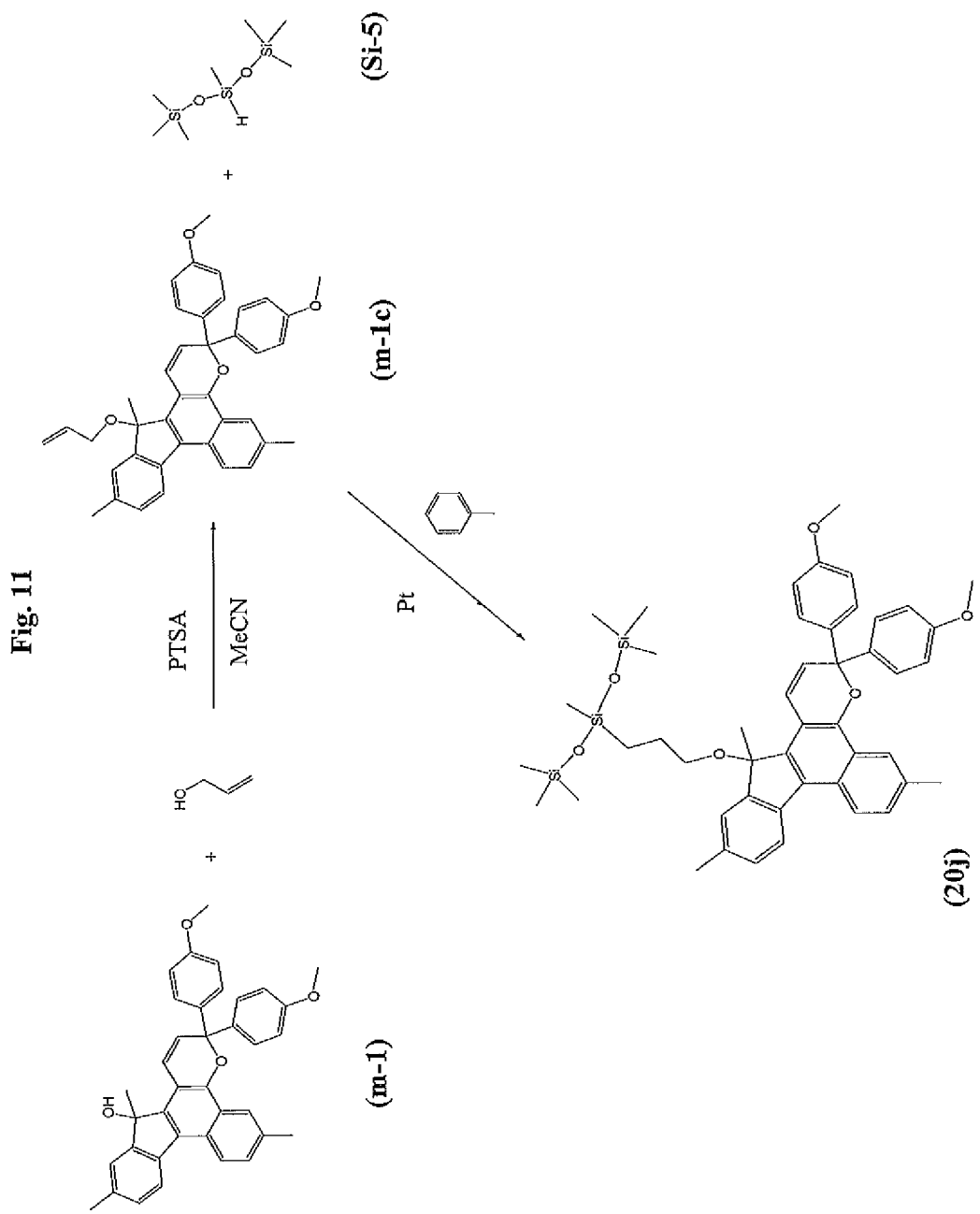
FIG. 11 is a representative schematic diagram of a synthetic reaction scheme depicting the preparation of a photochromic compound according to the present invention in which a pendent silane group represented by general formula (I) is bonded to a Position-13 hydroxyl of an indeno-fused naphthopyran prepared in accordance with the synthetic reaction scheme of FIG. 3.

In FIG. 11, the photochromic compound represented by general formula (20j) includes a pendent silane group represented by general formula (I), in which, m is 1, n is 2, R is methyl, Z is Si, each $R_1$ is methyl, and L is a divalent linking group represented by the following general formula (20j-L), —O—(CH$_2$)$_3$—                                        (20j-L)

With further reference to formula (20j) of FIG. 11, $R^5$, $R^7$, $R^8$, $R^9$, $R^{10}$ and $R^{12}$ are each hydrogen; $R^6$, $R^{11}$ and $R^{14}$ are each methyl; and B and B' are each a phenyl group substituted with a methoxy group.

Figure 12:
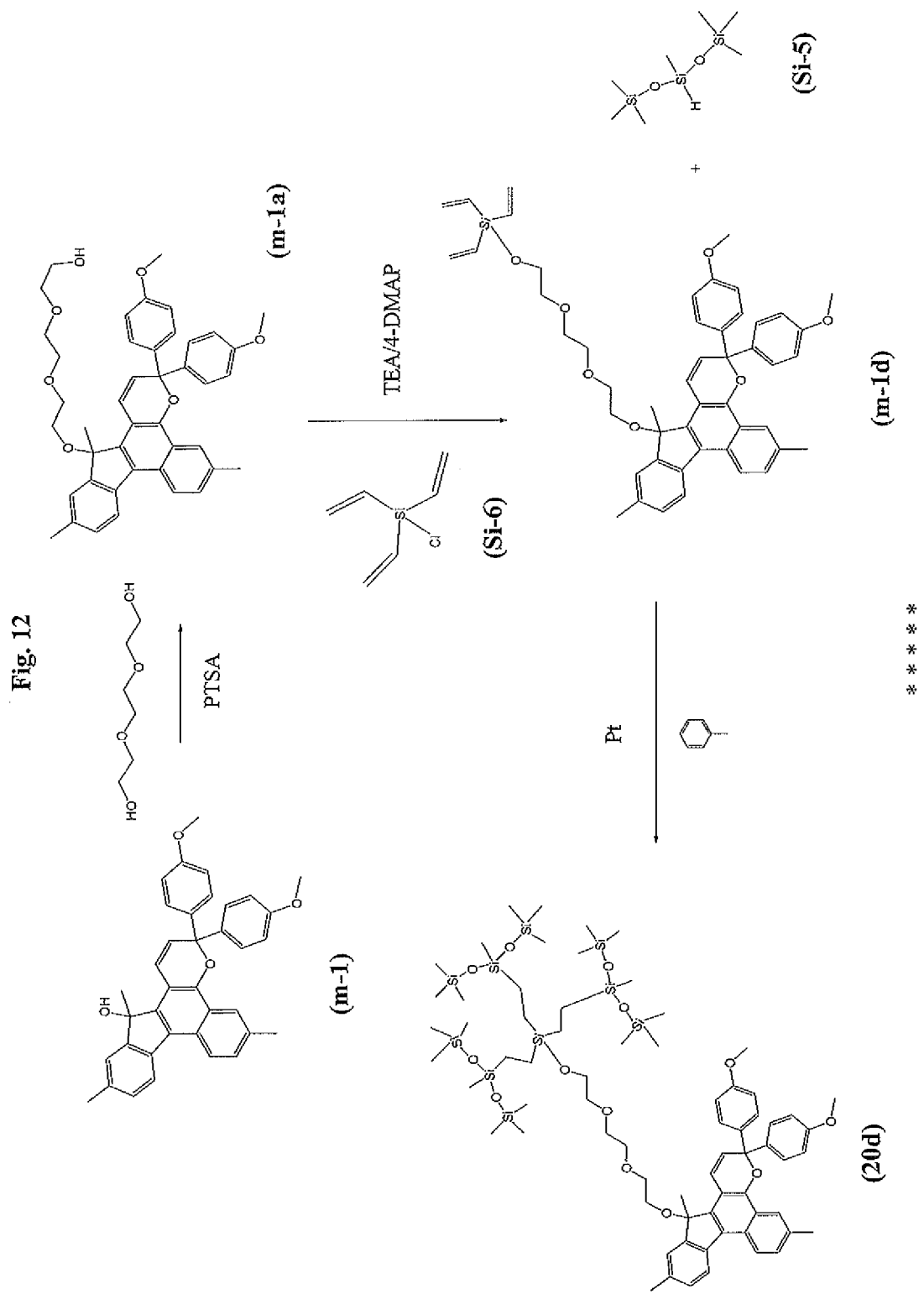
FIG. 12 is a representative schematic diagram of a synthetic reaction scheme depicting the preparation of a photochromic compound according to the present invention in which a pendent silane group represented by general formula (II) is bonded to a Position-13 hydroxyl of an indeno-fused naphthopyran prepared in accordance with the synthetic reaction scheme of FIG. 3.

Preparation of the photochromic compound according to the present invention, represented by general formula (20d) is generally described as follows with reference to FIG. 12. An indeno-fused naphthopyran (m-1) prepared in accordance with the reaction scheme depicted in and described with reference to FIG. 3, having a Position-13 hydroxyl group, is reacted with triethyleneglycol in the presence of para-toluenesulfonic acid (PTSA) to form an intermediate indeno-fused naphthopyran represented by structure (m-1a) having a hydroxyl functional triethyleneglycol ether bonded to Position-13 thereof. The intermediate indeno-fused naphthopyran represented by structure (m-1a) is then reacted with a trivinylchlorosilane represented by structure (Si-6) in the presence of triethylamine (TEA) and 4-(dimethylamino)-pyiridine, to form the tri-vinyl functional indeno-fused naphthopyran intermediate represented by structure (m-1d), which is then reacted with the silane represented by structure (Si-5), in the presence of platinum (Pt) and toluene, to form a photochromic compound according to the present invention represented by general formula (20d). The photochromic compound represented by general formula (20d) is as described previously herein.

The present invention also provides photochromic compositions (e.g., photochromic articles and photochromic coatings) that include a photochromic material according to the present invention, and an organic material. The photochromic materials according to the present invention may be incorporated into at least a portion of an organic material, such as a polymeric, oligomeric or monomeric material, to form a photochromic composition, which may be used, for example and without limitation, as or to form photochromic articles, such as optical elements, and photochromic coating compositions that may be applied to various substrates. As used herein the terms "polymer" and "polymeric material" refer to homopolymers and copolymers (e.g., random copolymers, block copolymers, and alternating copolymers), as well as blends and other combinations thereof. As used herein the terms "oligomer" and "oligomeric material" refer to a combination of two or more monomer units that is capable of reacting with additional monomer unit(s). As used herein the term "incorporated into" means physically and/or chemically combined with. For example, the photochromic materials according to the present invention may be physically combined with at least a portion of an organic material, for example and without limitation, by mixing or imbibing the photochromic material into the organic material; and/or chemically combined with at least a portion of an organic material, for example and without limitation, by copolymerization or otherwise bonding the photochromic material to the organic material.

The photochromic materials according to the present invention may each be used alone, in combination with other photochromic materials according to various non-limiting embodiments disclosed herein, or in combination with an appropriate complementary conventional photochromic material. For example, the photochromic materials according to the present invention may be used in conjunction with conventional photochromic materials having activated absorption maxima within the range of 300 to 1000 nanometers. Further, the photochromic materials according to the present invention may be used in conjunction with a complementary conventional polymerizable or a compatibilized photochromic material, such as for example, those disclosed in U.S. Pat. Nos. 6,113,814 (at col. 2, line 39 to col. 8, line 41), and 6,555,028 (at col. 2, line 65 to col. 12, line 56), which disclosures are hereby specifically incorporated by reference herein.

The photochromic compositions of the present invention may contain a mixture of photochromic materials. For example, although not limiting herein, mixtures of photochromic materials may be used to attain certain activated colors such as a near neutral gray or near neutral brown. See, for example, U.S. Pat. No. 5,645,767, col. 12, line 66 to col. 13, line 19, which describes the parameters that define neutral gray and brown colors and which disclosure is specifically incorporated by reference herein.

The present invention relates to a photochromic composition that includes an organic material, in which the organic material is a polymeric material, an oligomeric material and/or a monomeric material, and a photochromic material according to the present invention incorporated into at least a portion of the organic material. According to various non-limiting embodiments disclosed herein, the photochromic material may be incorporated into a portion of the organic material by at least one of blending and bonding the photochromic material with the organic material or a precursor thereof. As used herein with reference to the incorporation of photochromic materials into an organic material, the terms "blending" and "blended" mean that the photochromic material is intermixed or intermingled with the at least a portion of the organic material, but not bonded to the organic material. Further, as used herein with reference to the incorporation of photochromic materials into an organic material, the terms "bonding" or "bonded" mean that the photochromic material is linked to a portion of the organic material or a precursor thereof. For example, although not limiting herein, the photochromic material may be linked to the organic material through a reactive substituent.

When the organic material of the photochromic compositions of the present invention is a polymeric material, the photochromic material of the present invention may be incorporated into at least a portion of the polymeric material or at least a portion of the monomeric material or oligomeric material from which the polymeric material is formed. For example, photochromic materials according to various non-limiting embodiments disclosed herein that have a reactive substituent may be bonded to an organic material such as a monomer, oligomer, or polymer having a group with which a reactive moiety may be reacted, or the reactive moiety may be reacted as a co-monomer in the polymerization reaction from which the organic material is formed, for example, in a co-polymerization process.

As discussed previously herein, photochromic compositions according to various non-limiting embodiments of the present invention may include an organic material chosen from a polymeric material, an oligomeric material and/or a monomeric material. Examples of polymeric materials that may be used in conjunction with various non-limiting embodiments disclosed herein include, without limitation: polymers of bis(allyl carbonate) monomers; diethylene glycol dimethacrylate monomers; diisopropenyl benzene monomers; ethoxylated bisphenol A dimethacrylate monomers; ethylene glycol bismethacrylate monomers; poly(ethylene glycol) bismethacrylate monomers; ethoxylated phenol bismethacrylate monomers; alkoxylated polyhydric alcohol acrylate monomers, such as ethoxylated trimethylol propane triacrylate monomers; urethane acrylate monomers; vinylbenzene monomers; and styrene. Other non-limiting examples of suitable polymeric materials include polymers of polyfunctional, e.g., mono-, di- or multi-functional, acrylate and/or methacrylate monomers; poly($C_1$-$C_{12}$ alkyl methacrylates), such as poly(methyl methacrylate); poly(oxyalkylene) dimethacrylate; poly(alkoxylated phenol methacrylates); cellulose acetate; cellulose triacetate; cellulose acetate propionate; cellulose acetate butyrate; poly(vinyl acetate); poly(vinyl alcohol); poly(vinyl chloride); poly(vinylidene chloride); polyurethanes; polythiourethanes; thermoplastic polycarbonates; polyesters; poly(ethylene terephthalate); polystyrene; poly(alpha-methylstyrene); copolymers of styrene and methyl methacrylate; copolymers of styrene and acrylonitrile; polyvinylbutyral; and polymers of diallylidene pentaerythritol, particularly copolymers with polyol (allyl carbonate) monomers, e.g., diethylene glycol bis(allyl carbonate), and acrylate monomers, e.g., ethyl acrylate, butyl acrylate. Also contemplated are copolymers of the aforementioned monomers, combinations, and blends of the aforementioned polymers and copolymers with other polymers, e.g., to form interpenetrating network products.

Photochromic compositions according to the present invention may possess transparency, in which case the organic material(s) may be selected from one or more transparent polymeric materials. For example, the polymeric material may be an optically clear polymeric material prepared from a thermoplastic polycarbonate resin, such as a resin derived from bisphenol A and phosgene, which is commercially available under the trademark, LEXAN®; a polyester, such as the material commercially available under the trademark, MYLAR®; a poly(methyl methacrylate), such as the material commercially available under the trademark, PLEXIGLAS®; and polymerizates of a polyol(allyl carbonate) monomer, especially diethylene glycol bis(allyl carbonate), which monomer is commercially available under the trademark CR-39®; and polyurea-polyurethane (polyurea urethane) polymers, which are prepared, for example, by the reaction of a polyurethane oligomer and a diamine curing agent, a composition for one such polymer being commercially available under the trademark TRIVEX® by PPG Industries, Inc. Other non-limiting examples of suitable polymeric materials include polymerizates of copolymers of a polyol (allyl carbonate), e.g., diethylene glycol bis(allyl carbonate), with other copolymerizable monomeric materials, such as, but not limited to: copolymers with vinyl acetate, copolymers with a polyurethane having terminal diacrylate functionality, and copolymers with aliphatic urethanes, the terminal portion of which contain allyl or acrylyl functional groups. Still other suitable polymeric materials include, without limitation, poly(vinyl acetate), polyvinylbutyral, polyurethane, polythiourethanes, polymers chosen from diethylene glycol dimethacrylate monomers, diisopropenyl benzene monomers, ethoxylated bisphenol A dimethacrylate monomers, ethylene glycol bismethacrylate monomers, polyethylene glycol) bismethacrylate monomers, ethoxylated phenol bismethacrylate monomers and ethoxylated trimethylol propane triacrylate monomers, cellulose acetate, cellulose propionate, cellulose butyrate, cellulose acetate butyrate, polystyrene and copolymers of styrene with methyl methacrylate, vinyl acetate and acrylonitrile. According to one non-limiting embodiment, the polymeric material may be an optical resin commercially available from PPG Industries, Inc., under the CR-designation, e.g., CR-307, CR-407, and CR-607.

In an embodiment, the organic material of the photochromic compositions according to the present invention, is a polymeric material that may be chosen from poly(carbonate); copolymers of ethylene and vinyl acetate; copolymers of ethylene and vinyl alcohol; copolymers of ethylene, vinyl acetate, and vinyl alcohol (such as those that result from the partial saponification of copolymers of ethylene and vinyl acetate); cellulose acetate butyrate; poly(urethane); poly (acrylate); poly(methacrylate); epoxies; aminoplast functional polymers; poly(anhydride); poly(urea urethane); N-alkoxymethyl(meth)acrylamide functional polymers; poly (siloxane); poly(silane); and combinations and mixtures thereof.

Photochromic articles (e.g., optical elements) according to the present invention, more particularly, include a photochromic material that further includes a photochromic compound having bonded thereto at least one pendent silane group represented by general formula (I) and/or general formula (II), as described previously herein. The photochromic compound of the photochromic material may include one or more indeno-fused naphthopyrans, for example as described previously herein with regard to general formulas (III) and/or (IV).

Examples of photochromic articles according to the present invention include, but are not limited to, optical elements, displays, windows (or transparencies), mirrors, and liquid crystal cells. As used herein the term "optical" means pertaining to or associated with light and/or vision. The optical elements according to the present invention may include, without limitation, ophthalmic elements, display elements, windows, mirrors, and liquid crystal cell elements. As used herein the term "ophthalmic" means pertaining to or associated with the eye and vision. Non-limiting examples of ophthalmic elements include corrective and non-corrective lenses, including single vision or multi-vision lenses, which may be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, magnifying lenses, protective lenses, visors, goggles, as well as, lenses for optical instruments (for example, cameras and telescopes). As used herein the term "display" means the visible or machine-readable representation of information in words, numbers, symbols, designs or drawings. Non-limiting examples of display elements include screens, monitors, and security elements, such as security marks. As used herein the term "window" means an aperture adapted to permit the transmission of radiation there-through. Non-limiting examples of windows include automotive and aircraft transparencies, windshields, filters, shutters, and optical switches. As used herein the term "mirror" means a surface that specularly reflects a large fraction of incident light. As used herein the term "liquid crystal cell" refers to a structure containing a liquid crystal material that is capable of being ordered. One non-limiting example of a liquid crystal cell element is a liquid crystal display.

Photochromic articles according to the present invention, such as optical elements, may include a substrate and a photochromic material according to the present invention that is connected to at least a portion of the substrate. As used herein, the term "connected to" means associated with, either directly, or indirectly by means of another material or structure.

Photochromic articles according to the present invention may include, as discussed above, a substrate that may include one or more polymeric materials. The photochromic material of the present invention may be connected to at least a portion of the substrate by: incorporating the photochromic material into at least a portion of the polymeric material of the substrate; or by incorporating the photochromic material into at least a portion of the oligomeric or monomeric material from which the substrate is formed. For example, according to one non-limiting embodiment, the photochromic material may be incorporated into the polymeric material of the substrate by a cast-in-place method or by imbibition. The imbibition and the cast-in-place methods are discussed in further detail herein below.

In the imbibition method, the photochromic material is typically diffused into the polymeric material of a previously formed or fabricated article, such as a substrate or previously applied coating/film. Imbibition may be performed by immersing the polymeric material of a previously formed or fabricated article in a solution containing the photochromic material, with or without heating. Thereafter, although not required, the photochromic material may be bonded with the polymeric material (e.g., of the substrate or coating).

With cast-in-place methods, the photochromic material may be mixed with: a polymer and/or oligomer composition in solution or melt form; or monomer composition in liquid form, so as to form a castable photochromic composition. The tastable photochromic composition is then typically introduced into the cavity of a mold (e.g., a lens mold). The castable photochromic composition is then set within the mold so as to form a photochromic article.

With photochromic articles according to the present invention that include a substrate, the photochromic material may be connected to at least a portion of the substrate as part of a coating that is connected to at least a portion of the substrate. The substrate may be a polymeric substrate or an inorganic substrate (such as, but not limited to, a glass substrate). The photochromic material may be incorporated into at least a portion of a coating composition prior to application of the coating composition to the substrate. Alternatively, a coating composition may be applied to the substrate, at least partially set, and thereafter the photochromic material may be imbibed into at least a portion of the coating. As used herein, the terms "set" and "setting" include, without limitation, curing, polymerizing, cross-linking, cooling, and drying.

Photochromic articles according to the present invention may be formed by art-recognized in-mold coating (or in-mold casting) methods. With in-mold coating methods, a photochromic coating composition according to the present invention, which may be a liquid coating composition or a powder coating composition, is applied to at least a portion of the interior surface of a mold, and then at least partially set. Thereafter, a polymer solution or melt, or oligomeric or monomeric solution or mixture is cast or molded within the mold cavity and in contact with the previously applied photochromic coating composition, and at least partially set. The resulting photochromic article is then removed from the mold. Non-limiting examples of powder coatings in which the photochromic materials according to various non-limiting embodiments disclosed herein may be employed are set forth in U.S. Pat. No. 6,068,797 at col. 7, line 50 to col. 19, line 42, which disclosure is hereby specifically incorporated by reference herein.

Photochromic articles according to the present invention may also be formed by art-recognized over-mold methods. Over-mold methods typically involve forming a substrate within a mold, and then forming an interior space between the substrate and an interior surface of the mold, into which a photochromic coating composition is then subsequently introduced (e.g., injected) and then set (e.g., cured). Alternatively, over-mold methods may involve introducing a previously formed substrate into a mold, such that an interior space is defined between the substrate and an interior mold surface, and thereafter a photochromic coating composition is introduced (e.g., injected) into the interior space.

Photochromic articles according to the present invention may also be formed by means of art-recognized lamination methods. With lamination methods, a film comprising the photochromic material according to the present invention may be adhered or otherwise connect to a portion of the substrate, with or without an adhesive and/or the application of heat and pressure. Thereafter, if desired, a second substrate may be applied over the first substrate and the two substrates may be laminated together (i.e., by the application of heat and pressure) to form an element wherein the film comprising the photochromic material is interposed between the two substrates. Methods of forming films comprising a photochromic material may include for example and without limitation, combining a photochromic material with a polymeric solution or oligomeric solution or mixture, casting or extruding a film therefrom, and, if required, at least partially setting the film. Additionally or alternatively, a film may be formed (with or without a photochromic material) and imbibed with the photochromic material.

The coating composition comprising the photochromic material may be connected to at least a portion of the substrate of the photochromic article by art-recognized methods, such as applying a coating composition comprising the photochromic material to at least a portion of a surface of the substrate, and at least partially setting the coating composition. Additionally or alternatively, the coating comprising the photochromic material may be connected to the substrate, for example, through one or more additional coatings. For example, while not limiting herein, according to various non-limiting embodiments, an additional coating composition may be applied to a portion of the surface of the substrate, at least partially set, and thereafter the coating composition comprising the photochromic material may be applied over the additional coating and at least partially set. Non-limiting and art-recognized methods of applying coatings compositions to substrates are discussed herein below.

Examples of additional coatings and films that may be used in conjunction with the photochromic coatings and articles according to the present invention, include, but are not limited to: primer coatings and films (which typically reside under the photochromic coating); protective coatings and films (which are typically applied over the photochromic coating), including transitional coatings and films and abrasion resistant coatings and films; anti-reflective coatings and films; conventional photochromic coatings and films; polarizing coatings and films; and combinations thereof. As used herein the term "protective coating or film" refers to coatings or films that can prevent wear or abrasion, provide a transition in properties from one coating or film to another, protect against the effects of polymerization reaction chemicals and/or protect against deterioration due to environmental conditions such as moisture, heat, ultraviolet light, oxygen, etc.

Examples of primer coatings and films that may be used in conjunction with the photochromic coatings and/or with/to-form photochromic articles according to the present invention include, but are not limited to coatings and films that include coupling agents, at least partial hydrolysates of coupling agents, and mixtures thereof. As used herein "coupling agent" means a material having a group capable of reacting, binding and/or associating with a group on a surface. Coupling agents according to various non-limiting embodiments disclosed herein may include organometallics such as silanes, titanates, zirconates, aluminates, zirconium aluminates, hydrolysates thereof and mixtures thereof. As used herein the phrase "at least partial hydrolysates of coupling agents" means that some to all of the hydrolyzable groups on the coupling agent are hydrolyzed. Other non-limiting examples of primer coatings that are suitable for use in conjunction with the various non-limiting embodiments disclosed herein include those primer coatings described U.S. Pat. No. 6,025,026 at col. 3, line 3 to col. 11, line 40 and U.S. Pat. No. 6,150,430 at col. 2, line 39 to col. 7, line 58, which disclosures are hereby specifically incorporated herein by reference.

As used herein, the term "transitional coating and film" means a coating or film that aids in creating a gradient in properties between two coatings or films, or a coating and a film. For example, although not limiting herein, a transitional coating may aid in creating a gradient in hardness between a relatively hard coating and a relatively soft coating. Non-limiting examples of transitional coatings include radiation-cured, acrylate-based thin films as described in U.S. Patent Application Publication 2003/0165686 at paragraphs 79-173, which are hereby specifically incorporated by reference herein.

As used herein the term "abrasion resistant coating and film" refers to a protective polymeric material that demonstrates a resistance to abrasion that is greater than a standard reference material, e.g., a polymer made of CR-39® monomer available from PPG Industries, Inc, as tested in a method comparable to ASTM F-735 Standard Test Method for Abrasion Resistance of Transparent Plastics and Coatings Using the Oscillating Sand Method. Non-limiting examples of abrasion resistant coatings include, for example, abrasion-resistant coatings comprising organosilanes, organosiloxanes, abrasion-resistant coatings based on inorganic materials such as silica, titania and/or zirconia, organic abrasion-resistant coatings of the type that are ultraviolet light curable, oxygen barrier-coatings, UV-shielding coatings, and combinations thereof.

Non-limiting examples of antireflective coatings and films include a monolayer, multilayer or film of metal oxides, metal fluorides, or other such materials, which may be deposited onto the articles disclosed herein (or onto films that are applied to the articles), for example, through vacuum deposition, sputtering, etc. Non-limiting examples of conventional photochromic coatings and films include, but are not limited to, coatings and films comprising conventional photochromic materials. Non-limiting examples of polarizing coatings and films include, but are not limited to, coatings and films comprising dichroic compounds that are known in the art.

Additional coating compositions (e.g., primers and overcoats) that may be used with photochromic coating compositions according to the present invention and/or to form photochromic articles according to the present invention, may be applied to/formed: on a substrate prior to application of the photochromic coating; and/or over a previously applied photochromic coating. For example, a primer coating may be formed on the substrate prior to applying a photochromic coating composition according to the present invention. Additionally or alternatively, an additional coating or film may be applied (e.g., as an over-coat or over-coating) at least partially over a previously applied photochromic coating composition according to the present invention. For example, a transitional coating may be formed over a previously applied photochromic coating composition according to the present invention, and an abrasion resistant coating may then be applied over the transitional coating.

Photochromic coating compositions according to the present invention include: a photochromic compound (e.g., an indeno-fused naphthopyran represented by general formulas III and/or IV) having bonded thereto at least one pendent silane group represented by general formulas (I) and/or (II) as described previously herein; a curable resin composition; and optionally a solvent. The photochromic coating composition may be in the form of art-recognized liquid coatings and powder coatings. The photochromic coating compositions of the present invention may be thermoplastic or thermosetting coating compositions. In an embodiment, the photochromic coating composition is a curable or thermosetting coating composition.

The curable resin composition of the curable photochromic coating compositions according to the present invention typically include: a first reactant (or component) having functional groups, e.g., an epoxide functional polymer reactant; and a second reactant (or component) that is a crosslinking agent having functional groups that are reactive towards and that can form covalent bonds with the functional groups of the first reactant. The first and second reactants of the curable resin composition of the curable photochromic coating composition may each independently comprise one or more functional species, and are each present in amounts sufficient to provide cured photochromic coatings having a desirable combination of physical properties, e.g., smoothness, optical clarity, solvent resistance and hardness.

Examples of curable resin compositions that may be used with the curable photochromic coating compositions according to the present invention include, but are not limited to: curable resin compositions comprising epoxide functional polymer (e.g., (meth)acrylic polymers containing residues of glycidyl (meth)acrylate) and epoxide reactive crosslinking agent (e.g., containing active hydrogens, such as hydroxyls, thiols and amines); and curable resin compositions comprising hydroxy functional polymer and capped (or blocked) isocyanate functional crosslinking agent.

In an embodiment, the curable resin composition of the photochromic coating composition of the present invention is a curable urethane (or polyurethane) resin composition. Curable urethane resin compositions useful in the photochromic coating compositions of the present invention typically include: an active hydrogen functional polymer, such as a hydroxy functional polymer; and a capped (or blocked) isocyanate functional crosslinking agent. Hydroxy functional polymers that can be used in such compositions include, but are not limited to, art-recognized hydroxy functional vinyl polymers, hydroxy functional polyesters, hydroxy functional polyurethanes and mixtures thereof.

Vinyl polymers having hydroxy functionality can be prepared by free radical polymerization methods that are known to those of ordinary skill in the art. In an embodiment of the present invention, the hydroxy functional vinyl polymer is prepared from a majority of (meth)acrylate monomers and is referred to herein as a "hydroxy functional (meth)acrylic polymer."

Hydroxy functional polyesters useful in curable photochromic coating compositions comprising capped isocyanate functional crosslinking agent can be prepared by art-recognized methods. Typically, diols and dicarboxylic acids or diesters of dicarboxylic acids are reacted in a proportion such that the molar equivalents of hydroxy groups is greater than that of carboxylic acid groups (or esters of carboxylic acid groups) with the concurrent removal of water or alcohols from the reaction medium.

Hydroxy functional urethanes can be prepared by art-recognized methods, for example, as previously described herein. Typically one or more Bifunctional isocyanates are reacted with one or more materials having two active hydrogen groups (e.g., diols or dithiols), such that the ratio of active hydrogen groups to isocyanate groups is greater than 1, as is known to the skilled artisan.

By "capped (or blocked) isocyanate crosslinking agent" is meant a crosslinking agent having two or more capped isocyanate groups that can decap (or deblock) under cure conditions, e.g., at elevated temperature, to form free isocyanate groups and free capping groups. The free isocyanate groups formed by decapping of the crosslinking agent are preferably capable of reacting and forming substantially permanent covalent bonds with the active hydrogen groups of the active hydrogen functional polymer (e.g., with the hydroxy groups of a hydroxy functional polymer).

It is desirable that the capping group of the capped isocyanate crosslinking agent not adversely affect the curable photochromic coating composition upon decapping from the isocyanate (i.e., when it becomes a free capping group). For example, it is desirable that the free capping group neither become trapped in the cured film as gas bubbles nor excessively plasticize the cured film. Capping groups useful in the present invention preferably have the characteristics of being nonfugitive or capable of escaping substantially from the forming coating prior to its vitrification. Typically, the free capping groups escape substantially from the forming (e.g., curing) coating prior to its vitrification.

Classes of capping groups of the capped isocyanate crosslinking agent may be selected from: hydroxy functional compounds, e.g., linear or branched $C_2$-$C_8$ alcohols, ethylene glycol butyl ether, phenol and p-hydroxy methylbenzoate; 1H-azoles, e.g., 1H-1,2,4-triazole and 1H-2,5-dimethylpyrazole; lactams, e.g., e-caprolactam and 2-pyrrolidinone; ketoximes, e.g., 2-propanone oxime and 2-butanone oxime. Other suitable capping groups include, morpholine, 3-aminopropyl morpholine and N-hydroxy phthalimide.

The isocyanate or mixture of isocyanates of the capped isocyanate crosslinking agent has two or more isocyanate groups (e.g., 3 or 4 isocyanate groups). Examples of suitable isocyanates that may be used to prepare the capped isocyanate crosslinking agent include, monomeric diisocyanates, e.g., α,α'-xylylene diisocyanate, α,α,α',α'-tetramethylxylylene diisocyanate and 1-isocyanato-3-isocyanatomethyl-3,5,5-trimethylcyclohexane (isophorone diisocyanate or IPDI), and dimers and trimers of monomeric diisocyanates containing isocyanurate, uretidino, biruet or allophanate linkages, e.g., the trimer of IPDI.

The capped isocyanate crosslinking agent may also be selected from oligomeric capped isocyanate functional adducts. As used herein, by "oligomeric capped polyisocyanate functional adduct" is meant a material that is substantially free of polymeric chain extension. Oligomeric capped polyisocyanate functional adducts can be prepared by art-recognized methods from, for example, a compound containing three or more active hydrogen groups, e.g., trimethylolpropane (TMP), and an isocyanate monomer, e.g., 1-isocyanato- 3,3,5-trimethyl-5-isocyanatomethylcyclohexane (IPDI), in a molar ratio of 1:3, respectively. In the case of TMP and IPDI, by employing art-recognized starved feed and/or dilute solution synthesis techniques, an oligomeric adduct having an average isocyanate functionality of 3 can be prepared (e.g., "TMP-3IPDI"). The three free isocyanate groups per TMP-3IPDI adduct are then capped with a capping group, e.g., a linear or branched $C_2$-$C_8$ alcohol.

To catalyze the reaction between the isocyanate groups of the capped polyisocyanate crosslinking agent and the hydroxy groups of the hydroxy functional polymer, one or more catalysts are typically present in the curable photochromic coating composition in amounts of from, for example, 0.1 to 5 percent by weight, based on total resin solids of the composition. Classes of useful catalysts include but are not limited to, metal compounds, in particular, organic tin compounds, e.g., tin(II) octanoate and dibutyltin(IV) dilaurate, and tertiary amines, e.g., diazabicyclo[2.2.2]octane.

Curable photochromic coating compositions according to the present invention, which include hydroxy functional polymer and capped isocyanate functional crosslinking agent, typically have present therein hydroxy functional polymer in an amount of from 55 percent to 95 percent by weight, based on total resin solids weight of the composition, e.g., from 75 percent to 90 percent by weight, based on total resin solids weight of the composition. The capped isocyanate functional crosslinking agent is typically present in the curable resin composition in an amount corresponding to the balance of these recited ranges, i.e., 5 to 45, particularly 10 to 25, percent by weight.

With the curable urethane resin compositions of the curable photochromic coating compositions of the present invention, the equivalent ratio of isocyanate equivalents in the capped isocyanate crosslinking agent to hydroxy equivalents in the hydroxy functional polymer is typically within the range of 1:3 to 3:1, e.g., 1:2 to 2:1. While equivalent ratios outside of this range can be employed, they are generally less desirable due to performance deficiencies in cured photochromic films obtained therefrom. Curable photochromic coating compositions according to the present invention that include hydroxy functional polymer and capped isocyanate functional crosslinking agent are typically cured at a temperature of from 120° C. to 190° C. over a period of from 10 to 60 minutes.

Photochromic coating compositions according to the present invention may optionally further include a solvent. Examples of suitable solvents include, but art not limited to, acetates, alcohols, ketones, glycols, ethers, aliphatics, cycloaliphatics and aromatics. Examples of acetates include, but are not limited to, ethyl acetate, butyl acetate, and glycol acetate. Examples of ketones include, but are not limited to, methyl ethyl ketone and methyl-N-amyl ketone. Examples of aromatics include, but are not limited to, are toluene, naphthalene and xylene. In an embodiment, one or more solvents are added to each of the first reactant and the second reactant. Suitable solvent blends can include, for example, one or more acetates, propanol and its derivatives, one or more ketones, one or more alcohols and/or one or more aromatics. If present, the solvent is typically present in an amount of from 5 to 60 percent by weight, or 5 to 40 percent by weight, or 10 to 25 percent by weight, based on the total weight of the photochromic coating composition (inclusive of the solvent weight).

Curable photochromic coating compositions according to the present invention may optionally contain additives such as waxes for flow and wetting, flow control agents, e.g., poly(2-ethylhexyl)acrylate, adjuvant resin to modify and optimize coating properties, antioxidants and ultraviolet (UV) light absorbers. Examples of useful antioxidants and UV light absorbers include those available commercially from Ciba-Geigy under the trademarks IRGANOX and TINUVIN. These optional additives, when used, are typically present in amounts up to 20 percent by weight (e.g., from 0.5 to 10 percent by weight), based on total weight of resin solids of the curable resin composition.

Photochromic compositions, articles and coating compositions according to the present invention may further include art-recognized additives that aid or assist in the processing and/or performance of the compositions or articles. Non-limiting examples of such additives include photoinitiators, thermal initiators, polymerization inhibitors, solvents, light stabilizers (such as, but not limited to, ultraviolet light absorbers and light stabilizers, such as hindered amine light stabilizers (HALS)), heat stabilizers, mold release agents, rheology control agents, leveling agents (such as, but not limited to, surfactants), free radical scavengers, adhesion promoters (such as hexanediol diacrylate and coupling agents), and combinations and mixtures thereof.

The photochromic materials according to the present invention may be used in amounts (or ratios) such that the organic material or substrate (e.g., photochromic articles and photochromic coatings) into which the photochromic materials are incorporated or otherwise connected exhibits desired optical properties. For example, the amount and types of photochromic materials may be selected such that the organic material or substrate may be clear or colorless when the photochromic material is in the closed-form (i.e., in the bleached or unactivated state) and may exhibit a desired resultant color when the photochromic material is in the open-form (that is, when activated by actinic radiation). The precise amount of the photochromic material to be utilized in the various photochromic compositions and articles described herein is not critical provided that a sufficient amount is used to produce the desired effect. The particular amount of the photochromic material used may depend on a variety of art-recognized factors, such as but not limited to, the absorption characteristics of the photochromic material, the color and intensity of the color desired upon activation, and the method used to incorporate or connect the photochromic material to the substrate. Although not limiting herein, according to various non-limiting embodiments disclosed herein, the amount of the photochromic material that is incorporated into an organic material may range from 0.01 to 40 weight percent (e.g., from 0.05 to 15, or from 0.1 to 5 weight percent), based on the weight of the organic material.

EXAMPLES

Part 1 describes the preparation of the propargyl alcohols (PA) 1-23. Part 2 describes the preparation of the naphthols (N) 1-27. Part 3 describes the preparation of intermediate photochromic compounds, the majority of which were used as Comparative Examples (CE) 1-78. Part 4 describes the preparation of Examples 1-87 utilizing the materials of Parts 1, 2 & 3. Part 5 describes the photochromic performance testing and results of the Examples and Comparative Examples. Part 6 describes the preparation and testing of polyurethane coatings containing Example 25 and Comparative Example 78. The results reported in Tables 1 and 2 showed that the compounds of the present invention demonstrated improved photochromic performance over the comparative examples with a higher sensitivity, higher ΔOD at saturation and/or a faster Fade Half Life ("T½"), i.e., a lower value.

The specific disclosure of the patent examples referred to in Parts 1-4 of U.S. Pat. Nos. 5,458,814; 5,645,767; 7,465,415; 77,527,754; and 7,557,208; and U.S. Patent Publications: 2006/0228557 and 2008/0103301 are incorporated herein by reference.

In the following parts, the acronyms used herein mean as follows:

EtOAc—ethyl acetate;
DCM—dichloromethane;
DHP—3,4-dihydro-2H-pyran;
DMAP or 4-DMAP—4-dimethylaminopyridine;
DMF or dDMF—anhydrous dimethylformamide;
DMSO—dimethyl sulfoxide;
h or hrs—hours;
MeCN or dMeCN—anhydrous acetonitrile;
MeOH—methanol;
MS—probe mass spectroscopy;
NMR—proton nuclear magnetic resonance;
TEA—triethanolamine;
THF or dTHF—anhydrous tetrahydrofuran;
PTSA—para-toluenesulfonic acid; and
V/V—ratio of solvents was based on volume to volume.

Part 1—Preparation of Propargyl Alcohols (PA) 1-23

PA-1

Step 1 of Example 1 in U.S. Pat. No. 5,458,814 was followed to prepare 1,1-bis(4-methoxyphenyl)-2-propyn-1-ol. The product was used without further purification.

PA-2

Step 1

The procedure of step 1 of Example 7 of U.S. Pat. No. 7,465,415B2 was followed except that (4-hydroxyphenyl)(4-methoxyphenyl)methanone was used instead of (4-fluorophenyl)(4-hydroxyphenyl)methanone to produce (4-(2-hydroxyethoxy)phenyl)(4-methoxyphenyl)methanone. MS analysis supported the molecular weight of the product.

Step 2

The procedure of step 1 of Example 5 of U.S. Pat. No. 7,465,415B2 was followed except that (4-(2-hydroxyethoxy)phenyl)(4-methoxyphenyl)methanone used in place of (4-fluorophenyl)(4-(2-hydroxyethoxy)phenyl)methanone to produce 1-(4-(2-hydroxyethoxy)phenyl)-1-(4-methoxyphenyl)prop-2-yn-1-ol. The product was used without further purification.

PA-3

Step 1

In a 0.5 L single neck flask bis(4-fluorophenyl)methanone (20 g) was dissolved in DMSO (40 mL), piperidine 3-methanol (9.6 g) was added and then TEA (11.5 mL) was added. The reaction mixture was stirred at 70° C. After 20 hrs the reaction was cooled to room temperature, water (0.8 L) was added and resulting mixture was extracted with DCM (2 times with 300 mL each time). The organic phase was collected, washed with water (4 times with 300 mL each time) and the solvent evaporated to produce the product (25 g). MS analysis supported the molecular weight of the product (4-fluorophenyl)(4-(3-(hydroxymethyl)piperidin-1-yl)phenyl)methanone.

Step 2

The procedure of step 1 of Example 5 of U.S. Pat. No. 7,465,415B2 was followed except that the product of Step 1 (4-fluorophenyl)(4-(3-(hydroxymethyl)piperidin-1-yl)phenyl)methanone was used in place of (4-fluorophenyl)(4-(2-hydroxyethoxy)phenyl)methanone to produce 1-(4-fluorophenyl)-1-(4-(3-(hydroxymethyl)piperidin-1-yl)phenyl)prop-2-yn-1-ol. The product was used without further purification.

PA-4

Steps 2 to 3 of example 7 U.S. Pat. No. 7,465,415B2 were followed except that (4-fluorophenyl)(4-methoxyphenyl)methanone was used in place of (4-fluorophenyl)(4-(2-hydroxyethoxy)phenyl)methanone to produce 1-(4-methoxyphenyl)-1-(4-morpholinophenyl)prop-2-yn-1-ol. The product was used without further purification.

PA-5

Steps 1 to 3 of Example 7 in U.S. Pat. No. 7,465,415B2 were followed to prepare 1-(4-(2-hydroxyethoxy)-phenyl-1-(4-morpholinophenyl)-2-propyn-1-ol. The product was used without further purification.

PA-6

Step 1 of Example 5 in U.S. Pat. No. 7,465,415B2 was followed to prepare 1-(4-fluorophenyl)-1-(4'-(2-hydroxyethoxy)phenyl)-2-propyn-1-ol. The product was used without further purification.

PA-7

Step 1

Into a 0.5 L reaction flask dihydroxybenzophenone (15 g) was suspended in water (150 mL) and a solution of NaOH (10.9 g in 120 mL) was added while stirring. 2-Chloroethanol (31.7 mL) was added. The resulting mixture was heated to reflux for 2 days. The mixture was cooled to room temperature and filtered. The resulting solid was collected, dissolved in TI-IF (200 mL) and washed once with KOH 1M (300 mL). The organic layer was collected and the solvents evaporated to produce 8.5 g of product. MS analysis supported the molecular weight of bis(4-(2-hydroxyethoxy)phenyl)methanone.

Step 2

Into a 0.5 L reaction flask was added THF (200 mL), product from Step 1, bis(4-(2-hydroxyethoxy)phenyl)methanone and 3,4-dihydro-2H-pyran (DHP, 5.5 mL). PTSA (57 mg) was added and the reaction mixture stirred 12 hrs at room temperature. Then, the solvent was evaporated, the residue dissolved in DCM (200 mL), extracted with aqueous 1% $K_2CO_3$ (one time with 150 mL) and brine (100 mL). After evaporation of the solvent the product (7.1 g) was collected. MS analysis supported the molecular weight of the product bis(4-(2-((tetrahydro-2H-pyran-2-yl)oxy)ethoxy)phenyl)methanone.

Step 3

The product of Step 2 was added to a 1 L reaction flask with 100 mL of DMF. The mixture was cooled to 5° C. and was bubbled with acetylene gas for 10 min. A slurry of sodium acetylide (18% weight in Xylene/mineral oil from Aldrich, 7 mL) was added all at once. The reaction mixture was stirred for 0.5 hrs and then the ice bath was removed. After 10 hrs the mixture was poured into a flask containing ice (150 g) and stirred for 10 minutes. EtOAc (300 mL) was added and the mixture phase separated. During the phase separation a saturated solution of $NH_4Cl$ (250 mL) was added. The recovered organic layer was washed with water (2 times with 150 mL each time). The resulting solution was concentrated by rotary evaporation to provide 21 g of product. MS analysis supported the molecular weight of the product 1,1-bis(4-(2-((tetrahydro-2H-pyran-2-yl)oxy)ethoxy)phenyl)prop-2-yn-1-ol.

PA-8

Steps 1 to 2 of PA-3 were followed except that 4-hydroxy piperidine was used instead of piperidine 3-methanol to produce 1-(4-fluorophenyl)-1-(4-(4-hydroxypiperidin-1-yl) phenyl)prop-2-yn-1-ol. The product was used without further purification.

PA 9

Steps 1 to 2 of PA-3 were followed except that piperidine 2-methanol was used instead of piperidine 3-methanol to produce 1-(4-fluorophenyl)-1-(4-(2-(hydroxymethyl)piperidin-1-yl)-phenyl)prop-2-yn-1-ol. The product was used without further purification.

PA-10

Steps 1 to 2 of PA-3 were followed except that (4-fluorophenyl)(phenyl)methanone was used instead of bis(4-fluorophenyl)methanone to produce 1-(4-(3-(hydroxymethyl)piperidin-1-yl)phenyl)-1-phenylprop-2-yn-1-ol. The product was used without further purification.

PA-11

Steps 1 to 2 of PA-3 were followed except that piperazine-1-carbaldehyde was used instead of piperidine 3-methanol to produce 1-(4-fluorophenyl)-1-(4-(4-formylpiperazin-1-yl) phenyl)prop-2-yn-1-ol. MS analysis supported the molecular weight of the product.

PA-12

The procedure of Step 1 of Example 5 of U.S. Pat. No. 7,465,415B2 was followed except that (4-bromophenyl) (phenyl)methanone used in place of (4-fluorophenyl)(4-(2-hydroxyethoxy)phenyl)methanone to produce 1-(4-bromophenyl)-1-phenylprop-2-yn-1-ol. The product was used without further purification.

PA-13

Steps 1 to 2 of PA-3 were followed except that 2-(piperazin-1-yl)ethanol was used instead of piperidine 3-methanol to produce 1-(4-fluorophenyl)-1-(4-(4-(2-hydroxyethyl)piperazin-1-yl)phenyl)prop-2-yn-1-ol. The product was used without further purification.

PA-14

Steps 1 to 2 of PA-3 were followed except that morpholin-2-ylmethanol was used instead of piperidine 3-methanol to produce 1-(4-fluorophenyl)-1-(4-(2-(hydroxymethyl)morpholino)phenyl)prop-2-yn-1-ol. The product was used without further purification.

PA-15

Step 1

In a dried flask under a nitrogen atmosphere, 4-methoxybenzophenone (32 g) was dissolved in acetic acid (250 mL) and then $Br_2$ (20 mL) was slowly added. The solution was stirred at room temperature for 48 hrs. Then the mixture was diluted with DCM (250 mL) and washed with 5 weight % aqueous $K_2CO_3$ (200 mL) and then with saturated aqueous $K_2CO_3$ (500 mL). The resulting organic phase was collected and washed with 1M aqueous solution of $NaHSO_3$ (300 mL) and then with brine (200 mL). The organic phase was recovered, dried over $Mg_2SO_4$ and filtered. After evaporation of the solvent, 38 g of product was collected. MS analysis supported the molecular weight of the product (3-bromo-4-methoxyphenyl)(phenyl)methanone.

Step 2

The procedure of Step 1 of Example 5 of U.S. Pat. No. 7,465,415B2 was followed except that (3-bromo-4-methoxyphenyl)(phenyl)methanone was used in place of (4-fluorophenyl)(4-(2-hydroxyethoxy)phenyl)methanone to produce 1-(4-fluorophenyl)-1-(4-(3-(hydroxymethyl)piperidin-1-yl)phenyl)prop-2-yn-1-ol. The product was used without further purification.

PA-16

Step 1

The procedure of Step 1 of PA-15 was used except that (4-fluorophenyl)(4-methoxyphenyl)methanone was utilized instead of 4-methoxybenzophenone to obtain (3-bromo-4-methoxyphenyl)(4-fluorophenyl)methanone.

Step 2

Steps 2 to 3 of Example 7 of U.S. Pat. No. 7,465,415B2 were followed except that ((3-bromo-4-methoxyphenyl)(4-fluorophenyl)methanone was used in place of (4-fluorophenyl)(4-(2-hydroxyethoxy)phenyl)methanone to produce 1-(3-bromo-4-methoxyphenyl)-1-(4-morpholinophenyl) prop-2-yn-1-ol. The product was used without further purification.

PA-17

Steps 2 to 3 of Example 7 of U.S. Pat. No. 7,465,415B2 were followed except that (4-fluorophenyl)(4-methoxyphenyl)methanone was used in place of (4-fluorophenyl)(4-(2-hydroxyethoxy)phenyl)methanone and morpholin-2-ylmethanol was used instead of morpholine to produce 1-(4-(2-(hydroxymethyl)morpholino)phenyl)-1-(4-methoxyphenyl) prop-2-yn-1-ol. The product was used without further purification.

PA-18

Step 1 to 2 of PA-3 were followed except that piperidin-4-ylmethanol was used instead of piperidine 3-methanol to produce 1-(4-fluorophenyl)-1-(4-(4-(hydroxymethyl)piperidin-1-yl)phenyl)prop-2-yn-1-ol. The product was used without further purification.

PA-19

Step 1

Into a 0.5 L reaction flask was added DMF (200 mL), dihydroxybenzophenone (15 g) and $K_2CO_3$ (29 g). The resulting mixture was stirred under nitrogen atmosphere and allylbromide (48 mL) was added. The reaction was stirred for 12 hrs at 75° C. The mixture was filtered through filter paper and the filtrate collected. DCM (250 mL) was added, and the mixture was washed with water (5 times with 400 mL each time). The resulting organic layer was collected and the solvents evaporated to produce 19 g of product. MS analysis supported the molecular weight of bis(4-(allyloxy)phenyl)methanone.

Step 2

The product of step 1 was added to a 1 L reaction flask with 100 mL of DMF. The mixture was cooled to 5° C. with an ice bath and bubbled with acetylene gas for 10 min. A slurry of sodium acetylide (18% weight in Xylene/mineral oil from Aldrich, 22 mL) was added all at once. The reaction mixture was stirred for 0.5 hrs and then the ice bath was removed. After 10 hrs the mixture was poured into a flask containing ice (150 g) and stirred for 10 minutes. EtOAc (300 mL) was added and the mixture phase separated. During the phase separation a saturated solution of $NH_4Cl$ (250 mL) was added. The recovered organic layer was washed with water (2 times with 150 mL each time). The resulting solution was concentrated by rotary evaporation to provide 21 g of product. The product 1,1-bis(4-(allyloxy)phenyl)prop-2-yn-1-ol was used without further purification. The product was used without further purification.

PA-20

Step 1

The procedure of Step 1 of PA-19 was followed except that (4-fluorophenyl)(4-hydroxyphenyl)methanone was used instead of dihydroxybenzophenone to obtain (4-(allyloxy)phenyl)(4-fluorophenyl)methanone. MS analysis supported the molecular weight of the product.

Step 2

Steps 2 to 3 of Example 7 of U.S. Pat. No. 7,465,415B2 were followed except that (4-(allyloxy)phenyl)(4-fluorophenyl)methanone was used in place of (4-fluorophenyl)(4-(2-hydroxyethoxy)phenyl)methanone to produce 1-(4-(allyloxy)phenyl)-1-(4-morpholinophenyl)prop-2-yn-1-ol. The product was used without further purification.

PA-21

Steps 2 to 3 of Example 13 in US2006/0228557A1 were followed to produce 1-phenyl-1-(4-(2-hydroethoxy)phenyl)-2-propyn-1-ol. The product was used without further purification.

PA-22

Step 1

In a 500 mL dry flask, the product of Step 1 of PA-2 (4-(2-hydroxyethoxy)phenyl)(4-methoxyphenyl)methanone (8 g) was dissolved in dry DMF (100 mL) and NaH (5.6 g, 55% powder) was added. The mixture was stirred for 1 h under Nitrogen atmosphere and then allyl bromide (14.8 mL) was slowly added. After 12 hrs the reaction was quenched by addition of 50 mL of water. The resulting mixture was extracted with DCM (200 mL) and the collected organic phase washed with water (5 times with 250 mL each time). The solvent was evaporated to collect the residue. MS analysis supports the molecular weight of the product (4-(2-(allyloxy)ethoxy)phenyl)(4-methoxyphenyl)methanone (10 g).

Step 2

The procedure of Step 1 of Example 5 of U.S. Pat. No. 7,465,415B2 was followed except that (4-(2-(allyloxy)ethoxy)phenyl)(4-methoxyphenyl)methanone used in place of (4-fluorophenyl)(4-(2-hydroxyethoxy)phenyl)methanone to produce 1-(4-(2-(allyloxy)ethoxy)phenyl)-1-(4-methoxyphenyl)prop-2-yn-1-ol. The product was used without further purification.

PA-23

Step 1

Into a 0.5 L reaction flask was added DMF (200 mL), (4-hydroxyphenyl)(4-methoxyphenyl)methanone (15 g) and $K_2CO_3$ (27 g). The resulting mixture was stirred under nitrogen atmosphere and butylbromide (25 mL) was added. The reaction was stirred for 12 hrs at 75° C. The mixture was filtered through filter paper and the filtrate collected. DCM (250 mL) was added, and the mixture was washed with water (5 times with 400 mL each time). The resulting organic layer was collected and the solvents evaporated to produce 17 g of product. MS analysis supported the molecular weight of (4-butoxyphenyl)(4-methoxyphenyl)methanone.

Step 2

The procedure of step 1 of Example 5 of U.S. Pat. No. 7,465,415B2 was followed except that (4-butoxyphenyl)(4-methoxyphenyl)methanone used in place of (4-fluorophenyl)(4-(2-hydroxyethoxy)phenyl)methanone to produce 1-(4-butoxyphenyl)-1-(4-methoxyphenyl)prop-2-yn-1-ol. The product was used without further purification.

Part 2—Preparation of Naphthols (N) 1-27

N-1

Steps 1 to 5 of Example 1 in US2006/0228557A1 were followed to produce 2,3-dimethoxy-7,7-dimethyl-9-bromo-7H-benzo[C]fluoren-5-ol. MS analysis supported the molecular weight of the product.

N-2

Steps 1 to 6 in Example 1 in US2006/0228557A1 were followed to produce 2,3-dimethoxy-7,7-dimethyl-9-cyano- 7H-benzo[C]fluoren-5-ol. MS analysis supported the molecular weight of the product.

N-3

Step 1 in Example 2 in US2006/0228557A1 was followed to produce 2,3-dimethoxy-7,7-dimethyl-9-carboxy-7H-benzo[C]fluoren-5-ol. MS analysis supported the molecular weight of the product.

N-4

Step 4 in Example 7 in U.S. Pat. No. 7,465,415B2 was followed to produce 7,7-dimethyl-7H-benzo[c]fluoren-5-ol. MS analysis supported the molecular weight of the product.

N-5

Steps 3 to 6 in Example 1 in U.S. Pat. No. 7,527,754B2 were followed to produce 3,9-difluoro-7,7-dimethyl-7H-benzo[c]fluoren-5-ol. MS analysis supported the molecular weight of the product.

N-6

The product of Step 5 of Example 4 in U.S. Pat. No. 5,645,767 (10 g) was dissolved in dTHF (100 mL) in a 1 L reaction flask. The resulting solution was cooled to 0° C. in an ice bath. MeMgBr (65 mL of 1.4M in THF) was added through an addition funnel and the reaction mixture maintained in the ice bath for 1 h and then refluxed. After 3 h at reflux the reaction mixture was cooled to room temperature and quenched by adding small aliquots of saturated aqueous $NH_4Cl$ (5 times with 10 mL each time). The mixture was poured into a flask containing ice (150 g). The resulting mixture was extracted with EtOAc (250 mL). The recovered organic phase was washed with brine (100 mL) and then dried over $Mg_2SO_4$. After filtration and evaporation of the solvent the product 3,7,9-trimethyl-7H-benzo[c]fluorene-5,7-diol was collected (10.4 g). MS analysis supported the molecular weight of the product.

N-7

The procedure of Step 1 of Example 5 in US 2006/0228557A1 was used except that 4-trifluoromethylphenylboronic acid was used instead of 4-fluorophenylboronic acid to produce 2,3-dimethoxy-7,7-dimethyl-9-(4-(trifluoromethyl)phenyl)-7H-benzo[c]fluoren-5-ol. MS analysis supported the molecular weight of the product.

N-8

Step 1

The product of N-2 (10 g) 2,3-dimethoxy-7,7-dimethyl-9-cyano-7H-benzo[C]fluoren-5-ol, DHP (5 mL), PTSA (0.1 g) and DCM (250 mL) were combined in a 0.5 L reaction flask under a nitrogen atmosphere. The mixture was stirred for 4 h and then poured into saturated aqueous $Na_2CO_3$ (150 mL). The organic phase was collected and dried over $Mg_2SO_4$. After filtration and evaporation of the solvent, the product 2,3-dimethoxy-7,7-dimethyl-5-((tetrahydro-2H-pyran-2-yl)oxy)-7H-benzo[c]fluorene-9-carbonitrile (12 g) was collected and used in the next step without purification.

Step 2

The product of step 1 (12 g) was dissolved in tent-Butanol (200 mL) in a reaction flask and then KOH (4.8 g) and 1-bromoexane (10 g) were added. The mixture was refluxed for 6 hrs and cooled down to room temperature. After evaporation of the solvent the recovered residue was dissolved in EtOAc (400 mL) and washed with water (3 times with 150 mL each time). The resulting organic phase was collected and the solvent evaporated to provide the product N-hexyl-2,3-dimethoxy-7,7-dimethyl-5-((tetrahydro-2H-pyran-2-yl)oxy)-7H-benzo[c]fluorene-9-carboxamide (12 g) which was used as is for the next step.

Step 3

The product of Step 2 (12 g) was dissolved in MeOH (250 mL) in a reaction flask and HCl (37%, 0.5 mL) was added. The mixture was heated to reflux for 3 hrs and cooled down to room temperature. The solvent was evaporated by rotary evaporation and the recovered residue dissolved in DCM (200 mL), washed with water (100 mL) and then with brine (100 mL). The resulting organic phase was separated and after evaporation of the solvent the product (10 g) 2,3-dimethoxy-7,7-dimethyl-9-hexylcarbamoyl -7,4-benzo[C]fluoren-5-ol. MS analysis supported the molecular weight of the product.

N-9

In a dried reaction flask, piperidine-3-methanol (3 g) and the product of N-8 (3 g) were dissolved in dTHF (60 mL), the solution was cooled in an ice bath and n-BuLi (2M in cyclohexane, 35 mL) was slowly added using a syringe. The resulting mix was stirred 15 min in the ice bath and then refluxed for 3.5 hrs. The mixture was stirred overnight at room temperature. The reaction was quenched with water (25 mL) and saturated aqueous $NH_4Cl$ (40 mL). The mixture was extracted with EtOAc (100 mL) and the organic layer collected. After evaporation of the solvent, the product (3.4 g) was collected. NMR analysis showed the product to have a structure consistent with 2-(3-(hydroxymethyl)piperidin-1-yl)-,3-dimethoxy-7,7-dimethyl-9-hexylcarbamoyl -7H-benzo[C]fluoren-5-ol.

N-10

The procedure of Step 6 of Example 5 in U.S. Pat. No. 7,557,208 was followed except that piperidine was used instead of morpholine to produce 3-methoxy-7,7-dimethyl-2-(piperidin-1-yl)-7H-benzo[c]fluoren-5-ol. MS analysis supported the molecular weight of the product.

N-10

Steps 1 to 6 of Example 1 in US2008/0103301A1 were followed to produce 2,3-dimethoxy-7,7-dimethyl-9-(trifluoromethyl)-7H-benzo[c]fluoren-5-ol. MS analysis supported the molecular weight of the product.

N-12

Step 1 of Example 9 in US2006/0228557A1 was followed to produce 2,3-dimethoxy-7,7-dimethyl-9-(phenylethynyl)-7,4-benzo[c]fluoren-5-ol. MS analysis supported the molecular weight of the product.

N-13

Step 1

The procedure of Step 1 of Example 5 in US 2006/0228557A1 was used except that 2-trifluoromethylphenylboronic acid was used instead of 4-fluorophenylboronic acid to produce 2,3-dimethoxy-7,7-dimethyl-9-(2-(trifluoromethyl)phenyl)-7H-benzo[c]fluoren-5-ol. MS analysis supported the molecular weight of the product.

Step 2

The procedure of Step 6 Example 5 in U.S. Pat. No. 7,557,208 was used except that 3-dimethoxy-7,7-dimethyl-9-(2-(trifluoromethyl)phenyl)-7H-benzo[c]fluoren-5-ol was used instead of 2,3-dimethoxy-7,7-dimethyl-7H-benzo[c]fluoren-5-ol to produce 3-methoxy-7,7-dimethyl-2-(piperidin-1-yl)-9-(2-(trifluoromethyl)phenyl)-7H-benzo[c]fluoren-5-ol. MS analysis supported the molecular weight of the product.

N-14

The procedure of Step 6 of Example 5 in U.S. Pat. No. 7,557,208 was used except that piperidine 3-methanol was used instead of morpholine to produce 2-(3-(hydroxymethyl)piperidin-1-yl)-3-methoxy-7,7-dimethyl-7H-benzo[c]fluoren-5-ol. MS analysis supported the molecular weight of the product.

N-15

The procedure of Step 1 of Example 5 in US 2006/0228557A1 was used except that 4-cyanophenylboronic acid was used instead of 4-fluorophenylboronic acid to produce 9-(4-cyanophenyl)-2,3-dimethoxy-7,7-dimethyl-7H-benzo[c]fluoren-5-ol. MS analysis supported the molecular weight of the product.

N-16

The procedure of Step 6 of Example 5 in U.S. Pat. No. 7,557,208 was used except that the product from Steps 1 to 6 of Example 1 in US2008/0103301A1 was used instead of 2,3-dimethoxy-7,7-dimethyl-7H-benzo[c]fluoren-5-ol and N,N-diethylamine instead of piperidine was used to produce 2-(diethylamino)-3-methoxy-7,7-dimethyl-9-(trifluoromethyl)-7H-benzo[c]fluoren-5-ol. MS analysis supported the molecular weight of the product.

N-17

The procedure of Step 6 of Example 5 in U.S. Pat. No. 7,557,208 was used except that the product from Step 1 of Example 6 from US 2006/0228557A1 2,3-dimethoxy-7,7-dimethyl-9-phenyl-7H-benzo[c]fluoren-5-ol was used instead of 2,3-dimethoxy-7,7-dimethyl-7H-benzo[e]fluoren-5-ol to produce 3-methoxy-7,7-dimethyl-9-phenyl-2-(piperidin-1-yl)-7H-benzo[c]fluoren-5-ol. MS analysis supported the molecular weight of the product.

N-18

The procedure of N-21 was followed except that morpholine was used instead of piperidine to produce 3-methoxy-7,7-dimethyl-2-morpholino-9-phenyl-7H-benzo[c]fluoren-5-ol. MS analysis supported the molecular weight of the product.

N-19

The product of N-3 (1.5 g) was dissolved in dTHF (50 mL) in a reaction flask and cooled to 5° C. in an ice bath. Then the solution of $BH_3$-THF complex 1M in THF (12 mL) was slowly added and the resulting mixture was stirred at room temperature under a nitrogen atmosphere for 12 hrs. Water (30 mL) was added and the resulting mixture was extracted with EtOAc (100 mL). After evaporation of the solvent, the product 9-(hydroxymethyl)-2,3-dimethoxy-7,7-dimethyl-7H-benzo[c]fluoren-5-ol was collected (1.2 g) and used without further purification.

N-20

Step 1

The procedure of Steps 1 to 5 of Example 1 in U.S. Pat. No. 5,645,767 were followed except that bis(4-methoxyphenyl)methanone was used in place of 4,4'dimethylbenzophenone to produce 5-hydroxy-3,9-dimethoxy-7H-benzo[c]fluoren-7-one.

Step 2

The product of Step 1 (5 g) was dissolved in dTHF (70 mL) in a reaction flask. The resulting solution was cooled to 0° C. in an ice bath. n-BuLi (2.5M in Hexanes, 20 mL) was added and the reaction mixture maintained in the ice bath for 1 h and then warmed up to room temperature. After 2 h the reaction mixture was quenched by adding small aliquots of saturated aqueous $NH_4Cl$ (40 mL). The mixture was poured into a flask containing ice (100 g). The resulting mixture was extracted with EtOAc (150 mL). The recovered organic phase was washed with brine (100 mL) and then dried over $Mg_2SO_4$. After filtration and evaporation of the solvent the product 7-butyl-3,9-dimethoxy-7H-benzo[c]fluorene-5,7-diol was collected (5.5 g). MS analysis supported the molecular weight of the product.

N-21

Step 1

A mixture of the product of Step 5 of Example 4 in U.S. Pat. No. 5,645,767 (20 g) 3,9-dimethyl-5-hydroxy-7H-benzo[C]fluoren-7-one, hydrazine hydrate (50-60%, 130 g), anhydrous $K_2CO_3$ (168 g) and diethylene glycol (600 mL) in a 2 L reaction flask was heated to reflux (approx 190° C.) for 6 hrs. The solution was cooled to room temperature and water (350 mL) was added. The resulting mixture was poured into aqueous HCl (6M, 400 mL) and extracted with EtOAc (2 times with 500 mL each time). The organic phase was collected and washed with brine (250 mL). After evaporation of the solvent the product 3,9-dimethyl-7H-benzo[c]fluoren-5-ol (15 g) was collected.

Step 2

Product from Step 1 (5 g) was dissolved in dry diethyl ether (150 mL) in a reaction flask and the resulting solution cooled to −50° C. in a bath of dry ice in acetone. n-BuLi (2.5M in Hexanes, 17 mL) was slowly added. The mixture was stirred for 10 minutes in the cold bath and then 1 h at room temperature. The reaction mixture was poured into crushed dry ice (30 g). Water was added (40 mL) and the solution brought to neutral pH using diluted HCl. The mixture was extracted with EtOAc (300 mL) and the organic phase collected. Evaporation of the solvent yielded the product 5-hydroxy-3,9-dimethyl-7H-benzo[c]fluorene-7-carboxylic acid (4.5 g) which was used in the next step without further purification.

Step 3

The product of Step 2 (4.5 g) was dissolved in MeOH (200 mL) and 3 drops of $H_2SO_4$ were added. The mixture was heated to reflux for 3 hrs and cooled to room temperature. After evaporation of the solvent, the resulting residue was dissolved in DCM (150 mL) and washed with brine (50 mL). The organic layer was collected and the solvent evaporated to afford the product methyl 5-hydroxy-3,9-dimethyl-7H-benzo[c]fluorene-7-carboxylate (4.5 g). MS analysis supported the molecular weight of the product.

N-22

Step 1

Bromo(3-methoxyphenyl)magnesium (1M in THF, 98 mL) was poured into a dry 1 L flask and the mix cooled in an ice bath. Bis[2-(N,N-dimethylamino)-ethyl]ether (18.6 mL) was added in one portion while stirring. After 25 min the solution was slowly added to a chilled solution of 4-biphenyl carbonyl chloride (21 g) in dTHF (40 mL). After 10 min the ice bath was removed and the reaction was mixed at room temperature for 12 hrs. Water (150 mL) was added to the reaction mixture, and the pH adjusted to 5 with HCl conc. (10 mL). The mixture was extracted using EtOAc (2 times with 300 mL each time). The recovered organic fraction was then washed with water (200 mL), brine (200 mL) and dried over $Mg_2SO_4$. After filtration and evaporation of the solvent the product (28 g) was collected. MS analysis supported the molecular weight of [1,1-biphenyl]-4-yl(3-methoxyphenyl) methanone.

Step 2

Steps 1 to 5 of Example 1 in US2006/0228557A1 were followed except that [1,1'-biphenyl]-4-yl(3-methoxyphenyl) methanone was used in place of 3,4-dimethoxy-4'-bromobenzophenone to produce 2-methoxy-7,7-dimethyl-9-phenyl-7H-benzo[c]fluoren-5-ol. MS analysis supported the molecular weight of the product.

N-23

Steps 1 to 5 in Example 1 in US2006/0228557A1 were followed except that [1,1'-biphenyl]-4-yl(3-methoxyphenyl) methanone was used in place of 3,4-dimethoxy-4'-bromobenzophenone and in Step 4 ethyl lithium was used instead of methyl magnesium chloride to produce 7,7-diethyl-2-methoxy-9-phenyl-7H-benzo[c]fluoren-5-ol. MS analysis supported the molecular weight of the product.

N-24

Step 1

Into a 1 L reaction flask containing acetic anhydride (600 mL) was added 7,7-dimethyl-7H-benzo[c]fluoren-5-ol (150 g) followed by the addition of, 4-dimethylaminopyridine (DMAP) (0.2 g). The reaction mixture was heated to 130° C. and maintained at this temperature for 2 to 3 hours. The resulting reaction mixture was cooled to 120° C. and maintained at this temperature overnight and cooled to room temperature prior to being poured into ice water and stirred for 2 hours. An off-white solid formed and was collected by filtration. The recovered solid was washed with water, and then with MeOH/water (v/v, 50/50). The product 7,7-dimethyl-7H-benzo[c]fluoren-5-yl acetate was air-dried to yield 175 g solid and was used in the next step without further purification.

Step 2

Into a 1 L reaction flask containing 400 mL of DMF was added the product of Step 1 (120 g) followed by the addition of N-bromosuccinimide (NBS, 82 g). The reaction mixture was heated to 90° C., spiked to 120° C. briefly and returned to about 95° C. and was heated at this temperature for 4 hours. Additional NBS was added (8 g) and the reaction mixture was heated for 2 more hours. The resulting reaction mixture was poured into water and was extracted with EtOAc. The recovered organic layer was washed with water (3×200 mL), dried over $MgSO_4$ and concentrated under vacuum to provide product. The product was slurried in MeOH and the solid was recovered by filtration, washed with MeOH (3×200 mL) and dried to provide a light yellowish solid (107 g). The product 9-bromo-7,7-dimethyl-7H-benzo[c]fluoren-5-yl acetate was used in the next step without purification.

Step 3

Into a 1 L reaction flask containing MeOH (500 mL) was added the product of Step 2 (107 g) followed by the addition of conc. HCl, 37% (3 g). The reaction mixture was heated to reflux for 2 hours. The solvents were removed from the resulting reaction mixture to yield about 100 g solid. The recovered solid was slurried in about 250 mL of DCM/Hexanes (v/v, 50/50) for 10 minutes at room temperature. The slurry was filtered and the recovered solid was washed with DCM/Hexanes (v/v, 5/5) to provide about 47 g of product. NMR analysis showed the product to have a structure consistent with 7,7-dimethyl-9-bromo-7H-benzo[c]fluoren-5-ol.

Step 4

The product of Step 3 (3 g) and 4-methoxy phenyl boronic acid (2 g) were added to a 0.5 L reaction flask containing a solution of dimethoxyethane (150 mL) and water (50 mL) followed by the addition of $K_2CO_3$ (3.7 g) and triphenylphosphine (1.15 g). The resulting solution was bubbled with nitrogen for 10 minutes and then palladium acetate (0.2 g) was added to the reaction mixture. The reaction mixture was heated to reflux under a nitrogen atmosphere. After 4 h, the reaction mixture was cooled to room temperature and poured into 400 mL of water followed by extraction with EtOAc (2×150 mL). The recovered organic layers were combined and washed with brine (200 mL). This organic layer was dried over $Mg_2SO_4$ and, after filtration and evaporation of the solvents yielded the product (3.5 g) which was used in the next step without purification. MS analysis supported the molecular weight of the product 9-(4-methoxyphenyl)-7,7-dimethyl-7H-benzo[c]fluoren-5-ol.

N-25

The procedure of Step 4 of N-30 was followed except that 4-dimethylaminophenyl boronic acid instead of 4-methoxy phenyl boronic acid was used to produce 9-(4-(dimethylamino)phenyl)-7,7-dimethyl-7H-benzo[c]fluoren-5-ol. The product was used without purification.

N-26

The procedure of Step 4 of N-30 was followed except that 2-methoxy phenyl boronic acid instead of 4-methoxy phenyl boronic acid was used to produce 9-(2-methoxyphenyl)-7,7-dimethyl-7H-benzo[c]fluoren-5-ol. The product was used without purification.

N-27

Step 1

Steps 2 to 5 of Example 10 in US 2006/0228557A1 were followed except that [1,1'-biphenyl]-4-yl(3-methoxyphenyl)methanone was used in place of 3,4-dimethoxy-4'-phenhyl-benzophenone to produce 2-methoxy-7-oxo-9-phenyl-7H-benzo[c]fluoren-5-yl acetate.

Step 2

Product from Step 1 (15g) was dissolved in MeOH (200 mL) in a reaction flask and HCl (36%, 0.5 mL) was added. The mixture was refluxed for 3 hrs and cooled to room temperature. The solvent was evaporated, the resulting residue dissolved in DCM (150 mL) and washed with brine (80 mL). After evaporation of the solvent, the product 5-hydroxy-2-methoxy-9-phenyl-7H-benzo[c]fluoren-7-one (14g) was collected. The product was used without purification.

Part 3—Preparation of Photochromic Intermediates

Comparative Examples (CE) 1-73

CE-1

Example 5 in U.S. Pat. No. 5,645,767 was followed to produce 3,3-(di(4-methoxyphenyl)-6,11,13-trimethyl-13-hydroxy-3H -13H indeno[2,1-f]naphtho[1,2-b]pyran. The structure was supported by NMR analysis.

CE-2

Example 2 at column 86, lines 30 to 51 in U.S. Pat. No. 7,465,415B2 was followed to produce 3,3-(di(4-methoxyphenyl)-6,1,13-trimethyl-13-(2-(2-(2-hydroxyethoxy)ethoxy)ethoxy)-3H,13H indeno[2,1-f]naphtho[1,2-b]pyran. The structure was supported by NMR analysis.

CE-3

The procedure of Example 2 at column 86, lines 30 to 51 in U.S. Pat. No. 7,465,415B2 was followed except that ethylene glycol was used in place of triethylene glycol to produce 3,3-(di(4-methoxyphenyl)-6,11,13-trimethyl-13-(2-hydroxyethoxy)-3H,13H indeno[2,1-f]naphtho[1,2-b]pyran. The structure was supported by NMR analysis.

CE-4

The procedure from Example 2 at column 86, lines 30 to 51 in U.S. Pat. No. 7,465,415B2 was followed except that allyl alcohol was used in place of triethylene glycol to produce 3,3-(di(4-methoxyphenyl)-6,11,13-trimethyl-13-(allyloxy)-3H,13H indeno[2,1-f]naphtho[1,2-b]pyran. The structure was supported by NMR analysis.

CE-5

Step 1

Into a 0.5 L reaction flask the product N-6 (4.6 g) and product PA-2 (6.2 g) were dissolved in DCM (300 mL). PTSA (0.15 g) was added and the mixture was stirred at room temperature for 4 hrs. The reaction mixture was washed with water (200 mL) and then the solvent was evaporated. The resulting residue was purified by column chromatography eluting with DCM/EtOAc (4/1, V/V) to provide the product (7.3 g).

NMR analysis showed the product to have a structure consistent with 34442-hydroxyethoxy)phenyl)-3-(4-methoxyphenyl)-6,11,13-trimethyl-13-hydroxy-3H,13H indeno[2,1-f]naphtho[1,2-b]pyran.

Step 2

The procedure from Example 2 at column 86, lines 30 to 51 in U.S. Pat. No. 7,465,415, B2 was followed except that product from Step 1 was used in place of 3,3-di(4-methoxyphenyl)-6,11,13-trimethyl-13-hydroxy-3H,13H-indeno[2,1-f]naphtho[1,2-b]pyran to produce 3-(4-(2-hydroxyethoxy)phenyl)-3-(4-methoxyphenyl)-6,11,13-trimethyl-13-(2-(2-(2-hydroxyethoxy)ethoxy)ethoxy)-3H,13H indeno[2,1-f]naphtho[1,2-b]pyran. The structure was supported by NMR analysis.

CE-6

The procedure of Example 2 in US2006/0228557A1 was followed to produce 3,3-di(4-methoxyphenyl)-6,7-dimethoxy-11-carboxy-13,13-dimethyl-3H,13H indeno[2',2':3,4]naphtho[1,2-b]pyran. The structure was supported by NMR analysis.

CE-7

Step 1

The procedure of CE-4 was employed except that the product of Step 1 in CE-5 was used instead of 3,3-di(4-methoxyphenyl)-6,11,13-trimethyl-13-hydroxy-3H,13H-indeno[2,1-f]naphtho[1,2-b]pyran to produce 3-(4-(2-hydroxyethoxy)phenyl)-3-(4-methoxyphenyl)-6,11,13-trimethyl-13-(allyloxy)-3H,13H indeno[2,1-f]naphtho[1,2-b]pyran. The structure was supported by NMR analysis.

Step 2

Into a 300 mL flask, the product from Step 1 (0.8 g) was dissolved in DCM (13 mL) and then ε-caprotactone monomer (1.7 mL) and aluminum isopropoxide catalyst (0.1 g) were added. The reaction mixture was stirred at room temperature for 14 hrs. Aqueous HCl (5%, 10 mL) was added and after stirring for 30 minutes the mixture was washed with water (20 mL). The resulting organic phase was collected and the solvent evaporated. The residue was filtered through a silica plug and then collected. After evaporation of the solvent, the product was dissolved in DCM (5 mL) and precipitated by adding hexanes (60 mL). After filtration the final product (0.6 g) was collected. NMR analysis showed the product to have a structure consistent with the starting material in which 5-6 caprolacton units polymerized.

CE-8

Step 1

Into a 0.5 L reaction flask, product N-21 (4.5 g) and product PA-4 (4.6 g) were dissolved in DCM (300 mL). PTSA (0.10 g) was added and the mixture was stirred at room temperature for 12 hrs. The reaction mixture was washed with water (200 mL) and the solvent evaporated. The resulting residue was purified by column chromatography eluting with DCM/EtOAc (5/1, V/V) to afford the product (8.0 g). The product 3-(4-morpholinophenyl)-3-(4-methoxyphenyl)-6,11-dimethyl-13-(methoxycarbonyl)-3H,13H indeno[2,1-f]naphtho[1,2-b]pyran was used without further purification in the next step.

Step 2

Into a dry 0.5 L reaction flask, the product of Step 1 (8.0 g) was dissolved in dry acetone (250 mL) and dry $K_2CO_3$ (10g) was added. The mixture was stirred and 11-bromo-1-undecanol (10g) was added. The mixture was heated to reflux and after 15 hrs cooled to room temperature. After filtration, the filtrate was collected and the solvent evaporated. The residue was purified by column chromatography eluting with DCM/EtOAc 5/1. The fractions containing the product were collected to provide the product (8.0 g). NMR analysis showed the product to have a structure consistent with 3-(4-morpholinophenyl)-3-(4-methoxyphenyl)-6,11-dimethyl-13-(11-hydroxyundecyl)-13-(methoxycarbonyl)-3H,13H indeno[2,1-f]naphtho[1,2-b]pyran.

CE-9

Step 1

The procedure described in Step 7 of Example 10 in US 2006/0228557 was followed except that compound N-20 was used in place of 2,3-dimethoxy-7-hydroxy-7-ethyl-1'-phenyl-7H-benzo-[C]fluoren-5-ol to produce 3,3-(di(4-methoxyphenyl)-6,11-dimethoxy-13-butyl-13-hydroxy-3H,13H indeno[2,1-f]naphtho[1,2-b]pyran. The structure was supported by NMR analysis.

Step 2

The procedure from Example 2 at column 86, lines 30 to 51 in U.S. Pat. No. 7,465,415B2 was followed except that product from Step 1 was used in place of 3,3-di(4-methoxyphenyl)-6,11,13-trimethyl-13-hydroxy-3H,13H-indeno[2,1-f]naphtho[1,2-b]pyran and ethylene glycol was used in place of triethylene glycol to produce 3,3-(di(4-methoxyphenyl)-6,11-dimethoxy-13-butyl-13-(2-hydroxyethoxy)-3H,13H indeno[2,1-f]naphtho[1,2-b]pyran. The structure was supported by NMR analysis.

CE-10

The procedure described in Step 4 of Example 13 of US2006/0228557A1 was followed except that product N-5 was used in place of 3-methoxhy-9-bromo-7,7-dimethyl-7H-benzo[C]fluoren-5-ol to produce 3-(4-(2-hydroxyethoxy)phenyl)-3-phenyl-6,11-difluoro-13,13-dimethyl-3H,13H indeno[2,1-f]naphtho[1,2-b]pyran. The structure was supported by NMR analysis.

CE-11

The procedure used in Step 1 of CE-5 was followed except that product N-8 was used in place of product N-6 to produce 3-(4-(2-hydroxyethoxy)phenyl)-3-(4-methoxyphenyl)-6,7-dimethoxy-11-hexylcarbamoyl-13,13-dimethyl-3H,13H indeno[2',3':3,4]naphtho[1,2-b]pyran. The structure was supported by NMR analysis.

CE-12

The procedure of Step 5 of Example 7 of U.S. Pat. No. 7,465,415B2 was followed to produce 3-(4-(2-hydroxyethoxy)phenyl)-3-(4-morpholinophenyl)-13,13-dimethyl-3H,13H indeno[2,1-f]naphtho[1,2-b]pyran. The structure was supported by NMR analysis.

CE-13

The procedure of Step 5 of Example 7 of U.S. Pat. No. 7,465,415B2 was followed except that product N-22 was used instead of 4,7,7-dimethyl-5-hydroxy-7Hbenzo[C]fluorene to produce 3-(4-(2-hydroxyethoxy)phenyl)-3-(4-morpholinophenyl)-7-methoxy-11-phenyl-13,13-dimethyl-3H,13H indeno[2,1-f]naphtho[1,2-b]pyran. The structure was supported by NMR analysis.

CE-14

The procedure used in Step 1 of CE-5 was followed except that product N-25 was used in place of product N-6 to produce 3-(4-(2-hydroxyethoxy)phenyl)-3-(4-methoxyphenyl)-11-(4-(dimethylamino)phenyl)-13,13-dimethyl-3H,13H indeno[2',3':3,4]naphtho[1,2-b]pyran. The structure was supported by NMR analysis.

CE-15

The procedure used in Step 1 of CE-5 was followed except that product N-19 was used in place of product N-6 and product PA-22 instead of product PA-2 to produce 3-(4-(2-(allyloxy)ethoxy)phenyl)-3-(4-methoxyphenyl)-6,7-dimethoxy-11-(hydroxymethyl)-13,13-dimethyl-3H,13H indeno[2',3':3,4]naphtho[1,2-b]pyran. The structure was supported by NMR analysis.

CE-16

The procedure used in Step 1 of CE-5 was followed except that product N-10 was used in place of product N-6 to 3-(4-(2-hydroxyethoxy)phenyl)-3-(4-methoxyphenyl)-6-methoxy-7-(piperidin1-yl)-13,13-dimethyl-3H,13H indeno[2',3':3,4]naphtho[1,2-b]pyran. The structure was supported by NMR analysis.

CE-17

The procedure used in Step 1 of CE-5 was followed except that product N-24 was used in place of product N-6 to produce 3-(4-(2-hydroxyethoxy)phenyl)-3-(4-methoxyphenyl)-11-(4-methoxhyphenyl)-13,13-dimethyl-3H,13H indeno[2',3'3,4]naphtho[1,2-b]pyran. The structure was supported by NMR analysis.

CE-18

The procedure used in Step 1 of CE-5 was followed except that product N-25 was used in place of product N-6 and product PA-6 instead of product PA-2 to produce produce 3-(4-(2-hydroxyethoxy)phenyl)-3-(4-fluorophenyl)-11-(4-

(dimethylamino)phenyl)-13,13-dimethyl-3H,13H indeno[2',3':3,4]naphtho[1,2-b]pyran. The structure was supported by NMR analysis.

CE-19

The procedure used in Step 1 of CE-5 was followed except that product N-26 was used in place of product N-6 to produce 3-(4-(2-hydroxyethoxy)phenyl)-3-(4-methoxyphenyl)-11-(2-methoxyphenyl)-13,13-dimethyl-3H,13H indeno[2',3':3,4]naphtho[1,2-b]pyran. The structure was supported by NMR analysis.

CE-20

The procedure used in Step 1 of CE-5 was followed except that product N-9 was used in place of product N-6 and product PA-22 instead of product PA-2 to produce 3-(4-(2-(allyloxy) ethoxy)phenyl)-3-(4-methoxyphenyl)-6-methoxy-7-(3-(hydroxymethyl)piperidin-1-yl)-11-hexylcarbamoyl -13,13-dimethyl-3H,13H indeno[2',3':3,4]naphtho[1,2-b]pyran. The structure was supported by NMR analysis.

CE-21

The procedure described in Step 2 of CE-7 was followed except that product CE-47 was used in place of 2-(4-(13-(allyloxy)-3-(4-methoxyphenyl)-6,11,13-trimethyl-3,13-dihydrobenzo[h]indeno[2,1-f]chromen-3-yl)phenoxy)ethanol. NMR analysis shows a product with a structure consistent with the starting material in which 9 caprolactone units polymerized at the hydroxyl functionality.

CE-22

The procedure described in Step 7 of Example 10 in US 2006/0228557A1 was followed except that compound N-19 was used in place of 2,3-dimethoxy-7-hydroxy-7-ethyl-11phenyl-7H-benzo-[C]fluoren-5-ol to produce 3,3-(di(4-methoxyphenyl)-6,7-dimethoxy-11-(hydroxymethyl)-13,13-dimethyl-3H,13H indeno[2',3':3,4]naphtho[1,2-b]pyran. The structure was supported by NMR analysis.

CE-23

The procedure of Example 7 of US 2006/0228557A1 was followed to produce 3,3-(di(4-methoxyphenyl)-6,7-dimethoxy-11-(4-(hydroxymethyl)phenyl)-13,13-dimethyl-3H,13H indeno[2',3':3,4]naphtho[1,2-b]pyran. The structure was supported by NMR analysis.

CE-24

The procedure described in Step 7 of Example 10 in US 2006/0228557A1 was followed except that compound N-14 was used in place of 2,3-dimethoxy-7-hydroxy-7-ethyl-11phenyl-7H-benzo-[C]fluoren-5-ol to produce 3,3-(di(4-methoxyphenyl)-6-methoxy-7-(3-(hydroxymethyl)piperidin-1-yl)-13,13-dimethyl-3H,13H indeno[2',3':3,4]naphtho[1,2-b]pyran. The structure was supported by NMR analysis.

CE-25

The procedure of Step 1 of Example 12 of US 2006/0228557A1 was followed. to produce 3,3-di(4-methoxyphenyl)-6,7-dimethoxy-11-bromo-13,13-dimethyl-3H,13H indeno[2',3':3,4]naphtho[1,2-b]pyran. The structure was supported by NMR analysis.

CE-26

The procedure of Step 5 of Example 7 of U.S. Pat. No. 7,465,415B2 was followed except that product N-22 was used instead of 4,7,7-dimethyl-5-hydroxy-7Hbenzo[C]fluorene and product PA-3 instead of 1-(4-(2-hydroxyethoxy) phenyl)-1-(4-morpholinophenyl)prop-2-yn-1-ol to produce 3-(4-fluorophenyl)-3-(4-(3-(hydroxymethyl)piperidin-1-yl) phenyl)-7-methoxy-11-phenyl-13,13-dimethyl-3H,13H indeno[2,1-f]naphtho[1,2-b]pyran. The structure was supported by NMR analysis.

CE-27

The procedure used in Step 1 of CE-5 was followed except that product N-22 was used in place of product N-6 to produce 3-(4-(2-hydroxyethoxy)phenyl)-3-(4-methoxyphenyl)-7-methoxy-11-phenyl-13,13-dimethyl-3H,13H indeno[2,1-f]naphtho[1,2-b]pyran. The structure was supported by NMR analysis.

CE-28

Into a 0.5 L reaction flask, the product of Step 1 from CE-5 (2.9 g) was dissolved in MeOH (100 mL) and then PTSA (40 mg) was added. The mixture heated to 50° C. for 10 hrs. The reaction mixture was poured into water (200 mL) and filtered to collect the solid product (2.5 g). NMR analysis showed the product to have a structure consistent with 3-(4-(2-hydroxyethoxy)phenyl)-3-(4-methoxyphenyl)-6,11,13-trimethyl-13-methoxy-3H,13H indeno[2,1-f]naphtho[1,2-b]pyran.

CE-29

In a 0.3 L reaction flask, the product CE-28 (1.5 g) and succinnic anhydride (2.0 g) were dissolved in toluene (50 mL). 4-DMAP (30 mg) was added and the mixture heated to reflux for 4 hrs. The reaction mixture was cooled to room temperature and filtered. The filtrate was purified by column chromatography on silica gel eluting with hexanes/DCM (1/1, V/V) and then with MeCN/DCM (1/4, V/V). Fractions containing product were combined and evaporated to provide the product (1.46 g). NMR analysis showed the product to have s structure consistent with 3-((2-((3-carboxypropanoyl) oxy)ethoxy)phenyl)-3-(4-methoxyphenyl)-6,11,13-trimethyl-13-methoxy-3H,13H indeno[2,1-f]naphtho[1,2-b]pyran.

CE-30

The procedure used in Step 1 of CE-5 was followed except that product N-5 was used in place of product N-6 to produce 3-(4-(2-hydroxyethoxy)phenyl)-3-(4-methoxhyphenyl)-6,11-difluoro -13,13-dimethyl-3H,13H indeno[2,1-f]naphtho [1,2-b]pyran. The structure was supported by NMR analysis.

CE-31

The procedure used for the preparation of CE-29 was used except that CE-30 was used instead of CE-28 to produce 3-((2-((3-carboxypropanoyl)oxy)ethoxy)phenyl)-3-(4- methoxyphenyl)-6,11-difluoro-13,13-dimethyl-3H,13H indeno[2,1-f]naphtho[1,2-b]pyran. The structure was supported by NMR analysis.

CE-32

The procedure of Step 7 of Example 1 in U.S. Pat. No. 7,527,754B2 was used except that product PA-10 was used in place of 1-(fluorophenyl)-1-(4-piperidinophenyl)-2-propyn-1ol to produce 3-(4-(3-(hydroxymethyl)piperidin-1-yl)phenyl)-3-phenyl-6,11-difluoro-13,13-dimethyl-3H,13H indeno[2,1-f]naphtho[1,2-b]pyran. The structure was supported by NMR analysis.

CE-33

The procedure used in Step 1 CE-5 was followed except that product N-4 was used in place of product N-6 to produce 3-(4-(2-hydroxyethoxy)phenyl)-3-(4-methoxhyphenyl)-13,13-dimethyl-3H,13H indeno[2,1-f]naphtho[1,2-b]pyran. The structure was supported by NMR analysis.

CE-34

The procedure of Step 5 of Example 7 of U.S. Pat. No. 7,465,415B2 was followed except that product N-18 was used instead of 4,7,7-dimethyl-5-hydroxy-7Hbenzo[C]fluorene to produce 3-(4-(2-hydroxyethoxy)phenyl)-3-(4-morpholinophenyl)-6-methoxy-7-morpholino-11-phenyl-13,13-dimethyl-3H,13H indeno[2,1-f]naphtho[1,2-b]pyran. The structure was supported by NMR analysis.

CE-35

The procedure used in Step 1 of CE-5 was followed except that product N-11 was used in place of product N-6 to produce 3-(4'-(2-hydroxyethoxy)phenyl)-3-(4-methoxyphenyl)-6,7-dimethoxy-11-(trifluoromethyl)-13,13-dimethyl-3H,13H indeno[2',3':3,4]naphtho[1,2-b]pyran. The structure was supported by NMR analysis.

CE-36

The procedure described in Step 5 of Example 7 of U.S. Pat. No. 7,465,415B2 was followed except that product PA-3 was used in place of 1-(4-(2-hydroxyethoxy)phenyl)-1-(4-morpholinophenyl)prop-2-yn-1-ol to produce 3-(4-fluorophenyl)-3-(4-(3-(hydroxymethyl)piperidin-1-yl)phenyl)-13,13-dimethyl-3H,13H indeno[2,1-f]naphtho[1,2-b]pyran. The structure was supported by NMR analysis.

CE-37

The procedure used for the preparation of CE-29 was used except that CE-13 was used instead of CE-28 to produce 3-((2-(3-carboxypropanoyl)oxy)ethoxy)phenyl)-3-(4-morpholinophenyl)-7-methoxhy-11-phenyl-13,13-dimethyl-3H,13H indeno[2,1-f]naphtho[1,2-b]pyran. The structure was supported by NMR analysis.

CE-38

The procedure of Step 5 of Example 7 of U.S. Pat. No. 7,465,415B2 was followed except that product N-22 was used instead of 4,7,7-dimethyl-5-hydroxy-7Hbenzo[C]fluorene and product PA-8 instead of 1-(4-(2-hydroxyethoxy)phenyl)-1-(4-morpholinophenyl)prop-2-yn-1-ol to produce 3-(4-fluorophenyl)-3-(4-(4-hydroxypiperidin-1-yl)phenyl)-7-methoxy-11-phenyl-13,13-dimethyl-3H,13H indeno[2,1-f]naphtho[1,2-b]pyran. The structure was supported by NMR analysis.

CE-39

The procedure described in Step 5 of Example 7 of U.S. Pat. No. 7,465,415B2 was followed except that product PA-8 was used in place of 1-(4-(2-hydroxyethoxy)phenyl)-1-(4-morpholinophenyl)prop-2-yn-1-ol to produce 3-(4-fluorophenyl)-3-(4-(4-hydroxypiperidin-1-yl)phenyl)-13,13-dimethyl-3H,13H indeno[2,1-f]naphtho[1,2-b]pyran. The structure was supported by NMR analysis.

CE-40

Step 1

The procedure described in Step 7 of Example 10 in US 2006/0228557 was followed except that the product from Step 1 of N-20 was used in place of 2,3-dimethoxy-7-hydroxy-7-ethyl-11-phenyl-7H-benzo-[C]fluoren-5-ol to produce 3,3-(di(4-methoxyphenyl)-6,11-dimethoxy-13-oxo-3H,13H indeno[2,1-f]naphtho[1,2-b]pyran. The structure was supported by NMR analysis.

Step 2

A mixture of product of Step 1 (4 g), hydrazine hydrate (50-60%, 12 g), anhydrous $K_2CO_3$ (14 g) and diethylene glycol (80 mL) in a 1 L reaction flask was heated to reflux (approx 190° C.) for 5 hrs. The solution was cooled to room temperature and water (150 mL) was added. The resulting mixture was poured into aqueous HCl (6M, 50 mL) and extracted with EtOAc (2 times with 150 mL each time). The resulting organic phase was collected and washed with brine (100 mL). After evaporation of the solvent the product 3,3-(di(4-methoxyphenyl)-6,11-dimethoxy-3H,13H indeno[2,1-f]naphtho[1,2-b]pyran. The structure was supported by NMR analysis.

Step 3

Product from Step 2 (3.2 g) was dissolved in dry diethyl ether (100 mL) in a reaction flask and the resulting solution cooled to −50° C. in a bath of dry ice in acetone. n-BuLi (2.5M in Hexanes, 2.7 mL) was slowly added. The mixture was stirred for 10 minutes in the cold bath and then 45 minutes at room temperature. Iodomethane (1.4 mL) was added and the mixture stirred for 2 hrs. The reaction mixture was quenched with saturated aqueous $NH_4Cl$ (30 mL). EtOAc (100 mL) was added and the mixture phase separated. The organic layer was collected, washed with brine (50 mL) and then dried over $Mg_2SO_4$. After filtration and evaporation of the solvent the product (3.1 g) was collected. NMR analysis showed the product to have a structure consistent with 3,3-(di(4-methoxyphenyl)-6,11-dimethoxy-13-methyl-3H,13H indeno[2,1-f]naphtho[1,2-b]pyran. The structure was supported by NMR analysis.

Step 4

Product from Step 3 (3.1 g) was dissolved in dry diethyl ether (100 mL) in a reaction flask and the resulting solution cooled to −50° C. in a bath of dry ice in acetone. n-BuLi (2.5M in Hexanes, 2.5 mL) was slowly added. The mixture was stirred for 10 minutes in the cold bath and then 1 h at room temperature. The reaction mixture was poured into crushed dry ice (10 g). Water was added (30 mL) and the solution brought to neutral pH using diluted HCl. The mixture was then extracted with EtOAc (150 mL) and the organic phase collected. Evaporation of the solvent yielded the product 3,3-(di(4-methoxyphenyl)-6,11-dimethoxy-13-hydroxycarbonyl-13-methyl-3H,13H indeno[2,1-f]naphtho[1,2-b]pyran (3 g) which was used in the next step without further purification.

Step 5

The product of Step 4 (3 g) was dissolved in ethanol (150 mL) in a reaction flask and 2 drops of $H_2SO_4$ were added. The mixture was heated to reflux for 3 hrs and then cooled to room temperature. After evaporation of the solvent, the resulting residue was dissolved in DCM (100 mL) and washed with brine (50 mL). The organic layer was collected and the solvent evaporated to provide the product 3,3-(di(4-methoxyphenyl)-6,11-dimethoxy-13-ethoxycarbonyl-13-methyl-3H,13H indeno[2,1-f]naphtho[1,2-b]pyran (3.1 g). The product was used in the next step without further purification.

Step 6

The product of Step 5 (3.1 g) was dissolved in dTHF (90 mL) in a reaction flask and the resulting solution cooled to 0° C. in an ice bath. Lithium aluminum hydride (LAH) was added portion wise (3 portions of 70 mg each). The mixture was stirred for 10 minutes in the ice bath and then 2 hrs at room temperature. The reaction mixture was quenched with saturated aqueous $NH_4Cl$ (30 mL). EtOAc (150 mL) was added and the mixture phase separated. The organic layer was collected, washed with brine (50 mL) and then dried over $Mg_2SO_4$. After filtration and evaporation of the solvent the product (2.9 g) was collected. NMR analysis showed the product to have a structure consistent with 3,3-(di(4-methoxyphenyl)-6,11-dimethoxy-13-hydroxymethyl-13-methy indeno[2,1-f]naphtho[1,2-b]pyran.

CE-41

Step 1

The procedure described in Step 5 of Example 7 of U.S. Pat. No. 7,465,415B2 was followed except that product PA-16 was used in place of 1-(4-(2-hydroxyethoxy)phenyl)-1-(4-morpholinophenyl)prop-2-yn-1-ol to produce 3-(3-bromo-4-(methoxyphenyl)-3-(4-morpholinophenyl)-13,13-dimethyl-3H,13H indeno[2,1-f]naphtho[1,2-b]pyran. The structure was supported by NMR analysis.

Step 2

To a solution of product from Step 1 (0.7 g) in THF (40 mL) and water (30 mL) in a reaction flask, KF (0.9 g) and the vinylboronic pinacol ester (0.5 mL) were added while stirring at room temperature. The mixture was degassed for 10 min and then bis(triphenylphosphine)palladium(II) dichloride (0.14 g) was added. The mixture was refluxed for 12 hrs. The reaction was cooled to room temperature and EtOAc (100 mL) was added. The mixture phase separated. The resulting organic phase was collected and washed with brine. After evaporation of the solvent, the residue was collected and purified by column chromatography on silica gel eluting with hexanes/DCM (411, V/V). The fractions containing the product were collected to provide the product (0.4 g). NMR analysis showed the product to have a structure consistent with 3-(3-vinyl-4-(methoxyphenyl)-3-(4-morpholinophenyl)-13,13-dimethyl-3H,13H indeno[2,1-f]naphtho[1,2-b]pyran.

CE-42

The procedure of Step 5 of Example 7 of U.S. Pat. No. 7,465,415B2 was followed except that product N-22 was used instead of 4,7,7-dimethyl-5-hydroxy-7Hbenzo[C]fluorene and product PA-17 instead of 1-(4-(2-hydroxyethoxy)phenyl)-1-(4-morpholinophenyl)prop-2-yn-1-ol to produce 3-(4-(2-(hydroxymethyl)morpholino)phenyl)-3-(4-methoxyphenyl)-7-methoxy-11-phenyl-13,13-dimethyl-3H,13H indeno[2,1-f]naphtho[1,2-b]pyran. The structure was supported by NMR analysis.

CE-43

The procedure of Step 5 of Example 7 of U.S. Pat. No. 7,465,415B2 was followed except that product N-22 was used instead of 4,7,7-dimethyl-5-hydroxy-7Hbenzo[C]fluorene and product PA-13 instead of 1-(4-(2-hydroxyethoxy)phenyl)-1-(4-morpholinophenyl)prop-2-yn-1-ol to produce 3-(4 (4-(2-hydroxyethyl)piperazin-1-yl)phenyl)-3-(4-fluorophenyl)-7-methoxy-11-phenyl-13,13-dimethyl-3H,13H indeno[2,1-f]naphtho[1,2-b]pyran. The structure was supported by NMR analysis.

CE-44

The procedure of Step 5 of Example 7 of U.S. Pat. No. 7,465,415B2 was followed except that product N-22 was used instead of 4,7,7-dimethyl-5-hydroxy-7Hbenzo[C]fluorene and product PA-20 instead of 1-(4-(2-hydroxyethoxy)phenyl)-1-(4-morpholinophenyl)prop-2-yn-1-ol to produce 3-(4 (allyloxy)phenyl)-3-(4-morpholinophenyl)-7-methoxy-11-phenyl-13,13-dimethyl-3H,13H indeno[2,1-f]naphtho[1,2-b]pyran. The structure was supported by NMR analysis.

CE-45

Step 1

The procedure described in Step 5 of Example 7 of U.S. Pat. No. 7,465,415B2 was followed except that product PA-11 was used in place of 1-(4-(2-hydroxyethoxy)phenyl)-1-(4-morpholinophenyl)prop-2-yn-1-ol to produce 3-(4-fluorophenyl)-3-(4-(4-formylpiperazin-1-yl)phenyl)-13,13-dimethyl-3H,13H indeno[2,1-f]naphtho[1,2-b]pyran. The structure was supported by NMR analysis.

Step 2

The product from Step 1 (3.5 g) was dissolved in 1,4-dioxane (35 mL) in a reaction flask, and water (25 mL) was added. The mixture was refluxed until the material was dissolved and HCl (36%, 4 mL) was added. After 2 hrs of refluxing the mixture was cooled and poured into a 1 L beaker containing aqueous KOH (0.5M, 150 mL). EtOAc (300 mL) was added and the mixture phase separated. The resulting organic phase was washed with brine (100 mL) and after evaporation of the solvent yielded the product (3.2 g). NMR analysis showed the product to have a structure consistent with 3-(4-fluorophenyl)-3-(4-(piperazin-1-yl)phenyl)-13,13-dimethyl-3H,13H indeno[2,1-f]naphtho[1,2-b]pyran.

Step 3

The procedure used for the preparation of CE-29 was used except that the product from Step 2 was used instead of CE-28 to produce -(4-fluorophenyl)-3-(4-(4-(3-carboxypropanoyl) piperazin-1-yl)phenyl)-13,13-dimethyl-3H,13H indeno[2,1-f]naphtho[1,2-b]pyran. The structure was supported by NMR analysis.

CE-46

The procedure described in Step 5 of Example 7 of U.S. Pat. No. 7,465,415B2 was followed except that product PA-18 was used in place of 1-(4-(2-hydroxyethoxy)phenyl)-1-(4-morpholinophenyl)prop-2-yn-1-ol to produce 3-(4-fluorophenyl)-3-(4-(4-(hydroxymethyl)piperidin-1-yl)phenyl)-13,13-dimethyl-3H,13H indeno[2,1-f]naphtho[1,2-b]pyran. The structure was supported by NMR analysis.

CE-47

The procedure of Step 5 of Example 7 of U.S. Pat. No. 7,465,415B2 was followed except that product N-17 was used instead of 4,7,7-dimethyl-5-hydroxy-7Hbenzo[C]fluorene to produce 3-(4-(2-hydroxyethoxy)phenyl)-3-(4-morpholinophenyl)-6-methoxy-7-(piperidin1-yl)-11-phenyl-13,13-dimethyl-3H,13H indeno[2,1-f]naphtho[1,2-b]pyran. The structure was supported by NMR analysis.

CE-48

The procedure of Step 5 of Example 7 of U.S. Pat. No. 7,465,415B2 was followed except that product N-7 was used instead of 4,7,7-dimethyl-5-hydroxy-7Hbenzo[C]fluorene and product PA-14 instead of 1-(4-(2-hydroxyethoxy)phenyl)-1-(4-morpholinophenyl)prop-2-yn-1-ol to produce 3-(4-(2-(hydroxymethyl)morpholino)phenyl)-3-(4-fluorophenyl)-6,7-dimethoxy-11-(4-(trifluoromethyl)phenyl)-13,13-dimethyl-3H,13H indeno[2,1-f]naphtho[1,2-b]pyran. The structure was supported by NMR analysis.

CE-49

The procedure described in Step 5 of Example 7 of U.S. Pat. No. 7,465,415B2 was followed except that product PA-13 was used in place of 1-(4-(2-hydroxyethoxy)phenyl)-1-(4-morpholinophenyl)prop-2-yn-1-ol to produce 3-(4-(4-(2-hydroxyethyl)piperazin-1-yl)phenyl)-3-(4-fluorophenyl)-13,13-dimethyl-3H,13H indeno[2,1-f]naphtho[1,2-b]pyran. The structure was supported by NMR analysis.

CE-50

The procedure used in Step 1 of CE-5 was followed except that product N-23 was used in place of product N-6 to produce 3-(4-(2-hydroxyethoxy)phenyl)-3-(4-methoxyphenyl)-7-methoxy-11-phenyl-13,13-diethyl-3H,13H indeno[2,1-f]naphtho[1,2-b]pyran. The structure was supported by NMR analysis.

CE-51

The procedure used in Step 1 of CE-5 was followed except that product N-15 was used in place of product N-6 to produce 3-(4-(2-hydroxyethoxy)phenyl)-3-(4-methoxyphenyl)-6,7-dimethoxy-11-(4-cyanophenyl)-13,13-dimethyl-3H,13H indeno[2,1-f]naphtho[1,2-b]pyran. The structure was supported by NMR analysis.

CE-52

The procedure described in Step 5 of Example 7 of U.S. Pat. No. 7,465,415B2 was followed except that product PA-9 was used in place of 1-(4-(2-hydroxyethoxy)phenyl)-1-(4-morpholinophenyl)prop-2-yn-1-ol to produce 3-(4-fluorophenyl)-3-(4-(2-(hydroxymethyl)piperidin-1-yl)phenyl)-13,13-dimethyl-3H,13H indeno[2,1-f]naphtho[1,2-b]pyran. The structure was supported by NMR analysis.

CE-53

The procedure of Step 5 of Example 7 of U.S. Pat. No. 7,465,415B2 was followed except that product N-13 was used instead of 4,7,7-dimethyl-5-hydroxy-7Hbenzo[C]fluorene to produce 3-(4-(2-hydroxyethoxy)phenyl)-3-(4-morpholinophenyl)-6-methoxy-7-(piperidin1-yl)-11-(2-(trifluoromethyl)phenyl)-13,13-dimethyl-3H,13H indeno[2,1-f]naphtho[1,2-b]pyran. The structure was supported by NMR analysis.

CE-54

The procedure of Step 5 of Example 7 of U.S. Pat. No. 7,465,415B2 was followed except that product N-7 was used instead of 4,7,7-dimethyl-5-hydroxy-7Hbenzo[C]fluorene and product PA-3 instead of 1-(4-(2-hydroxyethoxy)phenyl)-1-(4-morpholinophenyl)prop-2-yn-1-ol to produce 3-(4-(2-(hydroxymethyl)piperidin-1-yl)phenyl)-3-(4-fluorophenyl)-6,7-dimethoxy-11-(4-(trifluoromethyl)phenyl)-13,13-dimethyl-3H,13H indeno[2,1-f]naphtho[1,2-b]pyran. The structure was supported by NMR analysis.

CE-55

The procedure used in Step 1 of CE-5 was followed except that product N-7 was used in place of product N-6 to produce 3-(4-(2-hydroxyethoxy)phenyl)-3-(4-methoxyphenyl)-6,7-dimethoxy-11-(4-(trifluoromethyl)phenyl)-13,13-dimethyl-3H,13H indeno[2,1-f]naphtho[1,2-b]pyran. The structure was supported by NMR analysis.

CE-56

The procedure of Step 5 of Example 7 of U.S. Pat. No. 7,465,415B2 was followed except that product N-12 was used instead of 4,7,7-dimethyl-5-hydroxy-7Hbenzo[C]fluorene and product PA-3 instead of 1-(4-(2-hydroxyethoxy)phenyl)-1-(4-morpholinophenyl)prop-2-yn-1-ol to produce 3-(4-(2-(hydroxymethyl)piperidin-1-yl)phenyl)-3-(4-fluorophenyl)-6,7-dimethoxy-11-(phenylethynyl)-13,13-dimethyl-3H,13H indeno[2,1-f]naphtho[1,2-b]pyran. The structure was supported by NMR analysis.

CE-57

The procedure described in Step 5 of Example 7 of U.S. Pat. No. 7,465,415B2 was followed except that product PA-12 was used in place of 1-(4-(2-hydroxyethoxy)phenyl)-1-(4-morpholinophenyl)prop-2-yn-1-ol to produce 3-phenyl-3-(4-bromophenyl)-13,13-dimethyl-3H,13H indeno[2,1-f]naphtho[1,2-b]pyran. The structure was supported by NMR analysis.

CE-58

The procedure used in Step 1 of CE-5 was followed except that product N-2 was used in place of product N-6 and product PA-6 instead of product PA-2 to produce 3-(4-(2-hydroxyethoxy)phenyl)-3-(4-fluorophenyl)-6,7-dimethoxy-1'-cyano-13,13-dimethyl-3H,13H indeno[2',3':3,4]naphtho[1,2-b]pyran. The structure was supported by NMR analysis.

CE-59

The procedure used in Step 1 of CE-5 was followed except that product N-2 was used in place of product N-6 to produce 3-(4-(2-hydroxyethoxy)phenyl)-3-(4-methoxyphenyl)-6,7-dimethoxy-11-cyano-13,13-dimethyl-3H,13H indeno[2',3':3,4]naphtho[1,2-b]pyran. The structure was supported by NMR analysis.

CE-60

The procedure used in Step 1 of CE-5 was followed except that product N-16 was used in place of product N-6 to produce 3-(4-(2-hydroxyethoxy)phenyl)-3-(4-methoxyphenyl)-6-methoxy-7-(diethylamino)-11-(trifluoromethyl)-13,13-dimethyl-3H,13H indeno[2',3':3,4]naphtho[1,2-b]pyran. The structure was supported by NMR analysis.

CE-61

Step 1

Procedure of Step 7 of Example 1 in U.S. Pat. No. 7,527,754B2 was used except that product PA-15 was used in place of 1-(fluorophenyl)-1-(4-piperidinophenyl)-2-propyn-1ol to produce 3-phenyl-3-(3-bromo-4-methoxyphenyl)-6,11-difluoro-13,13-dimethyl-3H,13H indeno[2,1-f]naphtho[1,2-b]pyran. The structure was supported by NMR analysis.

Step 2

The procedure described in Step 2 of CE-41 was followed except that product of Step 1 was used in place of 4-(4-(3-(3-bromo-4-methoxyphenyl)-13,13-dimethyl-3,13-dihydrobenzo[h]indeno[2,1-f]chromen-3-yl)phenyl)morpholine to produce 3-phenyl-3-(3-vinyl-4-methoxyphenyl)-6,11-difluoro-13,13-dimethyl-3H,13H indeno[2, f]naphtho[1,2-b]pyran. The structure was supported by NMR analysis.

CE-62 and CE-63

Product CE-61 (1.0 g) was dissolved in dTHF (50 mL) in a reaction flask, and the solution stirred under a nitrogen atmosphere. A solution of $BH_3$-THF complex (1M in THF, 0.9 mL) was added and the mixture was stirred for 2 hrs at room temperature. Ethanol (1.5 mL), 0.7 mL of NaOH (aqueous 6M, 0.7 mL) and $H_2O_2$ (aqueous 30%, 1.3 mL) were added and the mixture heated to reflux for 1 h. The mixture was diluted with EtOAc (100 mL) and brine (50 mL). The resulting organic layer was collected and purified by column chromatography on silica gel eluting with DCM/EtOAc (20/1, V/V). Two products were collected. NMR analysis showed that the less polar product (0.1 g) had a structure consistent with CE-63: 3-phenyl-3-(3-(1-hydroxyethyl)-4-methoxyphenyl)-6,11-difluoro-13,13-dimethyl-3H,13H indeno[2,1-f]naphtho[1,2-b]pyran and the more polar one had a structure consistent with CE-62: 3-phenyl-3-(3-(2-hydroxyethyl)-4-methoxyphenyl)-6,11-difluoro-13,13-dimethyl-3H,13H indeno[2,1-f]naphtho[1,2-b]pyran.

CE-64

Step 1

The procedure described in Step 7 of Example 10 in US 2006/0228557 was followed except that the product from Step 1 of N-20 was used in place of 2,3-dimethoxy-7-hydroxy-7-ethyl-11-phenyl-7H-benzo-[C]fluoren-5-01 to produce 3,3-(di(4-methoxyphenyl)-7-methoxy-11-phenyl-13-oxo-3H,13M indeno[2,1-f]naphtho[1,2-b]pyran. The structure was supported by NMR analysis.

Step 2

Steps 2 to 5 of CE-40 were followed except that 3,3-(di(4-methoxyphenyl)-7-methoxy-11-phenyl-13-oxo-3H,13H indeno[2,1-f]naphtho[1,2-b]pyran was used in place of 3,3-(di(4-methoxyphenyl)-6,11-dimethoxy-13-oxo-3H,13H indeno[2,1-f]naphtho[1,2-b]pyran to produce 3,3-di(4-methoxyphenyl)-7-methoxy-11-phenyl-13-hydroxymethyl-13-methyl-3H,13H indeno[2,1-t]naphtho[1,2-b]pyran. The structure was supported by NMR analysis.

CE-65

Into a 0.5 L reaction flask product N-4 (1.6 g) and product PA-7 (3.0 g) were dissolved in 1,2-dichloroethane (100 mL). PTSA (0.22 g) was added and the mixture was stirred at room temperature for 12 hrs. The solvent was evaporated and the resulting residue dissolved in MeOH (80 mL) and PTSA (0.5 g) was added. The mixture was heated to reflux for 12 hrs. After that the reaction was cooled to room temperature, the solvent evaporated, the residue dissolved in THF (100 mL), EtOAc (200 mL) was added and the solution washed with water (100 mL) and brine (100 mL). After evaporation of the solvents, the residue was purified by column chromatography eluting with methylene chloride/EtOAc (4/1, V/V) to provide the product (0.8 g) 3,3-bis(4-(2-hydroxyethoxy)phenyl)-13,13-dimethyl-3H,13H indeno[2,1-f]naphtho[1,2-b]pyran. The structure was supported by NMR analysis.

CE-66

Step 1

In a dried 0.5 L reaction flask under a nitrogen atmosphere, 4,4'-di-tert-butyl-2,2'dipyridyl (0.124 g) and (1,5-cyclooctadiene) (methoxy)iridinium(I) dimer (0.15 g) were added. Hexanes (60 mL), dimethyl isophthalate (3 g) and pinacolborane (2.5 mL) were charged. The mixture was stirred at room temperature under a nitrogen atmosphere for 12 hrs. Water was added (20 mL) and the mixture was extracted with EtOAc (200 mL). The organic phase was collected, washed with brine (80 mL) and dried over $Mg_2SO_4$. The residue was collected and purified by column chromatography on silica gel eluting with hexanes/DCM (1/2, V/V). The fractions containing the product were collected to provide the product (1.6 g). MS analysis supported the molecular weight of dimethyl 5-(4,4,5,5-tetramethyl-1,3,2-dioxaborolan-2-yl)isophthalate.

Step 2

The procedure of Step 2 of Example 12 in US 2006/0228557A1 was used except that product from Step 1 was used instead of 4-phenylboronic acid to produce 3,3-(di(4-methoxyphenyl)-6,7-dimethoxy-11-(3,5-bis(methoxycarbonyl)phenyl)-13,13-dimethyl-3H,13H indeno[2',3':3,4]naphtho[1,2-b]pyran. The structure was supported by NMR analysis.

Step 3

The product of Step 2 (0.3 g) was dissolved in dTHF (70 mL) in a reaction flask, and the mixture cooled to 0° C. with an ice bath. Vitride (65% solution on toluene, 2.5 mL) was slowly added. The ice bath was removed and the mixture stirred at room temperature for 12 hrs. Water (6 mL) and aqueous KOH (4M, 1 mL) were added and the mixture extracted with EtOAc (150 mL). The resulting organic phase was collected, washed with brine (50 mL) and then the solvent evaporated to provide the product (0.3 g). MS and NMR analysis supported the product to be 3,3-di(4-methoxyphenyl)-6,7-dimethoxy-11-(3,5-bis(hydroxymethyl)phenyl)-13,13-dimethyl-3H,13H indeno[2',3':3,4]naphtho[1,2-b]pyran.

CE-67

The procedure used in Step 1 of CE-5 was followed except that product N-9 was used in place of product N-6 and product PA-19 instead of product PA-2 to produce 3,3-di(4-(allyloxy)phenyl)-6-methoxy-7-(3-(hydroxymethyl)piperidin-1-yl)-11-hexylcarbamoyl -13,13-dimethyl-3H,13H indeno[2',3':3,4]naphtho[1,2-b]pyran. The structure was supported by NMR analysis

CE-68

The procedure described in CE-65 was followed except that N-5 was used in place of N-4 to produce 3,3-bis(4-(2-hydroxyethoxy)phenyl)-6,11-difluoro-13,13-dimethyl-3I-1,3H indeno[2,1-f]naphtho[1,2-b]pyran. The structure was supported by NMR analysis.

CE-69

The procedure used for the preparation of CE-29 was used except that the product CE-2 was used instead of CE-28 to produce 3,3-(di(4-methoxyphenyl)-6,11,13-trimethyl-13-(2-(2-(2-((3-carboxypropanoyl)oxy)ethoxy)ethoxy)ethoxy)-3H,13H indeno[2,1-f]naphtho[1,2-b]pyran. The structure was supported by NMR analysis.

CE-70

Step 1

In a dried 0.5 L reaction flask under a nitrogen atmosphere, product CE-69 (2.1 g) was dissolved in dMeCN (50 mL) and then N-Hydroxysuccinimide (NHS, 0.38 g) was added. The solution was cooled to 0° C. in an ice bath and then N,N'-dicyclohexylcarbodiimide (DCC, 0.68 g) dissolved in dMeCN (10 mL) was slowly added. The reaction mixture was stirred for 1 h at 0° C. and the ice bath removed. After 12 hrs the reaction mixture was filtered and the solid discarded. The liquid phase was concentrated and purified by column chromatography on silica gel eluting with DCM/EtOAc (1/1, V/V) to collect the product (3 g) NMR supported the product to be 3,3-(di(4-methoxyphenyl)-6,11,13-trimethyl-13-(2-(2-(2-((4-((2,5-dioxopyrrolidin-1-yl)oxy)-4-oxobutanoyl)oxy)ethoxy)ethoxy)ethoxy)-3H,13H indeno[2,1-f]naphtho[1,2-b]pyran.

Step 2

The product of Step 1 (3 g) was dissolved in pyridine (10 mL) in a reaction flask and 2,2'-iminodiethanol (0.9 g) was added. The mixture was stirred at room temperature for 2 days and the solvent was evaporated and MeCN (30 mL) was added. After filtration the solid was discarded, the filtrate collected and the solvent evaporated. The resulting product was dissolved in DCM (100 mL) washed with water (100 mL) and purified by column chromatography on silica gel eluting with DCM/MeOH (4/1, V/V) to collect the product (2.6 g). NMR analysis showed the product to have a structure consistent with 3,3-(di(4-methoxyphenyl)-6,11,13-trimethyl-13-(16-hydroxy-14-(2-hydroxyethyl)-10,13-dioxo-3,6,9-trioxa-14-azahexadecyl)oxy)-3H,13H indeno[2,1-f]naphtho[1,2-b]pyran.

CE-71

The procedure used in Step 1 of CE-5 was followed except that product N-14 was used in place of product N-6 to produce 3-(4-(2-hydroxyethoxy)phenyl)-3-(4-methoxyphenyl)-6-methoxy-7-(3-(hydroxymethyl)piperidin-1-yl)-13,13-dimethyl-3H,13H indeno[2',3':3,4]naphtho[1,2-b]pyran. The structure was supported by NMR analysis.

CE-72

The procedure used for the preparation of CE-29 was used except that the product CE-5 was used instead of CE-28 to produce 3-((2-((3-carboxypropanoyl)oxy)ethoxy)phenyl)-3-(4-methoxyphenyl)-6,11,13-trimethyl-13-(2-(2-(2-((3-carboxypropanoyl)oxy)ethoxy)ethoxy)ethoxy)-3H,13H indeno[2,1-f]naphtho[1,2-b]pyran. The structure was supported by NMR analysis.

CE-73

The procedure described in CE-65 was followed except that N-10 was used in place of N-4 to produce 3,3-bis(4-(2-hydroxyethoxy)phenyl)-6-methoxy-7-(piperidin1-yl)-13,13-dimethyl-3H,13H indeno[2,1-f]naphtho[1,2-b]pyran. The structure was supported by NMR analysis.

CE-74

Step 1

The procedure described in Step 7 of Example 10 in US 2006/0228557 was followed except that the product of Step 5 of Example 4 in U.S. Pat. No. 5,645,767 was used in place of 2,3-dimethoxy-7-hydroxy-7-ethyl-11-phenyl-7H-benzo-[C]fluoren-5-ol to produce 3,3-(di(4-methoxyphenyl)-6,11-dimethyl-13-oxo-3H,13H indeno[2,1-f]naphtho[1,2-b]pyran. The structure was supported by NMR analysis.

Step 2

Steps 2 to 5 of CE-40 were followed except that 3,3-(di(4-methoxyphenyl)-6,11-dimethyl-13-oxo-3H,13H indeno[2,1-f]naphtho[1,2-b]pyran was used in place of 3,3-(di(4-methoxyphenyl)-6,11-dimethoxy-13-oxo-3H,13H indeno[2,1-f]naphtho[1,2-b]pyran to produce 3,3-(di(4-methoxyphenyl)-6,11-dimethyl-13-hydroxymethyl-13-methyl-3H,13H indeno[2,1-f]naphtho[1,2-b]pyran. The structure was supported by NMR analysis.

CE-75

The procedure described in Comparative Example 4 in US 2006/0228557 was followed to produce 3,3-di(4-methoxyphenyl)-6,7-dimethoxy-13-13-dimethyl-3H,13H indeno[2',3':3,4]naphtho[1,2-b]pyran. The structure was supported by NMR analysis.

CE-76

The procedure of Step 5 of Example 7 of U.S. Pat. No. 7,465,415B2 was followed except that 1,1-diphenyl-2-propyn-1-ol was used in place of 1-(4-(2-hydroxyethoxy)phenyl)-1-(4-morpholinophenyl)prop-2-yn-1-ol to produce 3,3-diphenyl-13,13-dimethyl-3H,13H indeno[2,1-f]naphtho[1,2-b]pyran. The structure was supported by NMR analysis.

CE-77

The procedure described in CE-62 was followed except that product CE41 was used in place of CE61 to collect only the major component. NMR analysis supported the product to be 3-(4-morpholinophenyl)-3-(3-(2-hydroxyethyl)-4-methoxyphenyl)-13,13-dimethyl-3H,13H indeno[2,1-f]naphtho[1,2-b]pyran.

CE-78

The procedure of Step 5 of Example 7 of U.S. Pat. No. 7,465,415B2 was followed except that product N-22 was used instead of 4,7,7-dimethyl-5-hydroxy-7Hbenzo[C]fluorene and product PA-23 instead of 1-(4-(2-hydroxyethoxy)phenyl)-1-(4-morpholinophenyl)prop-2-yn-1-ol to produce 3-(4-butoxyphenyl)-3-(4-methoxyphenyl)-7-methox-11-phenyl-13,13-dimethyl-3H,13 indeno[2,1-f]naphtho[1,2-b]pyran. The structure was supported by NMR analysis.

Part 4—Preparation of Examples (E) 1-87

E-1

In a 300 mL dried single neck flask CE-2 (1.0 g) was dissolved in DCM (50 mL) and the resulting solution cooled to 0° C. under a nitrogen atmosphere. TEA (0.3 mL) and 4-DMAP (18 mg) were successively added. A solution of [tris(trimethylsiloxy)silylethyl]dimethyl-chlorosilane (0.8 mL) in DCM (10 mL) was added drop wise. The ice bath was removed and after 12 h aqueous HCl (5%, 30 mL) was added. The mixture phase separated and the recovered organic layer was washed with water (100 mL). After evaporation of the solvent, the resulting residue was purified by plug column chromatography on silica gel eluting with hexanes/DCM (2/1, V/V) and then with hexanes/DCM (1/10, V/V). The fractions containing the product were collected to provide the product (1.1 g). NMR analysis showed the product to have a structure consistent with 3,3-(di(4-methoxyphenyl)-6,11,13-trimethyl-13-((2,2,7,7-tetramethyl-4,4-bis((trimethylsilyl)oxy)-3,8,11,14-tetraoxa-2,4,7-trisilahexadecan-16-yl)oxy)-3H,13H indeno[2,1-f]naphtho[1,2-b]pyran.

E-2

The procedure described in Step 1 to 2 for the preparation of CE-70 was followed except that 3-aminopropylmethylbis(trimethylsiloxy)-silane was used in place of 2,2'-iminodiethanol to produce 3,3-(di(4-methoxyphenyl)-6,11,13-trimethyl-13-((2,2,4-trimethyl-9,12-dioxo-4-((trimethylsilyl)oxy)-3,13,16,19-tetraoxa-8-aza-2,4-disilahenicosan-21-yl)oxy)-3,8,11,14-tetraoxa-2,4,7-trisilahexadecan-16-yl)oxy)-3H,13H indeno[2,1-f]naphtho[1,2-b]pyran. The structure was supported by NMR analysis.

E-3

In a 300 mL dried single neck flask CE-2 (1.0 g) was dissolved in DCM (50 mL) and the resulting solution cooled to 0° C. under a nitrogen atmosphere. TEA (0.46 mL) and 4-DMAP (18 mg) were successively added. A solution of tris(trimethylsiloxy)dimethyl-chlorosilane (1.1 mL) in DCM (10 mL) was added drop wise. The ice bath was removed and after 12 h aqueous HCl (5%, 30 mL) was added. The mixture phase separated and the recovered organic layer was washed with water (100 mL). After evaporation of the solvent, the resulting residue was purified by plug column chromatography on silica gel eluting with hexanes/DCM (2/1, V/V) and then with hexanes/DCM (1/10, V/V). The fractions containing the product were collected to provide the product (1.3 g). NMR analysis showed the product to have a structure consistent with 3,3-(di(4-methoxyphenyl)-6,11,13-trimethyl-13-((2,2-dimethyl-4,4-bis((trimethylsilyl)oxy)-3,5,8,11-tetraoxa-2,4-disilatridecan-13-yl)oxy)-3H,13H indeno[2,1-f]naphtho[1,2-b]pyran.

E-4

The procedure described for E-1 was followed except that [bis(nonafluorohexyldimethylsiloxy)methyl]-silylethyldimethylchlorosilane was used in place of [tris(trimethylsiloxy)silylethyl]dimethyl-chlorosilane to produce 3,3-(di(4-methoxyphenyl)-6,11,13-trimethyl-13-((13-((dimethyl(3,3,4,4,5,5,6,6,6-nonafluorohexyl)silyl)oxy)-18,18,19,19,20,20,21,21,21-nonafluoro-10,10,13,15,15-pentamethyl-3,6,9,14-tetraoxa-10,13,15-trisilahenicosyl)oxy)-3H,13H indeno[2,1-f]naphtho[1,2-b]pyran. The structure was supported by NMR analysis.

E-5

In a dried flask under a nitrogen atmosphere, CE-69 (1.2 g) was dissolved in DCM (50 mL) then 3-[hydroxy(polyethyleneoxy)propyl]-heptamethyltrisiloxane (0.8 mL) and 4-DMAP (17 mg) were added. The solution was cooled to 0° C. in an ice bath and DCC (0.34 g) dissolved in DCM (10 mL) was slowly added to the reaction mixture. The reaction mixture was kept for 90 min at 0° C. and then the ice bath was removed. After 10 hrs the solvent was evaporated and the resulting residue purified by column chromatography on silica gel eluting with DCM/EtOAc (2/1, V/V) to provide the product (0.4 g). NMR and MS analysis supported the product to contain mainly 3,3-(di(4-methoxyphenyl)-6,11,13-trimethyl-13-((2,2,4-trimethyl-21,24-dioxo-4-((trimethylsilyl)oxy)-3,8,11,14,17,20,25,28,31-nonaoxa-2,4-disilatritricontan-33-yl)oxy)-3,8,11,14-tetraoxa-2,4,7-trisilahexadecan-16-yl)oxy)-3H,13H indeno[2,1-f]naphtho[1,2-b]pyran.

E-6

The procedure described for E-1 was followed except that CE-3 was used in place of CE-2 to produce 3,3-(di(4-methoxyphenyl)-6,11,13-trimethyl-13-(2-(((2-(1,1,1,5,5,5-hexamethyl-3-(((trimethylsilyl)oxy)trisiloxan-3-yl)ethyl)dimethylsilyl)oxy)ethoxy)-3H,13H indeno[2,1-f]naphtho[1,2-b]pyran. The structure was supported by NMR analysis.

E-7

The procedure described for E-2 was used except that CE-3 was used instead of CE-2 to produce 3,3-(di(4-methoxyphenyl)-6,11,13-trimethyl-13-(2-((4-((3-(1,1,1,3,5,5,5-heptamethyltrisiloxan-3-yl) propyl)amino)-4-oxobutanoyl)oxy) ethoxy)-3,8,11,14-tetraoxa-2,4,7-trisilahexadecan-16-yl) oxy)-3H,13H indeno[2,1-f]naphtho[1,2-b]pyran. The structure was supported by NMR analysis.

E-8

The procedure described for E-1 was followed except that CE-1 was used in place of CE-2 to produce 3,3-(di(4-methoxyphenyl)-6,11,13-trimethyl-13-(((2-(1,1,1,5,5,5-hexamethyl-3-((trimethylsilyl)oxy)trisiloxan-3-yl)ethyl)dimethylsilyl)oxy)-3H,13H indeno[2,1-f]naphtho[1,2-b]pyran. The structure was supported by NMR analysis.

E-9

In a dried flask, CE-4 (1.4 g) was dissolved in toluene (15 mL) and bis(trimethylsiloxy)methylsilane (0.7 mL) was added. Platinum (0)-1,3-divinyl-1,1,3,3-tetramethyldisiloxane complex (solution in xylene, Pt ~2%, 4 drops) were added. The reaction mixture was stirred at room temperature. After 24 hrs the solvent was evaporated and the resulting residue purified by column chromatography on silica gel eluting with DCM/Hexanes (3/2, V/V) to provide the product (1 g). NMR analysis showed the product to have a structure consistent with 3,3-(di(4-methoxyphenyl)-6,1,13-trimethyl-13-(3-(1,1,1,3,5,5,5-heptamethyltrisiloxan-3-yl)propoxy)-3H,13H indeno[2,1-f]naphtho[1,2-b]pyran.

E-10

The procedure described for E-3 was followed except that CE-8 was used in place of CE-2 to produce 3-(4-morpholinophenyl)-3-(4-methoxyphenyl)-6,11-dimethyl-13-(11-((1,1,1,5,5,5-hexamethyl-3-((trimethylsilyl)oxy)trisiloxan-3-yl)oxy)undecyl)-13-(methoxycarbonyl)-3H,13H indeno[2,1-f]naphtho[1,2-b]pyran. The structure was supported by NMR analysis.

E-11

The procedure described in E-9 was followed except that CE-7 was used in place of CE-4. NMR analysis showed the product to be consistent with the structure of 3-(4-(2-hydroxyethoxy)phenyl)-3-(4-methoxyphenyl)-6,11,13-trimethyl-13-(3-(1,1,1,3,5,5,5-heptamethyltrisiloxan-3-yl)propoxy)-3H,13H indeno[2,1-f]naphtho[1,2-b]pyran with 5-6 units of caprolactone monomers polymerized at the hydroxyl functionality.

E-12

Step 1

The procedure described for E-1 was followed except that trivinylchlorosilane was used in place of [tris(trimethylsiloxy)silylethyl]dimethyl-chlorosilane to produce 3,3-(di(4-methoxyphenyl)-6,11,13-trimethyl-13-((3,3-divinyl-4,7,10-trioxa-3-siladodec-1-en-12-yl)oxy)-3'-1,13H indeno[2,1-f]naphtho[1,2-b]pyran. The structure was supported by NMR analysis.

Step 2

The procedure used in E-9 was followed except that the product of Step 1 was used instead of CE-4 and the stoichiometry adjusted to produce 3,3-(di(4-methoxyphenyl)-6,11,13-trimethyl-13-(7,7-bis(2-(1,1,1,3,5,5,5-heptamethyltrisiloxan-3-yl)ethyl)-2,2,4-trimethyl-4-((trimethylsilyl)oxy)-3,8,11,14-tetraoxa-2,4,7-trisilahexadecan-16-yl)oxy)-3H,13H indeno[2,1-f]naphtho[1,2-b]pyran. The structure was supported by NMR analysis.

E-13

The procedure described for E-3 was followed except that CE-9 was used in place of CE-2 to produce 3,3-(di(4-methoxyphenyl)-6,11-dimethoxy-13-butyl-13-(2-((1,1,1,5,5,5-hexamethyl-3-((trimethylsilyl)oxy)trisiloxan-3-yl)oxy) ethoxy)-3H,13H indeno[2,1-f]naphtho[1,2-b]pyran. The structure was supported by NMR analysis.

E-14

The procedure described for E-3 was followed except that CE-40 was used in place of CE-2 to produce 3,3-(di(4-methoxyphenyl)-6,11-dimethoxy-13-(((1,1,1,5,5,5-hexamethyl-3-((trimethylsilyl)oxy)trisiloxan-3-yl)oxy)methyl)-13-methyl-31-1,3H indeno[2,1-f]naphtho[1,2-b]pyran. The structure was supported by NMR analysis.

E-15

The procedure described for E-3 was followed except that CE-74 was used in place of CE-2 to produce 3,3-(di(4-methoxyphenyl)-6,11-dimethyl-13-(((1,1,1,5,5,5-hexamethyl-3-((trimethylsilyl)oxy)trisiloxan-3-yl)oxy)methyl)-13-methyl-3H,13H indeno[2,1-f]naphtho[1,2-b]pyran. The structure was supported by NMR analysis.

E-16

The procedure described for E-3 was followed except that CE-64 was used in place of CE-2 to produce 3,3-di(4-methoxyphenyl)-7-methoxy-11-phenyl-13-(((1,1,1,5,5,5-hexamethyl-3-((trimethylsilyl)oxy)trisiloxan-3-yl)oxy)methyl)-13-methyl-31-1,3H indeno[2,1-f]naphtho[1,2-b]pyran. The structure was supported by NMR analysis.

E-17

The preparation described for E-2 was used except that CE-6 was used instead of CE-2 to produce 3,3-di(4-methoxyphenyl)-6,7-dimethoxy-11-((3-(1,1,1,3,5,5,5-heptamethyltrisiloxan-3-yl)propyl)carbamoyl)-13,13-dimethyl-3H,13H indeno[2',3':3,4]naphtho[1,2-b]pyran. The structure was supported by NMR analysis.

E-18

The procedure described for E-3 was followed except that CE-22 was used in place of CE-2 to produce 3,3-(di(4-methoxyphenyl)-6,7-dimethoxy-11-(((1,1,1,5,5,5-hexamethyl-3-((trimethylsilyl)oxy)trisiloxan-3-yl)oxy)methyl)-13,13-dimethyl-3H,13H indeno[2',3':3,4]naphtho[1,2-b]pyran. The structure was supported by NMR analysis.

E-19

The procedure described for E-3 was followed except that CE-23 was used in place of CE-2 to produce 3,3-(di(4-methoxyphenyl)-6,7-dimethoxy-11-(4-(((1,1,1,5,5,5-hexamethyl-3-((trimethylsilyl)oxy)trisiloxan-3-yl)oxy)methyl)

phenyl)-13,13-dimethyl-3H,13H-indeno[2',3':3,4]naphtho[1,2-b]pyran. The structure was supported by NMR analysis.

E-20

The procedure described for E-1 was followed except that CE-24 was used in place of CE-2 to produce 3,3-(di(4-methoxyphenyl)-6-methoxy-7-(3-(((((2-(1,1,1,5,5,5-hexamethyl-3-((trimethylsilyl)oxy)trisiloxan-3-yl)ethyl)dimethylsilyl)oxy)methyl)piperidin-1-yl)-13,13-dimethyl-3H,13H indeno[2',3':3,4]naphtho[1,2-b]pyran. The structure was supported by NMR analysis.

E-21

In a dried 0.3 L reaction flask, CE-25 (1.9 g) was dissolved in dTHF (20 mL). The mix was cooled at −75° C. using a dry ice-acetone bath and stirred under dry nitrogen. n-BuLi (2M in cyclohexane, 1.9 mL) was added and after 1 min tris(trimethylsiloxy)dimethyl-chlorosilane (1.6 mL) was added. The reaction mixture was left to react in the cold bath for 20 min and then at room temperature for 12 hrs. Water was added (20 mL) and the mixture extracted with EtOAc (50 mL). The recovered organic phase was washed with brine (30 mL) and the solvent evaporated. The resulting residue was purified by column chromatography on silica gel eluting with hexanes/DCM (4/1,V/V) to provide the product (0.7 g). NMR analysis showed the product to have a structure consistent with 3,3-di(4-methoxyphenyl)-6,7-dimethoxy-11-(1,1,1,5,5,5-hexamethyl-3-((trimethylsilyl)oxy)trisiloxan-3-yl)-13,13-dimethyl-3H,13H indeno[2',3':3,4]naphtho[1,2-b]pyran.

E-22

The procedure of E-21 was followed except that [tris(trimethylsiloxy)silylethyl]dimethyl-chlorosilane was used in place of tris(trimethylsiloxy)dimethyl-chlorosilane to produce 3,3-di(4-methoxyphenyl)-6,7-dimethoxy-11-((2-(1,1,1,5,5,5-hexamethyl-3-((trimethylsilyl)oxy)trisiloxan-3-yl)ethyl)dimethylsilyl)-13,13-dimethyl-3H,13H indeno[2',3':3,4]naphtho[1,2-b]pyran. The structure was supported by NMR analysis.

E-23

The procedure described for E-3 was followed except that CE-26 was used in place of CE-2 to produce 3-(4-fluorophenyl)-3-(4-(3-(((1,1,1,5,5,5-hexamethyl-3-((trimethylsilyl)oxy)trisiloxan-3-yl)oxy)methyl)piperidin-1-yl)phenyl)-7-methoxy-11-phenyl-13,13-dimethyl-3H,13H indeno[2,1-f]naphtho[1,2-b]pyran. The structure was supported by NMR analysis.

E-24

The procedure described for E-3 was followed except that CE-13 was used in place of CE-2 to produce 3-(4-(2-(((1,1,1,5,5,5-hexamethyl-3-((trimethylsilyl)oxy)trisiloxan-3-yl)oxy)ethoxy)phenyl)-3-(4-morpholinophenyl)-7-methoxy-11-phenyl-13,13-dimethyl-3H,13H indeno[2,1-f]naphtho[1,2-b]pyran. The structure was supported by NMR analysis.

E-25

The procedure described for E-3 was followed except that CE-27 was used in place of CE-2 to produce 3-(4-(2-(((1,1,1,5,5,5-hexamethyl-3-((trimethylsilyl)oxy)trisiloxan-3-yl)oxy)ethoxy)phenyl)-3-(4-methoxyphenyl)-7-methoxy-11-phenyl-13,13-dimethyl-3H,13H indeno[2,1-f]naphtho[1,2-b]pyran. The structure was supported by NMR analysis.

E-26

The preparation described for E-2 was used except that CE-29 was used instead of CE-2 to produce 3-(4-(2-((4-((3-(1,1,1,3,5,5,5-heptamethyltrisiloxan-3-yl)propyl)amino)-4-oxobutanoyl)oxy)ethoxy)phenyl)-3-(4-methoxyphenyl)-6,11,13-trimethyl-13-methoxy-3H,13H indeno[2,1-f]naphtho[1,2-b]pyran. The structure was supported by NMR analysis.

E-27

The procedure described for E-1 was followed except that CE-30 was used in place of CE-2 to produce 3-(4-(2-(((2-(1,1,1,5,5,5-hexamethyl-3-((trimethylsilyl)oxy)trisiloxan-3-yl)ethyl)dimethylsilyl)oxy)ethoxy)phenyl)-3-(4-methoxyphenyl)-6,11-difluoro-13,13-dimethyl-3H,13H indeno[2,1-f]naphtho[1,2-b]pyran. The structure was supported by NMR analysis.

E-28

The preparation described for E-2 was used except that CE-31 was used instead of CE-2 to produce 3-(4-(2-((4-((3-(1,1,1,3,5,5,5-heptamethyltrisiloxan-3-yl)propyl)amino)-4-oxobutanoyl)oxy)ethoxy)phenyl)-3-(4-methoxyphenyl)-6,11-difluoro-13,13-dimethyl-3H,13H indeno[2,1-f]naphtho[1,2-b]pyran. The structure was supported by NMR analysis.

E-29

The procedure described for E-3 was followed except that CE-30 was used in place of CE-2 to produce 3-(4-(2-(((1,1,1,5,5,5-hexamethyl-3-((trimethylsilyl)oxy)trisiloxan-3-yl)oxy)ethoxy)phenyl)-3-(4-methoxyphenyl)-6,11-difluoro-13,13-dimethyl-3H,13H indeno[2,1-f]naphtho[1,2-b]pyran. The structure was supported by NMR analysis.

E-30

The procedure described for E-3 was followed except that CE-32 was used in place of CE-2 to produce 3-phenyl-3-(4-(3-(((1,1,1,5,5,5-hexamethyl-3-((trimethylsilyl)oxy)trisiloxan-3-yl)oxy)methyl)piperidin-1-yl)phenyl)-6,11-difluoro-13,13-dimethyl-3H,13H indeno[2,1-f]naphtho[1,2-b]pyran. The structure was supported by NMR analysis.

E-31

The procedure described for E-3 was followed except that CE-33 was used in place of CE-2 to produce 3-(4-(2-(((1,1,1,5,5,5-hexamethyl-3-((trimethylsilyl)oxy)trisiloxan-3-yl)oxy)ethoxy)phenyl)-3-(4-methoxyphenyl)-13,13-dimethyl-3H,13H indeno[2,1-f]naphtho[1,2-b]pyran. The structure was supported by NMR analysis.

E-32

The procedure described for E-3 was followed except that CE-34 was used in place of CE-2 to produce 3-(4-(2-(((1,1,1,5,5,5-hexamethyl-3-((trimethylsilyl)oxy)trisiloxan-3-yl)oxy)ethoxy)phenyl)-3-(4-morpholinophenyl)-6-methoxy-7- morpholino-11-phenyl-13,13-dimethyl-3H,13H indeno[2,1-f]naphtho[1,2-b]pyran. The structure was supported by NMR analysis.

E-33

The procedure described for E-3 was followed except that CE-35 was used in place of CE-2 to produce 3-(4-(2-((1,1,1,5,5,5-hexamethyl-3-((trimethylsilyl)oxy)trisiloxan-3-yl)oxy)ethoxy)phenyl)-3-(4-methoxyphenyl)-6,7-dimethoxhy-11-(trifluoromethyl)-13,13-dimethyl-3H,13H indeno[2,1-f]naphtho[1,2-b]pyran. The structure was supported by NMR analysis.

E-34

The procedure described for E-3 was followed except that CE-36 was used in place of CE-2 to produce 3-(4-fluorophenyl)-3-(4-(3-(((1,1,1,5,5,5-hexamethyl-3-((trimethylsilyl)oxy)trisiloxan-3-yl)oxy)methyl)piperidin-1-yl)phenyl)-13,13-dimethyl-3H,13H indeno[2,4]naphtho[1,2-b]pyran. The structure was supported by NMR analysis.

E-35

The procedure described for E-3 was followed except that CE-10 was used in place of CE-2 to produce 3-(4-(2-((1,1,1,5,5,5-hexamethyl-3-((trimethylsilyl)oxy)trisiloxan-3-yl)oxy)ethoxy)phenyl)-3-phenyl-6,11-difluoro-13,13-dimethyl-3H,13H indeno[2,1-f]naphtho[1,2-b]pyran. The structure was supported by NMR analysis.

E-36

The procedure described for E-3 was followed except that CE-11 was used in place of CE-2 to produce 3-(4-(2-((1,1,1,5,5,5-hexamethyl-3-((trimethylsilyl)oxy)trisiloxan-3-yl)oxy)ethoxy)phenyl)-3-(4-methoxyphenyl) -6,7-dimethoxy-11-hexylcarbamoyl-13,13-dimethyl-3H,13H indeno[2,1-f]naphtho[1,2-b]pyran. The structure was supported by NMR analysis.

E-37

The procedure used in E-9 was followed except that CE-15 was used instead of CE-4 to produce 3-(4-(2-(3-(1,1,1,3,5,5,5-heptamethyltrisiloxan-3-yl)propoxy)ethoxy)phenyl)-3-(4-methoxyphenyl)-6,7-dimethoxy-11-(hydroxymethyl)-13,13-dimethyl-3H,13H indeno[2',3':3,4]naphtho[1,2-b]pyran. The structure was supported by NMR analysis.

E-38

The preparation described for E-2 was used except that CE-37 was used instead of CE-2 to produce 3-(4-(2-((4-((3-(1,1,1,3,5,5,5-heptamethyltrisiloxan-3-yl)propyl)amino)-4-oxobutanoyl)oxy)ethoxy)phenyl)-3-(4-morpholinophenyl)-7-methoxy-11-phenyl-13,13-dimethyl-3H,13H indeno[2,1-f]naphtho[1,2-b]pyran. The structure was supported by NMR analysis.

E-39

The procedure described for the preparation of E-31 was followed except that Tri-t-terbutoxychlorosilane was used in place of tris(trimethylsiloxy)dimethyl-chlorosilane to produce 3-(4-(2-((tri-tert-butoxysilyl)oxy)ethoxy)phenyl)-3-(4-methoxyphenyl)-13,13-dimethyl-3H,13H indeno[2,1-f]naphtho[1,2-b]pyran. The structure was supported by NMR analysis.

E-40

The procedure described for E-3 was followed except that CE-12 was used in place of CE-2 to produce 3-(4-(2-((1,1,1,5,5,5-hexamethyl-3-((trimethylsilyl)oxy)trisiloxan-3-yl)oxy)ethoxy)phenyl)-3-(4-morpholinophenyl)-13,13-dimethyl-3H,13H indeno[2,1-f]naphtho[1,2-b]pyran. The structure was supported by NMR analysis.

E-41

The procedure described for E-3 was followed except that CE-16 was used in place of CE-2 to produce 3-(4-(2-((1,1,1,5,5,5-hexamethyl-3-((trimethylsilyl)oxy)trisiloxan-3-yl)oxy)ethoxy)phenyl)-3-(4-methoxyphenyl)-6-methoxy-7-(piperidin1-yl)-13,13-dimethyl-3H,13H indeno[2,1-f]naphtho[1,2-b]pyran. The structure was supported by NMR analysis.

E-42

The procedure described for E-3 was followed except that CE-17 was used in place of CE-2 to produce 3-(4-(2-((1,1,1,5,5,5-hexamethyl-3-trimethylsilyl)oxy)trisiloxan-3-1 oxy)ethoxy)phenyl)-3-(4-methoxyphenyl)-11-(4-methoxyphenyl)-13,13-dimethyl-3H,13H indeno[2,1-f]naphtho[1,2-b]pyran. The structure was supported by NMR analysis.

E-43

The procedure described for E-3 was followed except that CE-14 was used in place of CE-2 to produce 3-(4-(2-((1,1,1,5,5,5-hexamethyl-3-((trimethylsilyl)oxy)trisiloxan-3-yl)oxy)ethoxy)phenyl)-3-(4-methoxyphenyl)-11-(4-(dimethylamino)phenyl)-13,13-dimethyl-3H,13H indeno[2,1-f]naphtho[1,2-b]pyran. The structure was supported by NMR analysis.

E-44

The procedure described for E-3 was followed except that CE-18 was used in place of CE-2 to produce 3-(4-(2-((1,1,1,5,5,5-hexamethyl-3-((trimethylsilyl)oxy)trisiloxan-3-yl)oxy)ethoxy)phenyl)-3-(4-fluorophenyl)-11-(4-(dimethylamino)phenyl)-13,13-dimethyl-3H,13H indeno[2,1-f]naphtho[1,2-b]pyran. The structure was supported by NMR analysis.

E-45

The procedure described for E-3 was followed except that CE-19 was used in place of CE-2 to produce 3-(4-(2-((1,1,1,5,5,5-hexamethyl-3-((trimethylsilyl)oxy)trisiloxan-3-yl)oxy)ethoxy)phenyl)-3-(4-methoxyphenyl)-11-(2-methoxyphenyl)-13,13-dimethyl-3H,13H indeno[2,1-f]naphtho[1,2-b]pyran. The structure was supported by NMR analysis.

E-46

The procedure described for E-3 was followed except that CE-39 was used in place of CE-2 to produce 3-(4-fluorophenyl)-3-(4-(4-((1,1,1,5,5,5-hexamethyl-3-((trimethylsilyl)oxy)trisiloxan-3-yl)oxy)piperidin-1-yl)phenyl)-7-methoxy- 11-phenyl-13,13-dimethyl-3H,13H indeno[2,1-f]naphtho[1,2-b]pyran. The structure was supported by NMR analysis.

E-47

The procedure described for E-3 was followed except that CE-40 was used in place of CE-2 to produce 3-(4-fluorophenyl)-3-(4-(4-((1,1,1,5,5,5-hexamethyl-3-((trimethylsilyl)oxy)trisiloxan-3-yl)oxy)piperidin-1-yl)phenyl)-13,13-dimethyl-3H,13H indeno[2,1-f]naphtho[1,2-b]pyran. The structure was supported by NMR analysis.

E-48

The procedure described for E-3 was followed except that CE-47 was used in place of CE-2 to produce 3-(4-fluorophenyl)-3-(4-(4-(((1,1,1,5,5,5-hexamethyl-3-((trimethylsilyl)oxy)trisiloxan-3-yl)oxy)methyl)piperidin-1-yl)phenyl)-13,13-dimethyl-3H,13H indeno[2,1-f]naphtho[1,2-b]pyran. The structure was supported by NMR analysis.

E-49

The procedure used in E-9 was followed except that CE-21 was used instead of CE-4. NMR analysis showed the product to be consistent with the structure of 3-(4-(2-(3-(1,1,1,3,5,5,5-heptamethyltrisiloxan-3-yl)propoxy)ethoxy)phenyl)-3-(4-methoxyphenyl)-6-methoxy-7-(3-(hydroxymethyl)piperidin-1-yl)-11-hexylcarbamoyl -13,13-dimethyl-3H,13H indeno[2',2':3,4]naphtho[1,2-b]pyran with 9 units of caprolactone monomers polymerized at the hydroxyl functionality.

E-50

The procedure described for E-3 was followed except that CE-42 was used in place of CE-2 to produce 3-(4-(2-(((1,1,1,5,5,5-hexamethyl-3-trimethylsilyl)oxy)trisiloxan-3-yl)oxy)methyl)morpholino)phenyl)-3-(4-methoxyphenyl)-7-methoxy-11-phenyl-13,13-dimethyl-3H,13H indeno[2,1-f]naphtho[1,2-b]pyran. The structure was supported by NMR analysis.

E-51

The procedure described for E-3 was followed except that CE-43 was used in place of CE-2 to produce 3-(4 (4-(2-((1,1,1,5,5,5-hexamethyl-3-((trimethylsilyl)oxy)trisiloxan-3-yl)oxy)ethyl)piperazin-1-yl)phenyl)-3-(4-fluorophenyl)-7-methoxy-11-phenyl-13,13-dimethyl-3H,13H indeno[2,1-f]naphtho[1,2-b]pyran. The structure was supported by NMR analysis.

E-52

The procedure used in E-9 was followed except that CE-44 was used instead of CE-4 and to produce 3-(4-(3-(1,1,1,3,5,5,5-heptamethyltrisiloxan-3-yl)propoxy)phenyl)-3-(4-morpholinophenyl)-7-methoxhy-11-phenyl-13,13-dimethyl-3H,13H indeno[2,1-f]naphtho[1,2-b]pyran. The structure was supported by NMR analysis.

E-53

The preparation described for E-2 was used except that CE-45 was used instead of CE-2 to produce 3-(4-fluorophenyl)-3-(4-(4-(4-((3-(1,1,1,3,5,5,5-heptamethyltrisiloxan-3-yl)propyl)amino)-4-oxobutanoyl)piperazin-1-yl)phenyl)-13,13-dimethyl-3H,13H indeno[2,1-f]naphtho[1,2-b]pyran. The structure was supported by NMR analysis.

E-54

The procedure used in E-9 was followed except that CE-20 was used instead of CE-4 and to produce 3-(4-(2-(3-(1,1,1,3,5,5,5-heptamethyltrisiloxan-3-yl)propoxy)ethoxy)phenyl)-3-(4-methoxyphenyl)-6-methoxy-7-(3-(hydroxymethyl)piperidin-1-yl)-11-hexylcarbamoyl -13,13-dimethyl-3H,13H indeno[2',3':3,4]naphtho[1,2-b]pyran. The structure was supported by NMR analysis.

E-55

The procedure described for E-1 was followed except that CE-13 was used in place of CE-2 to produce 3-(4-(2-(((2-(1,1,1,5,5,5-hexamethyl-3-((trimethylsilyl)oxy)trisiloxan-3-yl)ethyl)dimethylsilyl)oxy)ethoxy)phenyl)-3-(4-morpholinophenyl)-7-methoxy-11-phenyl-13,13-dimethyl-3H,13H indeno[2,1-f]naphtho[1,2-b]pyran. The structure was supported by NMR analysis.

E-56

The procedure described for E-1 was followed except that CE-26 was used in place of CE-2 to produce 3-(4-fluorophenyl)-3-(4-(2-(((2-(1,1,1,5,5,5-hexamethyl-3-((trimethylsilyl)oxy)trisiloxan-3-yl)ethyl)dimethylsilyl)oxy)ethoxy)phenyl)-7-methoxy-11-phenyl-13,13-dimethyl-3H,13H indeno[2,1-f]naphtho[1,2-b]pyran. The structure was supported by NMR analysis.

E-57

The procedure described for E3 was followed except that CE-47 was used in place of CE-2 to produce 3-(4-(2-((1,1,1,5,5,5-hexamethyl-3-((trimethylsilyl)oxy)trisiloxan-3-yl)oxy)ethoxy)phenyl)-3-(4-morpholinophenyl)-6-methoxy-7-(piperidin 1-yl)-11-phenyl-13,13-dimethyl-3H,13H indeno[2,1-f]naphtho[1,2-b]pyran. The structure was supported by NMR analysis.

E-58

The procedure described for E-3 was followed except that CE-48 was used in place of CE-2 to produce 3-(4-(2-(((1,1,1,5,5,5-hexamethyl-3-((trimethylsilyl)oxy)trisiloxan-3-yl)oxy)methyl)morpholino)phenyl)-3-(4-fluorophenyl)-6,7-dimethoxy-11-(4-(trifluoromethyl)phenyl)-13,13-dimethyl-3H,13H indeno[2,1-f]naphtho[1,2-b]pyran. The structure was supported by NMR analysis.

E-59

The procedure described for E-3 was followed except that CE-49 was used in place of CE-2 to produce 3-(4-(4-(2-((1,1,1,5,5,5-hexamethyl-3-((trimethylsilyl)oxy)trisiloxan-3-yl)oxy)ethyl)piperazin-1-yl)phenyl)-3-(4-fluorophenyl)-7-13,3-dimethyl-3H,13H indeno[2,1-f]naphtho[1,2-b]pyran. The structure was supported by NMR analysis.

E-60

The procedure described for E-3 was followed except that CE-50 was used in place of CE-2 to produce 3-(4-(2-(((1,1,1,5,5,5-hexamethyl-3-((trimethylsilyl)oxy)trisiloxan-3-yl)

oxy)ethoxy)phenyl)-3-(4-methoxyphenyl)-7-methoxy-11-phenyl-13,13-diethyl-3H,13H indeno[2,1-f]naphtho[1,2-b]pyran. The structure was supported by NMR analysis.

E-61

The procedure described for E-3 was followed except that CE-51 was used in place of CE-2 to produce 3-(4-(2-((1,1,1,5,5,5-hexamethyl-3-((trimethylsilyl)oxy)trisiloxan-3-yl)oxy)ethoxy)phenyl)-3-(4-methoxyphenyl)-6,7-dimethoxy-11-(4-cyanophenyl)-13,13-dimethyl-3H,13H indeno[2,1-f]naphtho[1,2-b]pyran. The structure was supported by NMR analysis.

E-62

The procedure described for E-3 was followed except that CE-52 was used in place of CE-2 to produce 3-(4-fluorophenyl)-3-(4-(2-(((1,1,1,5,5,5-hexamethyl-3-((trimethylsilyl)oxy)trisiloxan-3-yl)oxy)methyl)piperidin-1-yl)phenyl)-13,13-dimethyl-3H,13H indeno[2,1-f]naphtho[1,2-b]pyran. The structure was supported by NMR analysis.

E-63

The procedure described for E-3 was followed except that CE-53 was used in place of CE-2 to produce 3-(4-(2-((1,1,1,5,5,5-hexamethyl-3-((trimethylsilyl)oxy)trisiloxan-3-yl)oxy)ethoxy)phenyl)-3-(4-morpholinophenyl)-6-methoxy-7-(piperidin1-yl)-11-(2-(trifluoromethyl)phenyl)-13,13-dimethyl-3H,13H indeno[2,1-f]naphtho[1,2-b]pyran. The structure was supported by NMR analysis.

E-64

The procedure described for E-3 was followed except that CE-54 was used in place of CE-2 to produce 3-(4-fluorophenyl)-3-(4-(3-((1,1,1,5,5,5-hexamethyl-3-((trimethylsilyl)oxy)trisiloxan-3-yl)oxy)methyl)piperidin-1-yl)phenyl)-6,7-dimethoxy-11-(4-(trifluoromethyl)phenyl)-13,13-dimethyl-31,13H indeno[2,1-f]naphtho[1,2-b]pyran. The structure was supported by NMR analysis.

E-65

The procedure described for E-3 was followed except that CE-55 was used in place of CE-2 to produce 3-(4-(2-((1,1,1,5,5,5-hexamethyl-3-((trimethylsilyl)oxy)trisiloxan-3-yl)oxy)ethoxy)phenyl)-3-(4-methoxyphenyl)-6,7-dimethoxy-11-(4-(trifluoromethyl)phenyl)-13,13-dimethyl-3H,13H indeno[2,1-f]naphtho[1,2-b]pyran. The structure was supported by NMR analysis.

E-66

The procedure described for E-3 was followed except that CE-56 was used in place of CE-2 to produce 3-(4-fluorophenyl)-3-(4-(3-(((1,1,1,5,5,5-hexamethyl-3-((trimethylsilyl)oxy)trisiloxan-3-yl)oxy)methyl)piperidin-1-yl)phenyl)-6,7-dimethoxy-11-(phenylethynyl)-13,13-dimethyl-3H,13H indeno[2,1-f]naphtho[1,2-b]pyran. The structure was supported by NMR analysis.

E-67

The procedure describe for the preparation of E-22 was followed except that CE-57 was used in place of CE-25 to produce 3-(4-((2-(1,1,1,5,5,5-hexamethyl-3-((trimethylsilyl)oxy)trisiloxan-3-yl)ethyl)dimethylsilyl)phenyl-3-phenyl-13,13-dimethyl-3H,13H indeno[2,1-f]naphtho[1,2-b]pyran. The structure was supported by NMR analysis.

E-68

The procedure described for E-3 was followed except that CE-58 was used in place of CE-2 to produce 3-(4-(2-((1,1,1,5,5,5-hexamethyl-3-((trimethylsilyl)oxy)trisiloxan-3-yl)oxy)ethoxy)phenyl)-3-(4-fluorophenyl)-6,7-dimethoxy-11-cyano-13,13-dimethyl-3H,13H indeno[2,1-f]naphtho[1,2-b]pyran. The structure was supported by NMR analysis.

E-69

The procedure described for E-3 was followed except that CE-59 was used in place of CE-2 to produce 3-(4-(2-((1,1,1,5,5,5-hexamethyl-3-((trimethylsilyl)oxy)trisiloxan-3-yl)oxy)ethoxy)phenyl)-3-(4-methoxyphenyl)-6,7-dimethoxy-11-cyano-13,13-dimethyl-3H,13H indeno[2,1-f]naphtho[1,2-b]pyran. The structure was supported by NMR analysis.

E-70

The procedure described for E1 was followed except that CE-28 was used in place of CE-2 to produce 3-(4-(2-(((2-(1,1,1,5,5,5-hexamethyl-3-((trimethylsilyl)oxy)trisiloxan-3-yl)ethyl)dimethylsilyl)oxy)ethoxy)phenyl)-3-(4-methoxyphenyl)-6,11,13-trimethyl-13-methoxy-3H,13H indeno[2,1-f]naphtho[1,2-b]pyran. The structure was supported by NMR analysis.

E-71

The procedure described for E-3 was followed except that CE-60 was used in place of CE-2 to produce 3-(4-(2-((1,1,1,5,5,5-hexamethyl-3-((trimethylsilyl)oxy)trisiloxan-3-yl)oxy)ethoxy)phenyl)-3-(4-methoxyphenyl)-6-methoxy-7-(diethylamino)-11-(trifluoromethyl)-13,13-dimethyl-3H,13H indeno[2,1-f]naphtho[1,2-b]pyran. The structure was supported by NMR analysis.

E-72

The procedure used in E-9 was followed except that CE-61 was used instead of CE-4 to produce 3-(3-(2-(1,1,1,3,5,5,5-heptamethyltrisiloxan-3-yl)ethyl)-4-methoxy)phenyl)-3-phenyl-6,11-difluoro-13,13-dimethyl-3H,13H indeno[2,1-f]naphtho[1,2-b]pyran. The structure was supported by NMR analysis.

E-73

The procedure described for E-3 was followed except that CE-62 was used in place of CE-2 to produce 3-(3-(2-((1,1,1,5,5,5-hexamethyl-3-((trimethylsilyl)oxy)trisiloxan-3-yl)oxy)ethyl)-4-methoxy)phenyl)-3-phenyl-6,11-difluoro-13,13-dimethyl-3H,13H indeno[2,1-f]naphtho[1,2-b]pyran. The structure was supported by NMR analysis.

E-74

The procedure described in E-73 was followed except that tris(trimethylsiloxy)silane was used instead of bis(trimethylsiloxy)methylsilane to produce 3-(3-(2-(1,1,1,5,5,5-hexamethyl-3-((trimethylsilyl)oxy)trisiloxan-3-yl)ethyl)-4-methoxy)phenyl)-3-phenyl-6,11-difluoro-13,13-dimethyl-3H, 13H indeno[2,1-f]naphtho[1,2-b]pyran. The structure was supported by NMR analysis.

E-75

The procedure described for E-3 was followed except that CE-63 was used in place of CE-2 to produce 3-(3-(1-((1,1,1, 5,5,5-hexamethyl-3-((trimethylsilyl)oxy)trisiloxan-3-yl) oxy)ethyl)-4-methoxy)phenyl)-3-phenyl-6,11-difluoro-13, 13-dimethyl-3H,13H indeno[2,1-f]naphtho[1,2-b]pyran. The structure was supported by NMR analysis.

E-76

The procedure used in E-9 was followed except that CE-41 was used instead of CE-4 to produce 3-(3-(2-(1,1,1,3,5,5,5-heptamethyltrisiloxan-3-yl)ethyl)-4-methoxy)phenyl)-3-(4-morpholinophenyl)-13,13-dimethyl-3H,13H indeno[2,1-f] naphtho[1,2-b]pyran. The structure was supported by NMR analysis.

E-77

The procedure described for E-1 was followed except that CE-5 was used in place of CE-2 and the stochiometry of the reaction adjusted to produce 3-(4-(2-(((2-(1,1,1,5,5,5-hexamethyl-3-((trimethylsilyl)oxy)trisiloxan-3-yl)ethyl)dimethylsilyl)oxy)ethoxy)phenyl)-3-(4-methoxyphenyl)-6,11, 13-trimethyl-13-((2,2,7,7-tetramethyl-4,4-bis ((trimethylsilyl)oxy)-3,8,11,14-tetraoxa-2,4,7-trisilahexadecan-16-yl)oxy)-3H,13H indeno[2,1-f]naphtho [1,2-b]pyran. The structure was supported by NMR analysis.

E-78

The procedure described for E-3 was followed except that CE-65 was used in place of CE-2 and the stochiometry of the reaction adjusted to produce 3,3-bis(4-(2-((1,1,1,5,5,5-hexamethyl-3-((trimethylsilyl)oxy)trisiloxan-3-yl)oxy)ethoxy) phenyl)-13,13-dimethyl-3H,13H indeno[2,1-f]naphtho[1,2-b]pyran. The structure was supported by NMR analysis.

E-79

The procedure described for E-3 was followed except that CE-66 was used in place of CE-2 and the stoichiometry of the reaction adjusted to produce 3,3-di(4-methoxyphenyl)-6,7-dimethoxy-1'-(3,5-bis(((1,1,1,5,5,5-hexamethyl-3-((trimethylsilyl)oxy)trisiloxan-3-yl)oxy)methyl)phenyl)-13,13-dimethyl-3H,13H indeno[2',3':3,4]naphtho[1,2-b]pyran. The structure was supported by NMR analysis.

E-80

The procedure used in E-9 was followed except that CE-67 was used instead of CE-4 and the stoichiometry adjusted to produce 3,3-bis(4-(3-(1,1,1,3,5,5,5-heptamethyltrisiloxan-3-yl)propoxy)phenyl)-6-methoxy-7-(3-hydroxymethyl)piperidin-1-yl)-11-hexylcarbamoyl-13,13-dimethyl-3H,13H indeno[2,1-f]naphtho[1,2-b]pyran. The structure was supported by NMR analysis.

E-81

The procedure described for E-3 was followed except that CE-68 was used in place of CE-2 and the stoichiometry of the reaction adjusted to produce 3,3-bis(4-(2-((1,1,1,5,5,5-hexamethyl-3-((trimethylsilyl)oxy)trisiloxan-3-yl)oxy)ethoxy) phenyl)-6,11-difluoro-13,13-dimethyl-3H,13H indeno[2,1-f]naphtho[1,2-b]pyran. The structure was supported by NMR analysis.

E-82

The procedure described for E-1 was followed except that CE-69 was used in place of CE-2 and the stoichiometry of the reaction adjusted to produce 3,3-(di(4-methoxyphenyl)-6,11, 13-trimethyl-13-((11-(2-(((2-(1,1,1,5,5,5-hexamethyl-3-((trimethylsilyl)oxy)trisiloxan-3-yl)ethyl)dimethylsilyl) oxy)ethyl)-2,2,7,7-tetramethyl-12,15-dioxo-4,4-bis ((trimethylsilyl)oxy)-3,8,16,19,22-pentaoxa-11-aza-2,4,7-trisilatetracosan-24-yl)oxy)-3H,13H indeno[2,1-f]naphtho [1,2-b]pyran. The structure was supported by NMR analysis.

E-83

The procedure described for E-3 was followed except that CE-73 was used in place of CE-2 and the stoichiometry of the reaction adjusted to produce 3,3-bis(4-(2-((1,1,1,5,5,5-hexamethyl-3-((trimethylsilyl)oxy)trisiloxan-3-yl)oxy)ethoxy) phenyl)-6-methoxy-7-(piperidin1-yl)-13,13-dimethyl-3H, 13H indeno[2,1-f]naphtho[1,2-b]pyran. The structure was supported by NMR analysis.

E-84

The preparation described for E-2 was used except that CE-72 was used instead of CE-2 and the stoichiometry of the reaction adjusted to produce 3-(4-(2-((4-((3-(1,1,1,3,5,5,5-heptamethyltrisiloxan-3-yl)propyl)amino)-4-oxobutanoyl) oxy)ethoxy)phenyl)-3-(4-methoxyphenyl)-6,11,13-trimethyl-13-((2,2,4-trimethyl-9,12-dioxo-4-((trimethylsilyl) oxy)-3,13,16,19-tetraoxa-8-aza-2,4-disilahenicosan-21-yl) oxy)-3,8,11,14-tetraoxa-2,4,7-trisilahexadecan-16-yl)oxy)-3H,13H indeno[2,1-f]naphtho[1,2-b]pyran. The structure was supported by NMR analysis.

E-85

The procedure described for E-1 was followed except that CE-71 was used in place of CE-2 and the stoichiometry of the reaction adjusted to produce 3-(4-(2-(((2-(1,1,1,5,5,5-hexamethyl-3-((trimethylsilyl)oxy)trisiloxan-3-yl)ethyl)dimethylsilyl)oxy)ethoxy)phenyl)-3-(4-methoxyphenyl)-6-methoxy-7-(3-(((((2-(1,1,1,5,5,5-hexamethyl-3-((trimethylsilyl)oxy)trisiloxan-3-yl)ethyl)dimethylsilyl) oxy)methyl)piperidin-1-yl)-13,13-dimethyl-3H,13H indeno [2',3':3,4]naphtho[1,2-b]pyran. The structure was supported by NMR analysis.

E-86

The procedure used for the preparation of E-39 was followed except that CE-65 was used in place of CE-33 and the stoichiometry of the reagents adjusted to produce 3,3-bis(4-(2-((tri-tert-butoxysilyl)oxy)ethoxy)phenyl)-13,13-dimethyl-3H,13H indeno[2,1-f]naphtho[1,2-b]pyran. The structure was supported by NMR analysis.

E-87

The procedure described for E-1 was followed except that Tri-t-terbutoxychlorosilane was used in place of [tris(trimethylsiloxy)silylethyl]dimethyl-chlorosilane to produce 3,3-(di (4-methoxyphenyl)-6,11,13-trimethyl-13-((4,4-di-tert-butoxy-2,2-dimethyl-3,5,8,11-tetraoxa-4-silatridecan-13-yl) oxy)-3,8,11,14-tetraoxa-2,4,7-trisilahexadecan-16-yl)oxy)-3H,13H indeno[2,1-f]naphtho[1,2-b]pyran. The structure was supported by NMR analysis.

Part 4—Photochromic Performance Testing of Examples (E) and Comparative Examples (CE)

Part A—Test Square Preparation

Testing was done with the compounds described in Examples 1-87 and Comparative Examples 1-5, 7-24, 26-30, 32-36, 38-40, 42-56, 58-60, 62, 64, 66, 67, 69, 71 and 74-77 in the following manner. A quantity of compound calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly (ethylene glycol) 600 dimethacrylate, and 0.033 weight percent 2,2'-azobis(2-methyl propionitrile) (AIBN). Each compound was dissolved into the monomer blend by stirring and gentle heating, if necessary. After a clear solution was obtained, the sample was degassed in a vacuum oven for 5-10 minutes at 25 torr. Using a syringe, the sample was poured into a flat sheet mold having an interior dimension of 2.2 mm+/−0.3 mm×6 inch (15.24 cm)×6 inch (15.24 cm). The mold was sealed and placed in a horizontal airflow, programmable oven to ramp from 40° C. to 95° C. over a 5 hour interval, hold the temperature at 95° C. for 3 hours, ramp down to 60° C. over a 2 hour interval and then hold at 60° C. for 16 hours. After curing, the mold was opened, and the polymer sheet was cut into 2 inch (5.1 cm) test squares using a diamond blade saw.

Part B—Response Testing

Prior to response testing on an optical bench, the test squares from Part A were conditioned by exposing them to 365 nm ultraviolet light for 10 minutes at a distance of about 14 cm from the source in order to pre-activate the photochromic compounds in samples. The UVA irradiance at the sample surface was measured with a Licor Model Li-1800 spectroradiometer and found to be 22.2 Watts per square meter. The samples were then placed under a halogen lamp (500 W, 120V) for about 10 minutes at a distance of about 36 cm from the lamp in order to bleach, or inactivate, the photochromic compounds in the samples. The illuminance at the sample was measured with the Licor spectroradiometer and found to be 21.9 Klux. The samples were then kept in a dark environment for at least 1 hour prior to testing in order to cool and continue to fade back to a ground state.

The optical bench was fitted with an Newport Model #67005 300-watt Xenon arc lamp, and Model 69911 power supply, Vincent Associates (model VS25S2ZM0R3 with VMM-D4 controller) high-speed computer controlled shutter, a Schott 3 mm KG-2 band-pass filter, which removed short wavelength radiation, neutral density filter(s) to attenuate light from the xenon lamp, a fused silica condensing lens for beam collimation, and a fused silica water cell/sample holder for maintaining sample temperature in which the test sample to be tested was inserted. The temperature in the water cell was controlled with a pumped water circulation system in which the water passed through copper coils that were placed in the reservoir of a chiller unit. The water cell used to hold test samples contained fused silica sheets on the front and back facings in order to eliminate spectral change of the activation or monitoring light beams. The filtered water passing through the water cell was maintained at 72° F.−2° for photochromic response testing. A Newport Model 689456 Digital Exposure Timer was used to control the intensity of the xenon arc lamp during activation of the sample.

A broadband light source for monitoring response measurements was positioned in a perpendicular manner to a surface of the cell assembly. Increased signal of shorter visible wavelengths was obtained by collecting and combining separately filtered light from a 100-Watt tungsten halogen lamp (controlled by a Lambda UP60-14 constant voltage powder supply) with a split-end, bifurcated fiber optical cable. Light from one side of the tungsten halogen lamp was filtered with a Schott KG1 filter to absorb heat and a Hoya B-440 filter to allow passage of the shorter wavelengths. The other side of the light was either filtered with a Schott KG1 filter or unfiltered. The light was collected by focusing light from each side of the lamp onto a separate end of the split-end, bifurcated fiber optic cable, and subsequently combined into one light source emerging from the single end of the cable. A 4" (10.2 cm) light pipe was attached to the single end of the cable to insure proper mixing. After passing through the sample, the light was refocused into a 2-inch (4.5 cm) integrating sphere and fed to an Ocean Optics S2000 spectrophotometer by fiber optic cables. Ocean Optics SpectraSuite and PPG proprietary software were used to measure response and control the operation of the optical bench.

Irradiance for response testing of the samples on the optical bench was established at the sample surface using an International Light Research Radiometer, Model IL-1700 with a detector system comprising a Model SED033 detector, B Filter and diffuser. The output display of the radiometer was corrected (factor values set) against a Licor 1800-02 Optical Calibration Calibrator in order to display values representing Watts per square meter UVA. The irradiance at the sample point for initial response testing was set at to 3.0 Watts per square meter UVA and approximately 8.6 Klux illuminance. During sample response testing, if a sample darkened beyond an acceptable detection capability limit, the irradiance was lowered to 1.0 Watts per square meter UVA or the sample was remade at a one-half concentration in the copolymer. Adjusting the output of the filtered xenon arc lamp was accomplished by increasing or decreasing the current to the lamp through the controller and/or by adding or removing neutral density filters in the light path. The test samples were exposed to the activation light at 31° normal to its surface while being perpendicular to the monitoring light.

Samples were activated in the 73° F. (22.8° C.) controlled water cell for 30 minutes, then allowed to fade under room light conditions until the change in optical density of the activated sample faded to ¼ of its highest dark (saturated) state or for a maximum of 30 minutes of fade.

Change in optical density (ΔOD) from the bleached state to the darkened state was determined by establishing the initial transmittance, opening the shutter from the Xenon lamp to provide ultraviolet radiation to change the test lens from the bleached state to an activated (i.e., darkened) state. Data was collected at selected intervals of time, measuring the transmittance in the activated state, and calculating the change in optical density according to the formula: ΔOD=log(% Tb/% Ta), where % Tb is the percent transmittance in the bleached state, % Ta is the percent transmittance in the activated state and the logarithm is to the base 10.

The $\lambda_{max\text{-}vis}$ in the visible light range is the wavelength in the visible spectrum at which the maximum absorption of the activated form of the photochromic compound occurs. The $\lambda_{max\text{-}vis}$ was determined by testing the photochromic test square in a Varian Cary 4000 UV-Visible spectrophotometer or comparable equipment.

The ΔOD/Min, which represents the sensitivity of the photochromic compound's response to UV light, was measured over the first five (5) seconds of UV exposure, then expressed on a per minute basis. The saturation optical density (ΔOD at saturation) was taken under identical conditions except UV exposure was continued for a total of 30 minutes. The fade half life is the time interval in seconds for the ΔOD of the activated form of the photochromic compound in the test squares to reach one half the ΔOD measured after thirty minutes, or after saturation or near-saturation was achieved, at room temperature after removal of the source of activating light, e.g., by closing the shutter. Results are listed in Table I. Double lines in Table 1 were used to separate the individual groups of examples and their respective comparative examples.

TABLE 1

Photochromic Performance Test Results

| E-#'s & CE-#'s | $\lambda_{max\text{-}vis}$ (nm) | Sensitivity (ΔOD/Min) | ΔOD at saturation | T ½ (sec) |
|---|---|---|---|---|
| E-8 | 566 | 0.714 | 0.945 | 123 |
| CE-1 | 575 | 0.27 | 0.5 | 119 |
| E-1 | 572 | 0.552 | 0.652 | 84 |
| E-3 | 572 | 0.636 | 0.666 | 74 |
| E-4 | 572 | 0.534 | 0.627 | 83 |
| E-12 | 567 | 0.762 | 0.636 | 56 |
| E-87 | 566 | 0.594 | 0.657 | 76 |
| CE-2 | 570 | 0.49 | 0.64 | 104 |
| E-6 | 572 | 0.558 | 0.592 | 74 |
| E-7 | 572 | 0.582 | 0.673 | 85 |
| CE-3 | 572 | 0.486 | 0.641 | 97 |
| E-9 | 572 | 0.57 | 0.778 | 112 |
| CE-4 | 572 | 0.456 | 0.723 | 130 |
| E-77 | 573 | 0.648 | 0.679 | 74 |
| E-84 | 572 | 0.666 | 0.72 | 80 |
| CE-5 | 572 | 0.516 | 0.676 | 99 |
| E-17 | 577 | 0.348 | 0.551 | 129 |
| CE-11 | 577 | 0.29 | 0.51 | 157 |
| E-11 | 567 | 0.636 | 0.707 | 91 |
| CE-7 | 572 | 0.492 | 0.742 | 124 |
| E-10 | 596 | 0.546 | 0.515 | 58 |
| CE-8 | 595 | 0.45 | 0.49 | 79 |
| E-13 | 595 | 0.696 | 0.519 | 56 |
| CE-9 | 599 | 0.57 | 0.58 | 90 |
| E-35 | 560 | 0.648 | 0.871 | 129 |
| CE-10 | 558 | 0.558 | 0.861 | 159 |
| E-36 | 576 | 0.36 | 0.58 | 124 |
| CE-11 | 577 | 0.29 | 0.51 | 157 |
| E-40 | 586 | 0.66 | 0.76 | 78 |
| CE-12 | 588 | 0.486 | 0.617 | 86 |
| E-24 | 580 | 0.69 | 1.101 | 173 |
| E-38 | 583 | 0.684 | 1.057 | 160 |
| E-55 | 584 | 0.672 | 1.01 | 170 |
| CE-13 | 584 | 0.642 | 1.006 | 151 |
| E-43 | 591 | 0.84 | 0.911 | 173 |
| CE-14 | 593 | 0.732 | 0.813 | 158 |
| E-37 | 576 | 0.324 | 0.663 | 247 |
| CE-15 | 577 | 0.306 | 0.74 | 306 |
| E-41 | 571 | 0.108 | 0.432 | 344 |
| CE-16 | 571 | 0.09 | 0.415 | 389 |
| E-42 | 572 | 0.75 | 0.888 | 136 |
| CE-17 | 573 | 0.636 | 0.795 | 138 |
| E-44 | 586 | 0.888 | 1.077 | 285 |
| CE-18 | 589 | 0.672 | 0.866 | 262 |
| E-45 | 567 | 0.672 | 0.883 | 140 |
| CE-19 | 572 | 0.594 | 0.827 | 148 |
| E-54 | 487 | 1.128 | 1.711 | 225 |
| CE-20 | 488 | 0.942 | 1.627 | 233 |
| E-49 | 481 | 1.026 | 1.279 | 153 |
| CE-21 | 482 | 1.008 | 1.473 | 182 |
| E-18 | 577 | 0.384 | 0.77 | 222 |
| CE-22 | 578 | 0.33 | 0.77 | 274 |
| E-19 | 584 | 0.438 | 0.74 | 214 |
| CE-23 | 586 | 0.36 | 0.70 | 264 |
| E-20 | 590 | 0.09 | 0.403 | 410 |
| CE-24 | 590 | 0.09 | 0.405 | 405 |
| E-21 | 580 | 0.408 | 0.784 | 266 |
| E-22 | 576 | 0.396 | 0.772 | 214 |
| CE-75 | 576 | 0.34 | 0.73 | 285 |
| E-23 | 589 | 0.828 | 1.336 | 187 |

TABLE 1-continued

Photochromic Performance Test Results

| E-#'s & CE-#'s | $\lambda_{max\text{-}vis}$ (nm) | Sensitivity (ΔOD/Min) | ΔOD at saturation | T ½ (sec) |
|---|---|---|---|---|
| E-56 | 590 | 0.69 | 1.245 | 198 |
| CE-26 | 595 | 0.642 | 1.126 | 203 |
| E25 | 556 | 0.684 | 1.165 | 229 |
| CE-27 | 557 | 0.636 | 1.1 | 237 |
| E-70 | 572 | 0.552 | 0.76 | 110 |
| CE-28 | 572 | 0.45 | 0.696 | 124 |
| E-26 | 572 | 0.57 | 0.763 | 105 |
| CE-29 | 572 | 0.498 | 0.761 | 124 |
| E-27 | 572 | 0.582 | 0.497 | 54 |
| E-28 | 566 | 0.60 | 0.518 | 55 |
| E-29 | 567 | 0.606 | 0.492 | 51 |
| CE-30 | 568 | 0.50 | 0.51 | 67 |
| E-30 | 616 | 0.714 | 0.749 | 69 |
| CE-32 | 618 | 0.55 | 0.70 | 89 |
| E-31 | 557 | 0.66 | 0.878 | 104 |
| E-39 | 558 | 0.648 | 0.868 | 109 |
| CE-33 | 558 | 0.57 | 0.84 | 115 |
| E-32 | 607 | 0.456 | 0.893 | 247 |
| CE-34 | 607 | 0.366 | 0.736 | 236 |
| E-33 | 572 | 0.312 | 0.432 | 90 |
| CE-35 | 572 | 0.24 | 0.37 | 98 |
| E-34 | 593 | 0.78 | 1.021 | 92 |
| CE-36 | 600 | 0.61 | 0.94 | 107 |
| E-46 | 586 | 0.744 | 1.302 | 202 |
| CE-38 | 591 | 0.582 | 1.05 | 215 |
| E-47 | 588 | 0.738 | 1.001 | 104 |
| CE-39 | 593 | 0.612 | 0.92 | 114 |
| E-14 | 596 | 0.792 | 0.896 | 164 |
| CE-40 | 596 | 0.57 | 0.827 | 216 |
| E-76 | 587 | 0.636 | 0.836 | 105 |
| CE-77 | 588 | 0.57 | 0.717 | 93 |
| E-50 | 579 | 0.756 | 1.036 | 162 |
| CE-42 | 583 | 0.402 | 0.679 | 189 |
| E-51 | 580 | 0.738 | 1.309 | 236 |
| CE-43 | 580 | 0.546 | 1.098 | 284 |
| E-52 | 584 | 0.522 | 0.795 | 169 |
| CE-44 | 583 | 0.57 | 0.912 | 179 |
| E-53 | 580 | 0.666 | 1.054 | 131 |
| CE-45 | 580 | 0.57 | 1.041 | 153 |
| E-48 | 592 | 0.762 | 0.977 | 92 |
| CE-46 | 596 | 0.588 | 0.866 | 110 |
| E-57 | 597 | 0.444 | 0.92 | 296 |
| CE-47 | 599 | 0.378 | 0.818 | 298 |
| E-58 | 601 | 0.498 | 0.793 | 180 |
| CE-48 | 604 | 0.396 | 0.707 | 196 |
| E-59 | 583 | 0.72 | 1.079 | 117 |
| CE-49 | 583 | 0.552 | 0.982 | 142 |
| E-60 | 557 | 0.78 | 1.031 | 152 |
| CE-50 | 557 | 0.678 | 0.952 | 162 |
| E-61 | 581 | 0.516 | 0.616 | 153 |
| CE-51 | 581 | 0.43 | 0.59 | 186 |
| E-62 | 596 | 0.786 | 0.96 | 87 |
| CE-52 | 598 | 0.552 | 0.787 | 118 |
| E-63 | 571 | 0.408 | 0.814 | 249 |
| CE-53 | 572 | 0.378 | 0.802 | 247 |
| E-64 | 612 | 0.564 | 0.751 | 134 |
| CE-54 | 618 | 0.414 | 0.613 | 147 |
| E-65 | 580 | 0.414 | 0.657 | 174 |
| CE-55 | 580 | 0.354 | 0.591 | 191 |
| E-66 | 618 | 0.576 | 0.678 | 125 |
| CE-56 | 622 | 0.462 | 0.619 | 140 |
| E-67 | 538 | 0.666 | 1.709 | 756 |
| CE-76 | 532 | 0.41 | 1.5 | 723 |
| E-68 | 572 | 0.342 | 0.44 | 105 |
| CE-58 | 572 | 0.31 | 0.45 | 116 |
| E-69 | 578 | 0.354 | 0.368 | 67 |
| CE-59 | 578 | 0.31 | 0.37 | 78 |
| E-71 | 590 | 0.114 | 0.267 | 178 |
| CE-60 | 590 | 0.078 | 0.219 | 197 |
| E-72 | 561 | 0.642 | 0.906 | 137 |
| E-73 | 560 | 0.696 | 0.943 | 136 |
| E-74 | 562 | 0.654 | 0.913 | 135 |
| E-75 | 557 | 0.66 | 0.91 | 140 |
| CE-62 | 561 | 0.576 | 0.872 | 157 |
| E-16 | 556 | 0.762 | 0.907 | 117 |

TABLE 1-continued

Photochromic Performance Test Results

| E-#'s & CE-#'s | $\lambda_{max\text{-}vis}$ (nm) | Sensitivity ($\Delta$OD/Min) | $\Delta$OD at saturation | T ½ (sec) |
|---|---|---|---|---|
| CE-64 | 558 | 0.648 | 0.89 | 158 |
| E-78 | 556 | 0.726 | 0.873 | 95 |
| E-86 | 557 | 0.708 | 0.885 | 105 |
| CE-33 | 558 | 0.57 | 0.84 | 115 |
| E-79 | 583 | 0.384 | 0.611 | 206 |
| CE-66 | 584 | 0.228 | 0.451 | 255 |
| E-80 | 488 | 0.942 | 1.396 | 193 |
| CE-67 | 488 | 0.912 | 1.688 | 260 |
| E-81 | 572 | 0.66 | 0.472 | 42 |
| CE-30 | 568 | 0.50 | 0.51 | 67 |
| E-2 | 572 | 0.636 | 0.668 | 76 |
| E-5 | 573 | 0.678 | 0.665 | 70 |
| E-82 | 572 | 0.546 | 0.645 | 83 |
| CE-69 | 567 | 0.516 | 0.62 | 85 |
| E-85 | 481 | 0.3 | 1.117 | 350 |
| CE-71 | 482 | 0.246 | 1.07 | 375 |
| E-83 | 571 | 0.12 | 0.435 | 307 |
| CE-16 | 571 | 0.09 | 0.415 | 389 |
| E-15 | 565 | 0.702 | 0.796 | 99 |
| CE-74 | 566 | 0.552 | 0.811 | 138 |

Part 6—Preparation and Testing of Polyurethane Coatings with E-25 and CE-78

Part 6A—Preparation of Coating A containing CE-78

The following materials were added in the order described to a suitable vessel equipped with an agitator. Weight percent listed below is based on the total weight of the coating formulation.

| CHARGE 1 | |
|---|---|
| MATERIAL | WEIGHT PERCENT |
| CE-78 | 1.0071 |
| IRGANOX ® 245[1] | 0.3357 |
| TINUVIN ® 144[2] | 0.3357 |
| NMP[3] | 24.8350 |

[1]An antioxidant/stabilizer available from Ciba Specialty Chemicals Corp.
[2]A light stabilizer of the hindered amine class reported to have CAS# 63843-89-0 and is available from Ciba Specialty Chemicals.
[3]N-methylpyrrolidinone (biotechnical grade) available from Aldrich of Milwaukee, Wisconsin.

| CHARGE 2 | |
|---|---|
| MATERIAL | WEIGHT PERCENT |
| BYK ® 333[4] | 0.0400 |
| K-KAT ® 348[5] | 0.5307 |
| A-187[6] | 2.6504 |

[4]A polyether modified dimethylpolysiloxane compolymer, which is available from BYK-Chemie of Wallingford, Connecticut.
[5]A urethane catalyst reported to be a bismuth carboxylate available from King Industries Inc.
[6]A gamma-glycidoxypropyl trimethoxysilane, which is available from Osi Specities of Paris, France.

| CHARGE 3 | |
|---|---|
| MATERIAL | WEIGHT PERCENT |
| Poly(meth)acrylic Polyol[7] | 16.2907 |
| PC-1122[8] | 15.9854 |
| DESMODUR ® PL 340[9] | 9.8230 |
| HDI Biuret BI-7960[10] | 28.1663 |

[7]A poly(meth)acrylic polyol produced by following the procedure of Composition D of Example 1 in U.S. Pat. No. 6,187,444, which procedure is incorporated herein by reference, except that in Charge 2, the styrene was replaced with methyl methacrylate and 0.5% by weight, based on the total monomer weight, of triphenyl phosphite was added.
[8]Polycarbonate diol sold by Stahl, USA.
[9]A blocked aliphatic polyisocyanate based on IPDI available from Bayer US.
[10]A blocked hexamethylene diisocyanate available from Baxenden Chemical Co. of Lancashire, England.

Charge 1 was added to the vessel and mixed for approximately 30 minutes to dissolve the solids. Charge 2 was added to the solution and the resulting mixture was stirred for approximately 5 minutes. The materials of Charge 3 were added in the order listed to a separate container and mixed prior to adding it to the vessel containing Charges 1 and 2. The resulting mixture was stirred for 1 hour.

Part 6B—Preparation of Coating B Containing E-25

The following materials were added in the order described to a suitable vessel equipped with an agitator.

| CHARGE 1 | |
|---|---|
| MATERIAL | WEIGHT PERCENT |
| E-25 | 1.4387 |
| IRGANOX ® 245[1] | 0.4796 |
| TINUVIN ® 144[2] | 0.4796 |
| NMP[3] | 24.1156 |

| CHARGE 2 | |
|---|---|
| MATERIAL | WEIGHT PERCENT |
| BYK ® 333[4] | 0.0400 |
| K-KAT ® 348[5] | 0.5307 |
| A-187[6] | 2.6504 |

| CHARGE 3 | |
|---|---|
| MATERIAL | WEIGHT PERCENT |
| Poly(meth)acrylic Polyol[7] | 16.2907 |
| PC-1122[8] | 15.9854 |
| IPDI PL 340[9] | 9.8230 |
| HDI Biuret BI-7960[10] | 28.1663 |

Charge 1 was added to the vessel and mixed for approximately 30 minutes to dissolve the solids. Charge 2 was added to the solution and the resulting mixture was stirred for approximately 5 minutes. The materials of Charge 3 were added in the order listed to a separate container and mixed prior to adding it to the vessel containing Charges 1 and 2. The resulting mixture was stirred for 1 hour.

Part 6C—Preparation of a Protective Coating Formulation (PCF)

The PCF (Hard Coat) was prepared as follows: Charge 1 was added to a clean dry beaker and placed in an ice bath at 5° C. with stirring. Charge 2 was added and an exotherm raised the temperature of the reaction mixture to 50° C. The temperature of the resulting reaction mixture was cooled to 20-25° C. and Charge 3 was added with stirring, Charge 4 was added to adjust the pH from about 3 to about 5.5. Charge 5 was added and the solution was mixed for half an hour. The resulting solution was filtered through a nominal 0.45 micron capsule filter and stored at 4° C. until use.

| Charge 1 | |
|---|---|
| glycidoxypropyltrimethoxysilane) | 32.4 grams |
| methyltrimethoxysilane) | 345.5 grams |
| Charge 2 | |
| Solution of deionized water (DI) with nitric acid (nitric acid 1 g/7000 g) | 292 grams |
| Charge 3 | |
| DOWANOL ® PM solvent | 228 grams |
| Charge 4 | |
| TMAOH (25% tetramethylamonium hydroxide in MeOH) | 0.45 grams |
| Charge 5 | |
| BYK ®-306 surfactant | 2.0 grams |

Part 6D—Preparation of Coated Lenses

Finished single vision polycarbonate lenses having a diameter of 70 mm obtained from Gentex Optics were used. The test lenses were treated with a corona discharge from a Tantec EST-Electrical Service Treatment unit operating at 500 Watts and 54 kVA for 45 seconds. Coating A and Coating B were each applied by spin-coating separately to corona treated lens and cured at 125° C. for 60 minutes. The resulting cured coatings were approximately 20 microns thick. The coated test lenses were treated by corona discharge from a 3DT Flexidyne unit operating at 20 Hertz and 0.70 kilowatts for 35 seconds.

The hard coat solution (approximately 2 mL) prepared in Part 6C was spin coated at a rate of 2,550 revolutions per minute (rpm) for 10 seconds onto the cured coated substrates. Post curing of the coated substrates was completed at 60° C. for 30 minutes.

Part 6E—Photochromic Performance Testing

The photochromic performance of E-25 and CE-78 in the aforementioned coating compositions was performed as follows. The coated lenses prepared above were tested for photochromic response on the Bench for Measuring Photochromics ("BMP") optical bench made by Essilor, Ltd. France. The optical bench was maintained at a constant temperature of 73.4° F. (23° C.) during testing.

Prior to testing on the optical bench, each of the coated lenses were exposed to 365-nanometer ultraviolet light for about 10 minutes at a distance of about 14 centimeters to activate the photochromic materials. The UVA (315 to 380 nm) irradiance at the lens was measured with a LICOR® Model Li-1800 spectroradiometer and found to be 22.2 watts per square meter. The lens was then placed under a 500 watt, high intensity halogen lamp for about 10 minutes at a distance of about 36 centimeters to bleach (inactivate) the photochromic materials. The illuminance at the lens was measured with the LICOR® spectroradiometer and found to be 21.9 Klux. The lenses were then kept in a dark environment at room temperature (from 70 to 75° F., or 21 to 24° C.) for at least 1 hour prior to testing on an optical bench. Prior to optical bench measurement, the lenses were measured for ultraviolet absorbance at 390 nanometers.

The BMP optical bench was fitted with two 150-watt ORIEL® Model #66057 Xenon arc lamps at right angles to each other. The light path from Lamp 1 was directed through a 3 mm SCHOTT® KG-2 band-pass filter and appropriate neutral density filters that contributed to the required UV and partial visible light irradiance level. The light path from Lamp 2 was directed through a 3 mm SCHOTT® KG-2 band-pass filter, a SCHOTT® short band 400 nm cutoff filter and appropriate neutral density filters in order to provide supplemental visible light illuminance A 2 inch×2 inch (5.1 cm×5.1 cm) 50% polka dot beam splitter, at 45° to each lamp is used to mix the two beams. The combination of neutral density filters and voltage control of the Xenon arc lamp were used to adjust the intensity of the irradiance. Proprietary software i.e., BMPSoft version 2.1e was used on the BMP to control timing, irradiance, air cell and sample temperature, shuttering, filter selection and response measurement. A ZEISS® spectrophotometer, Model MCS 501, with fiber optic cables for light delivery through the lens was used for response and color measurement. Photopic response measurements, as well as the response at four select wavelengths, were collected on each lens.

The power output of the optical bench, i.e., the dosage of light that the lens was exposed to, was adjusted to 6.7 Watts per square meter ($W/m^2$) UVA, integrated from 315-380 nm and 50 Klux illuminance, integrated from 380-780 nm. Measurement of this power setpoint was made using an irradiance probe and the calibrated Zeiss spectrophotometer. The lens sample cell was fitted with a quartz window and self-centering sample holder. The temperature in the sample cell was controlled at 23° C. through the software with a modified Facis, Model FX-10, environment simulator. Measurement of the sample's dynamic photochromic response and color measurements was made using the same Zeiss spectrophotometer, with fiber optic cables for light delivery from a tungsten halogen lamp and through the sample. The collimated monitoring light beam from the fiber optic cable was maintained perpendicular to the test sample while passing through the sample and directed into a receiving fiber optic cable assembly attached to the spectrophotometer. The exact point of placement of the sample in the sample cell was where the activating xenon arc beam and the monitoring light beam intersected to form two concentric circles of light. The angle of incidence of the xenon arc beam at the sample placement point was≈30° from perpendicular.

Response measurements, in terms of a change in optical density ($\Delta OD$) from the unactivated or bleached state to the activated or colored state were determined by establishing the initial unactivated transmittance, opening the shutter from the Xenon lamp(s) and measuring the transmittance through activation at selected intervals of time. Change in optical density was determined according to the formula: $\Delta OD = \log(10)(\% Tb/\% Ta)$, where % Tb is the percent transmittance in the bleached state, % Ta is the percent transmittance in the activated state. Optical density measurements were based on photopic optical density.

The results of this testing are presented below in Table 2, wherein the ΔOD at saturation is after 15 minutes of activation and the Fade Half Life ("T½") value is the time interval in seconds for the ΔOD of the activated form of the photochromic material in the coating to reach one half the fifteen-minute ΔOD at 73.4° F. (23° C.), after removal of the activating light source. The ΔOD/Min, which represents the sensitivity of the photochromic compound's response to UV light, was measured over the first five (5) seconds of UV exposure, then expressed on a per minute basis.

TABLE 2

Photochromic Performance Results for E-25 & CE-78

| E-#'s & CE-#'s | Sensitivity (ΔOD/Min) | ΔOD at saturation | T ½ (sec) |
|---|---|---|---|
| E-25 | 0.39 | 0.80 | 144 |
| CE-78 | 0.34 | 0.71 | 144 |

The present invention has been described with reference to specific details of particular embodiments thereof. It is not intended that such details be regarded as limitations upon the scope of the invention except insofar as to the extent that they are included in the accompanying claims.

What is claimed is:

1. A photochromic material comprising, a photochromic compound comprising a photochromic substituent selected from the group consisting of photochromic pyrans, photochromic oxazines, and thermally reversible photochromic fulgides, wherein the photochromic substituent has bonded thereto at least one pendent silane group selected from the group consisting of, (i) pendent silane groups represented by the following general formula I,

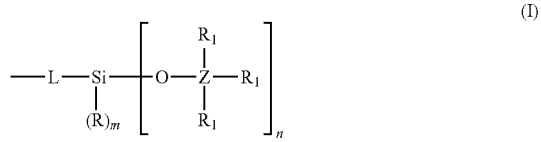

wherein Z for each n is independently Si or C, R is selected from hydrogen or $C_1$-$C_{10}$ hydrocarbyl, each $R_1$ is independently $C_1$-$C_{10}$ hydrocarbyl or halo substituted $C_1$-$C_{10}$ hydrocarbyl, m is 0 or 1, n is 2 or 3, provided that the sum of m and n is 3, and L is a divalent linking group comprising at least one divalent moiety selected from the group consisting of divalent organic moieties, divalent inorganic moieties and combinations thereof, (ii) pendent silane groups represented by the following general formula II,

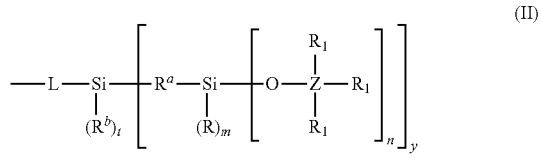

and combinations thereof, wherein Z, R, $R_1$, m, n and L are each independently as described with regard to general formula (I), $R^a$ is a divalent linking group selected from divalent organic moieties, $R^b$ is selected from hydrogen or $C_1$-$C_{10}$ hydrocarbyl, t is 0, 1 or 2, and y is 1, 2 or 3, provided that the sum of t and y is 3, wherein said divalent linking group of each L is independently selected from the group consisting of,

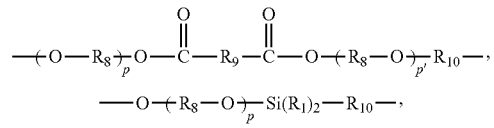

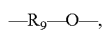

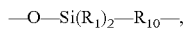

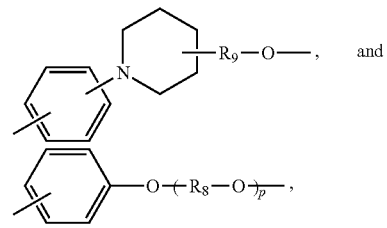

wherein each $R_1$ is independently as described with regard to general formula (I), $R_{10}$ in each instance is independently selected from the group consisting of substituted or unsubstituted linear or branched $C_1$-$C_{10}$ alkylene, substituted or unsubstituted linear or branched $C_2$-$C_{10}$ alkenylene, substituted or unsubstituted linear or branched $C_2$-$C_{10}$ alkynylene, substituted or unsubstituted $C_3$-$C_{10}$ cycloalkylene, and substituted or unsubstituted arylene, $R_8$ in each instance is independently selected from the group consisting of substituted or unsubstituted linear or branched $C_1$-$C_{20}$ alkylene, substituted or unsubstituted linear or branched $C_2$-$C_{20}$ alkenylene, substituted or unsubstituted linear or branched $C_2$-$C_{20}$ alkynylene, and substituted or unsubstituted $C_3$-$C_{10}$ cycloalkylene, $R_9$ in each instance is independently selected from the group consisting of substituted or unsubstituted linear or branched $C_1$-$C_{20}$ alkylene, substituted or unsubstituted linear or branched $C_2$-$C_{20}$ alkenylene, substituted or unsubstituted linear or branched $C_2$-$C_{20}$ alkynylene, substituted or unsubstituted $C_3$-$C_{10}$ cycloalkylene, and substituted or unsubstituted arylene, and p is from 1 to 100, and
p' is from 1 to 10.

2. The photochromic material of claim 1, wherein each $R_1$ is independently linear or branched $C_1$-$C_{10}$ alkyl, each R is independently hydrogen or linear or branched $C_1$-$C_{10}$ alkyl, and $R^b$ is hydrogen or linear or branched $C_1$-$C_{10}$ alkyl.

3. The photochromic material of claim 1, wherein Z is Si.

4. The photochromic material of claim 1, wherein said pendent silane group is selected from pendent silane groups represented by general formula I.

5. The photochromic material of claim 1, wherein said photochromic substituent is a photochromic pyran which is an indeno-fused naphthopyran.

6. The photochromic material of claim 5, wherein from 1 to less than all positions of said indeno-fused naphthopyran have bonded thereto said pendent silane group.

7. The photochromic material of claim 6, wherein said indeno-fused naphthopyran has bonded thereto 1 or 2 of said pendent silane groups.

8. A photochromic material comprising,
a photochromic compound comprising a photochromic substituent selected from the group consisting of photochromic pyrans, photochromic oxazines, and thermally reversible photochromic fulgides, wherein the photochromic substituent has bonded thereto at least one pendent silane group selected from the group consisting of, pendent silane groups represented by the following general formula II,

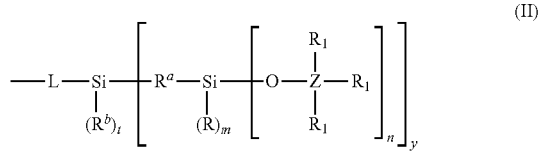

and combinations thereof,
wherein Z for each n is independently Si or C, R is hydrogen or $C_1$-$C_{10}$ hydrocarbyl, each $R_1$ is independently $C_1$-$C_{10}$ hydrocarbyl or halo substituted $C_1$-$C_{10}$ hydrocarbyl, m is 0 or 1, n is 2 or 3, provided that the sum of m and n is 3, L is a divalent linking group comprising at least one divalent moiety selected from the group consisting of divalent organic moieties, divalent inorganic moieties and combinations thereof, $R^a$ is a divalent linking group selected from divalent organic moieties, $R^b$ is hydrogen or $C_1$-$C_{10}$ hydrocarbyl, t is 0, 1 or 2, and y is 1, 2 or 3, provided that the sum of t and y is 3, wherein said divalent linking group of each L is independently selected from the group consisting of,

—C(O)—NH—$R_{10}$—,

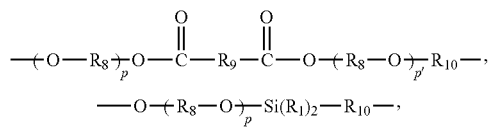

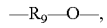

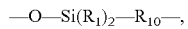

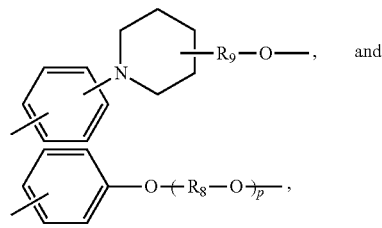

wherein each $R_1$ is independently as described with regard to general formula (I), $R_{10}$ in each instance is independently selected from the group consisting of substituted or unsubstituted linear or branched $C_1$-$C_{10}$ alkylene, substituted or unsubstituted linear or branched $C_2$-$C_{10}$ alkenylene, substituted or unsubstituted linear or branched $C_2$-$C_{10}$ alkynylene, substituted or unsubstituted $C_3$-$C_{10}$ cycloalkylene, and substituted or unsubstituted arylene, $R_8$ in each instance is independently selected from the group consisting of substituted or unsubstituted linear or branched $C_1$-$C_{20}$ alkylene, substituted or unsubstituted linear or branched $C_2$-$C_{20}$ alkenylene, substituted or unsubstituted linear or branched $C_2$-$C_{20}$ alkynylene, and substituted or unsubstituted $C_3$-$C_{10}$ cycloalkylene, $R_9$ in each instance is independently selected from the group consisting of substituted or unsubstituted linear or branched $C_1$-$C_{20}$ alkylene, substituted or unsubstituted linear or branched $C_2$-$C_{20}$ alkenylene, substituted or unsubstituted linear or branched $C_2$-$C_{20}$ alkynylene, substituted or unsubstituted $C_3$-$C_{10}$ cycloalkylene, and substituted or unsubstituted arylene, and p is from 1 to 100, and
p' is from 1 to 10.

9. A photochromic material comprising, a photochromic compound comprising a photochromic substituent selected from the group consisting of photochromic pyrans, photochromic oxazines, and thermally reversible photochromic fulgides, wherein the photochromic substituent has bonded thereto at least one pendent silane group selected from the group consisting of
(i) pendent silane groups represented by the following general formula I,

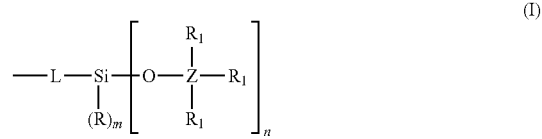

wherein Z for each n is independently Si or C, R is hydrogen or $C_1$-$C_{10}$ hydrocarbyl, each $R_1$ is independently $C_1$-$C_{10}$ hydrocarbyl or halo substituted $C_1$-$C_{10}$ hydrocarbyl, m is 0 or 1, and n is 2 or 3, provided that the sum of in and n is 3, (ii) pendent silane groups represented by the following general formula II,

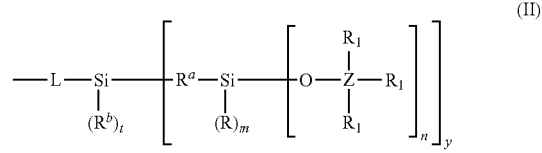

and combinations thereof,
wherein Z, R, $R_1$, m, and n are each independently as described with regard to general formula (I), $R^a$ of formula II is a divalent linking group which is linear or branched $C_1$-$C_{10}$ alkylene, $R^b$ is hydrogen or $C_1$-$C_{10}$ hydrocarbyl, t is 0, 1 or 2, and y is 1, 2 or 3, provided that the sum of t and y is 3, wherein L, independently for formula (I) and formula (II), is a divalent linking group comprising at least one divalent moiety selected from the group consisting of —O—, —S—, —Si($R_1$)$_2$— in which each $R_1$ is independently as described with regard to formula (I), —N(R$_2$)—, —C(O)—, —C(O)—O—, —O—C(O)—O—, —C(R$_3$)(R$_4$)—C(O)—O—, —C(R$_5$)(R$_6$)—C(O)—N(R$_7$)—, —C(O)—N(R$_7$)—, —NH—C(O)—O—,
—NH—C(O)—S—, —NH—C(S)—O—, —NH—C(S)—S—,

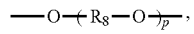

—R$_9$—O—, substituted or unsubstituted linear or branched C$_1$-C$_{20}$ alkylene, substituted or unsubstituted, linear or branched C$_2$-C$_{20}$ alkenylene, substituted or unsubstituted linear or branched C$_2$-C$_{20}$ alkynylene, substituted or unsubstituted C$_3$-C$_{10}$ cycloalkylene, substituted or unsubstituted C$_3$-C$_{10}$ heterocycloalkylene, substituted or unsubstituted arylene, substituted or unsubstituted heteroarylene, and combinations of two or more thereof, wherein R$_2$, R$_3$, R$_4$, R$_5$, R$_6$, and R$_7$ are each independently selected from the group consisting of hydrogen, substituted or unsubstituted linear or branched alkyl, substituted or unsubstituted C$_3$-C$_{10}$ cycloalkyl, substituted or unsubstituted C$_3$-C$_{10}$ heterocycloalkyl, substituted or unsubstituted aryl, and substituted or unsubstituted heteroaryl, wherein R$_8$ for each p is independently selected from the group consisting of substituted or unsubstituted linear or branched C$_1$-C$_{20}$ alkylene, substituted or unsubstituted linear or branched C$_2$-C$_{20}$ alkenylene, substituted or unsubstituted linear or branched C$_2$-C$_{20}$ alkynylene, and substituted or unsubstituted C$_3$-C$_{10}$ cycloalkylene, and p is from 1 to 100, and wherein R$_9$ is selected from the group consisting of substituted or unsubstituted linear or branched C$_1$-C$_{20}$ alkylene, substituted or unsubstituted linear or branched C$_2$-C$_{20}$ alkenylene, substituted or unsubstituted linear or branched C$_2$-C$_{20}$ alkynylene, substituted or unsubstituted C$_3$-C$_{10}$ cycloalkylene, and substituted or unsubstituted arylene.

10. A photochromic material comprising, a photochromic compound comprising a photochromic substituent selected from the group consisting of photochromic pyrans, photochromic oxazines, and thermally reversible photochromic fulgides, wherein the photochromic substituent has bonded thereto at least one pendent silane group selected from the group consisting of, (i) pendent silane groups represented by the following general formula I,

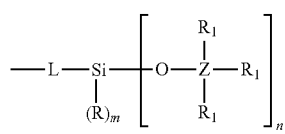

wherein Z for each n is independently Si or C, R is selected from hydrogen or C$_1$-C$_{10}$ hydrocarbyl, each R$_1$ is independently C$_1$-C$_{10}$ hydrocarbyl or halo substituted C$_1$-C$_{10}$ hydrocarbyl, m is 0 or 1, and n is 2 or 3, provided that the sum of m and n is 3, (ii) pendent silane groups represented by the following general formula H,

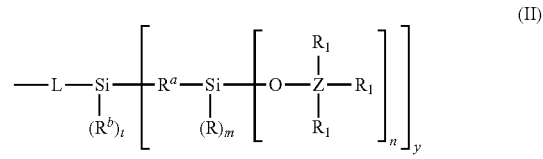

and combinations thereof, wherein Z, R, R$_1$, m, and n are each independently as described with regard to general formula (I), R$^a$ is a divalent linking group selected, from divalent organic moieties, R$^b$ is hydrogen or C$_1$-C$_{10}$ hydrocarbyl, t is 0, 1 or 2, and y is 1, 2 or 3, provided that the sum of t and y is 3, wherein L, independently for formula (I) and formula (II), is a divalent linking group comprising at least one divalent moiety selected from the group consisting of —O—, —Si(R$_1$)$_2$— where R$_1$ is as described with regard to general formula (II, —C(O)—O—,

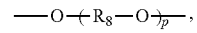

—R$_9$—O—, substituted or unsubstituted linear or branched C$_1$-C$_{10}$ alkylene, substituted or unsubstituted linear or branched C$_2$-C$_{10}$ alkenylene, substituted or unsubstituted linear or branched C$_2$-C$_{10}$ alkynylene, —O—C(O)—R$_9$—C(O)—O—

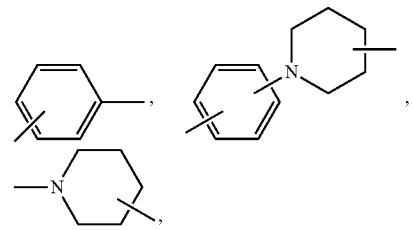

and combinations of two or more thereof, wherein R$_8$ for each p is independently selected from the group consisting of substituted or unsubstituted linear or branched C$_1$-C$_{10}$ alkylene, substituted or unsubstituted linear or branched C$_2$-C$_{10}$ alkenylene, and substituted or unsubstituted linear or branched C$_2$-C$_{10}$ alkynylene, and p is from 1 to 10, and wherein each R$_9$ is independently selected from the group consisting of substituted or unsubstituted linear or branched C$_1$-C$_{10}$ alkylene, substituted or unsubstituted linear or branched C$_2$-C$_{10}$ alkenylene, substituted or unsubstituted linear or branched C$_2$-C$_{10}$ alkynylene, substituted or unsubstituted C$_3$-C$_{10}$ cycloalkylene, and substituted or unsubstituted arylene.

* * * * *